United States Patent
Krishnan et al.

(10) Patent No.: US 12,247,055 B2
(45) Date of Patent: *Mar. 11, 2025

(54) GENERAL AMYLOID INTERACTION MOTIF (GAIM)

(71) Applicant: Amyl Therapeutics SRL, Seraing (BE)

(72) Inventors: Rajaraman Krishnan, Ashland, MA (US); Eva Asp, Newton, MA (US); Ming Proschitsky, Winchester, MA (US); Richard Fisher, Cambridge, MA (US)

(73) Assignee: Amyl Therapeutics SRL, Seraing (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,697

(22) Filed: May 19, 2023

(65) Prior Publication Data
US 2023/0279064 A1    Sep. 7, 2023

Related U.S. Application Data

(63) Continuation of application No. 17/251,351, filed as application No. PCT/US2019/037179 on Jun. 14, 2019, now Pat. No. 11,692,017.

(60) Provisional application No. 62/749,499, filed on Oct. 23, 2018, provisional application No. 62/685,757, filed on Jun. 15, 2018.

(51) Int. Cl.
| | | |
|---|---|---|
| *C07K 14/47* | (2006.01) | |
| *A61K 38/00* | (2006.01) | |
| *A61K 47/68* | (2017.01) | |

(52) U.S. Cl.
CPC .......... *C07K 14/4703* (2013.01); *A61K 47/68* (2017.08); *A61K 38/00* (2013.01); *C07K 2319/20* (2013.01)

(58) Field of Classification Search
None
See application file for complete search history.

(56) References Cited

U.S. PATENT DOCUMENTS 11,692,017 B2 *   7/2023   Krishnan   ........... C07K 14/4703
                                              514/17.7

FOREIGN PATENT DOCUMENTS

| WO | WO 2013/082114 A1 | 6/2013 |
| WO | WO 2014/055515 A1 | 4/2014 |
| WO | WO 2014/193935 A1 | 12/2014 |
| WO | WO 2016/090022 A1 | 6/2016 |

OTHER PUBLICATIONS

Krishnan et al. "A Bacteriophage Capsid Protein Provides a General Amyloid Interaction Motif (GAIM) That Binds and Remodels Misfolded Protein Assemblies" J. Mol. Biol. 426:2500-2516. (Year: 2014).*
Fessel and Wien (2017) "Alzheimer's Disease Combination Treatment," Neurobiology of Aging, Tarrytown, NY, vol. 63 p. 165.
Krishnan et al. (2014) "A Bacteriophage Capsid Protein Provides a General Amyloid Interaction Motif (GAIM) That Binds and Remodels Misfolded Protein Assemblies," *J. Mol. Biol.*, 426:2500-2519.
Krishnan et al. (2017) "Conformation as the Therapeutic Target for Neurodegenerative Diseases," *Current Alzheimer Research*, 14(4):393-402.
Manix et al. (2015) "Creutzfeldt-Jakob Disease: Updated Diagnostics Criteria, Treatment Algorithm, and the Utility of Brain Biopsy," *Neurosurgical Focus*, vol. 39, No. 5 p. E2.

* cited by examiner

*Primary Examiner* — Sudhakar Katakam
*Assistant Examiner* — Zachary J Miknis
(74) *Attorney, Agent, or Firm* — FINNEGAN, HENDERSON, FARABOW, GARRETT & DUNNER, LLP

(57) ABSTRACT

The present invention relates to variants of the general amyloid interaction motif (GAIM) of bacteriophage gene 3 protein (g3p) and fusion proteins thereof. The GAIM variants and fusion proteins of the invention are partially or fully deimmunized and demonstrate superior binding and specificity to a diverse array of amyloid proteins, and exhibit enhanced amyloid remodeling and inhibition of amyloid aggregation. The present invention further relates to nucleic acids, vectors, host cells, and methods of making the GAIM variants and fusion proteins thereof. The present invention also relates to pharmaceutical compositions and methods of increasing bacteriophage infectivity, methods of detecting amyloid aggregates, and methods of diagnosing and/or treating a disease associated with misfolded and/or aggregated amyloid protein.

26 Claims, 32 Drawing Sheets

Specification includes a Sequence Listing.

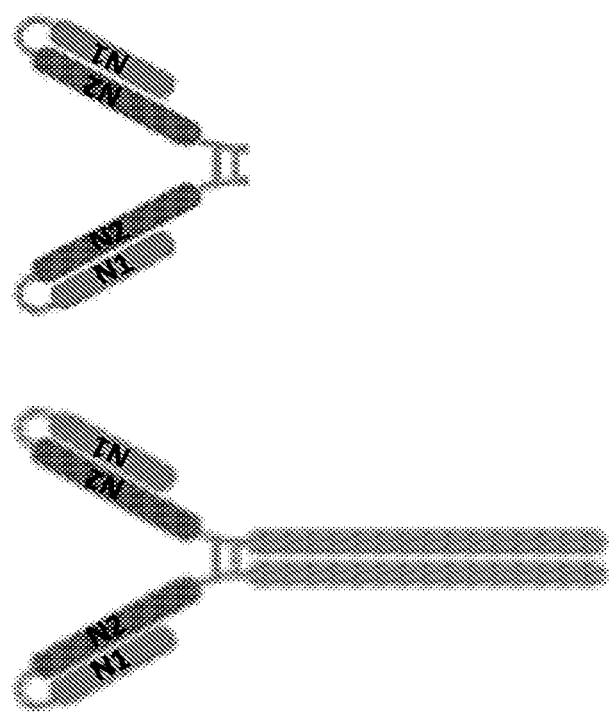
Fig. 1B
Fig. 1C
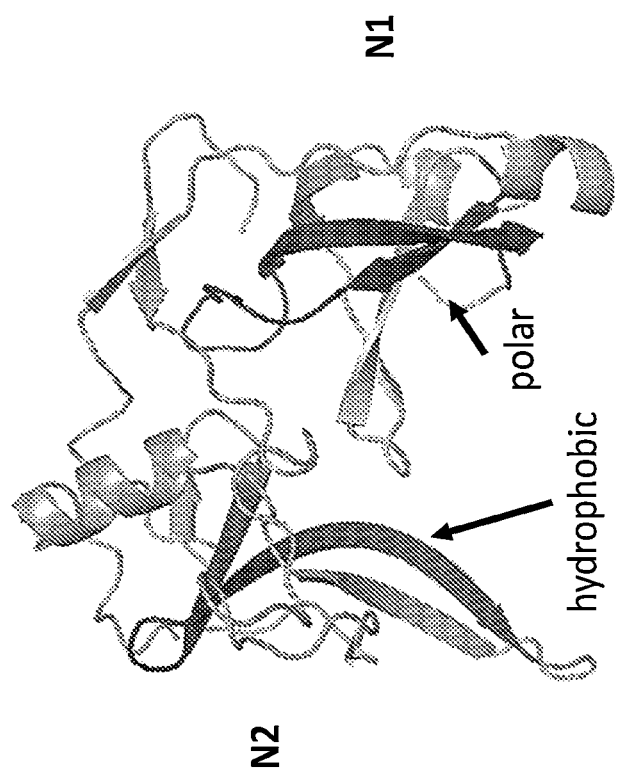
Fig. 1A

```
              10        20        30
     ....|....|....|....|....|....|....
SEQ ID NO:1  AETVESCLAKPHTENSFTNVWKDDKTLDRYAN
SEQ ID NO:2  ATTDAECLSKPAFDGTLSNVWKEGDS--RYAN
```

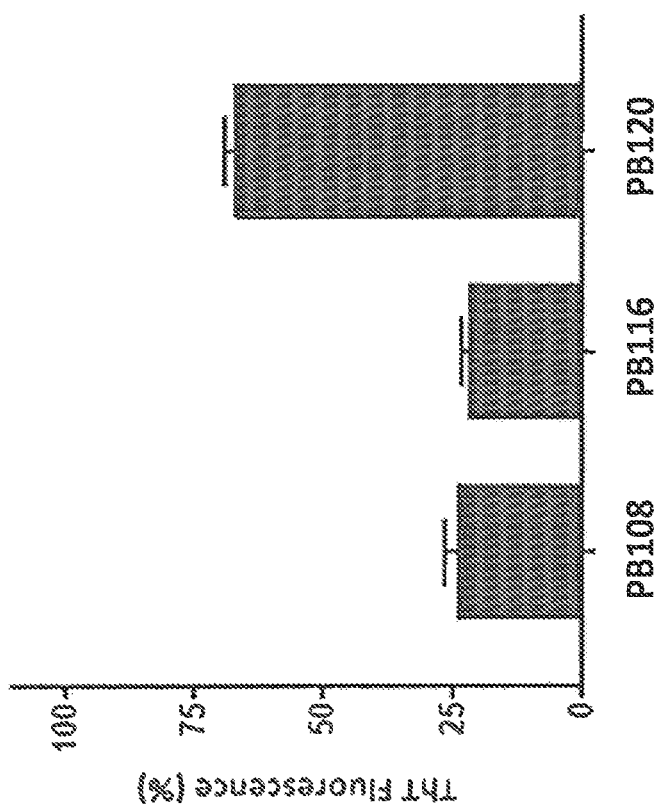

GENERAL AMYLOID INTERACTION MOTIF (GAIM)

This application claims priority to U.S. application Ser. No. 17/251,351, filed Dec. 11, 2020, which is a national stage application that claims priority to International Application No. PCT/US2019/037179, filed Jun. 14, 2019, which claims priority to U.S. Provisional Application No. 62/685,757, filed Jun. 15, 2018, and U.S. Provisional Application No. 62/749,499, filed Oct. 23, 2018, the disclosure of which is incorporated herein by reference in their entirety.

The invention relates to polypeptides comprising a variant of the general amyloid interaction motif (GAIM) of filamentous bacteriophage gene 3 protein ("g3p," also known as "p3" or "pIII") such that the polypeptides are partially or fully deimmunized and demonstrate superior potency, superior structural stability, and increased binding specificity to amyloid proteins relative to the prior art. Nucleic acid molecules and constructs encoding such polypeptides, host cells transformed with such nucleic acid molecules, and methods of making such polypeptides recombinantly are encompassed. In addition, the invention relates to diagnostic and pharmaceutical compositions comprising the polypeptides disclosed herein, to the use of diagnostic compositions to detect amyloid aggregates and/or to diagnose a disease associated with misfolded and/or aggregated protein, and to the therapeutic and/or prophylactic use of pharmaceutical compositions to decrease amyloid load, prevent aggregation, disaggregate amyloid, or otherwise treat or prevent a disease associated with misfolded and/or aggregated amyloid protein, such as systemic and peripheral amyloid diseases, neurodegenerative diseases including neurodegenerative tauopathies, and transmissible spongiform encephalopathies (prion-associated diseases). Polypeptides of the invention include fusion proteins and amyloid-binding portions thereof.

Bacteriophage g3p directly binds amyloid fibers, and bacteriophage-mediated amyloid disaggregation (e.g., remodeling) is dependent upon this initial binding step. See, e.g., WO 2013/082114 A1, hereby incorporated by reference in its entirety. The inventors previously identified a minimal sequence of g3p required for amyloid binding, amyloid disaggregation, and/or prevention of formation of amyloid aggregates. Id. This minimal sequence is encompassed by the general amyloid interaction motif (GAIM), which comprises the N1 and N2 domains of g3p, and led to the generation of g3p polypeptides (including mutants, fragments, fusion proteins, or pharmaceutical compositions thereof) that are capable of binding to amyloid protein and/or disaggregating amyloid proteins. See id.; WO 2014/055515 A1, hereby incorporated by reference in its entirety. The g3p polypeptides disclosed in WO 2013/082114 A1 and WO 2014/055515 A1 are effective for the prevention or treatment of diseases associated with misfolded and/or aggregated amyloid proteins. Id. However, these g3p polypeptides also comprise human T-cell epitopes that may elicit an unwanted immune response in patients. Partially deimmunized g3p polypeptides were therefore developed, comprising mutations that remove up to four of the five T-cell epitopes present in native g3p. See WO 2014/193935 A1, hereby incorporated by reference in its entirety.

Further, the recombinant production in animal cells of g3p polypeptides that bind amyloid—and are useful for detection, diagnosis, prevention, or treatment of amyloid-related diseases or conditions—was limited by the presence of a potential N-glycosylation site. Thus, improved g3p polypeptides, including partially deimmunized g3p polypeptides, were generated in which the potential N-glycosylation site was removed by one or more mutations. See WO 2016/090022 A8, hereby incorporated by reference in its entirety.

Despite these advances, there remains a need in the art for g3p polypeptides that are more stable, potent, and specific as well as fully or almost fully deimmunized.

Generating polypeptides with these sets of therapeutic qualities has so far posed a significant challenge, at least in part due to certain inverse relationships in the g3p polypeptides: First, our prior attempts to remove T-cell epitope 2, which is required for full deimmunization of a g3p polypeptide, have consistently resulted in reduced amyloid-binding ability. Second, our prior attempts to increase the stability of the N1-N2 domains of GAIM have also consistently caused reduced amyloid-binding activity. For example, a super-stabilized GAIM variant, PB113, exhibits poor amyloid-binding capability. Third, instability of the N2 domain drives promiscuous interactions with non-amyloid substrates like soluble proteins, sticky molten-globule structures and non-amyloid fibrillar polymers, such as collagen and elastin. Thus, destabilizing N2 to increase amyloid-binding activity sacrifices specificity, while stabilizing N2 to avoid off-target binding sacrifices binding to amyloid. Surprisingly, all three inverse relationships were overcome by generating fusion proteins comprising GAIM variants and fusions thereof in an "open-stabilized" conformation.

Unlike the prior art, the open-stabilized polypeptides described herein demonstrate potent amyloid-binding and remodeling activities across a wide array of amyloids while maintaining protein stability and binding specificity. Thus, in some aspects, the present invention relates to open-stabilized variants of GAIM (GAIM), GAIM-immunoglobulin (GAIM-Ig) fusion proteins, or pharmaceutical compositions thereof, that are at least partially deimmunized and have superior amyloid-binding activity, amyloid-binding specificity, and amyloid remodeling activity. In some aspects, these open-stabilized GAIM variants, GAIM-Ig fusion proteins, or pharmaceutical compositions thereof are fully deimmunized without sacrificing potent and specific amyloid binding and without sacrificing structural stability. The open-stabilized GAIM variants and GAIM-Ig fusions described herein are capable of engaging and removing amyloids in brain and peripheral organs and constitute a novel set of polypeptides with superior ability to detect, diagnose, prevent, delay onset of and/or treat diseases associated with misfolded and/or aggregated amyloid protein.

Additional objects and advantages of the invention are set forth in part in the description which follows, and will be obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

FIG. 1A is a graphical representation of the tertiary structure of the GAIM N1 and N2 domains (shown using PDB structure 2G3P). β-strands subjected to site-directed mutagenesis are shown in dark grey. Arrows indicate the location of polar residues in N1 and hydrophobic residues in N2. FIG. 1B is a graphical representation of a GAIM-Ig fusion of the invention. FIG. 1C is a graphical representation of a GAIM dimer.

FIG. 5C shows two transitions, the first between 1 M and 2 M GuHCl and the second between 2 M and 4 M GuHCl. Relative fluorescence intensities at 340 nm (excitation 280 nm) were plotted at various concentrations of GuHCl.

FIG. 6A is a scatter plot showing the Aβ42 fiber-binding potency of GAIM variants correlating with Tm1 (Spearman correlation coefficient=0.703, p<0.0001). FIG. 6B is a scatter plot showing the ftau fiber-binding potency of GAIM variants correlating with Tm1 (Spearman correlation coefficient=0.878, p<0.0001). Variants with poor ftau binding are presented $EC_{50}$=1000 nM due to inaccuracy in the curve fit for variants that does not reach saturation in the ELISA. For both FIG. 6A and FIG. 6B, the GAIM scaffold PB120 is represented by a grey triangle and variants are represented by circles. A decrease in Tm1 indicates a more open conformation of GAIM, resulting in increased binding, whereas stabilized variants with higher Tm1 tend to lose binding activity.

FIG. 7A compares amyloid binding for the GAIM scaffold (closed circle) and stabilized variants thereof. FQGN, VNGV, and QGGK are SEQ ID NOs:8-10, respectively. FIG. 7B shows the superior binding of open-stabilized (but not super-stabilized) GAIM-Ig fusion proteins. Open-stabilized polypeptides, (other than the super-stabilized polypeptide PB113, shown on the far right), are indicated within the open box.

FIG. 8A shows binding to Aβ3-42-Pyro fibers; FIG. 8B shows binding to Aβ1-42 E22Q fibers; FIG. 8C shows binding to Aβ11-42 fibers; FIG. 8D shows binding to Aβ11-42-Pyro fibers. The aggregates used for these experiments show very diverse morphology that range from long unbranched fibers (Aβ1-42 E22Q fibers) to highly zig-zagged conformers (Aβ3-42-Pyro fibers). Pyro=pyroglutamate.

FIG. 10A further shows a comparison to remodeling effected by 6E10 MAb. Circles=mean; Bars=standard deviation. FIG. 10B further demonstrates the correlation between Aβ42 binding and remodeling by various GAIM-Ig fusion proteins. Open-stabilized GAIM-Ig-fusions are represented by dark grey upside-down triangles. The GAIM scaffold is depicted by a light grey right-side-up triangle. Circles represent other tested GAIM-Ig fusions. FIG. 10C compares the remodeling efficiency of a representative open-stabilized polypeptide (circles) against the remodeling efficiency of the GAIM scaffold (triangles) or fiber alone (squares). Bars=standard deviation. Greater remodeling efficiency is demonstrated by greater dissolution of fibers in urea (e.g., lower ThT fluorescence). FIG. 10D shows transmission electron microscopy (TEM) images showing Aβ42 fibers before (left) and after (right) incubation with 0.8 μM PB108 at 37° C. for six days.

FIG. 11A compares the remodeling efficiencies of representative open-stabilized GAIM-Ig fusion protein PB108 and the super-stabilized fusion protein PB113. Remodeling is indicated by the presence of tauKL monomers and dimers (middle panel) in treated aggregates. FIG. 11B compares the remodeling efficiencies of two representative open-stabilized GAIM-Ig fusion proteins and the GAIM scaffold, at different concentrations of fusion protein. Error bars represent standard deviation from three independent experiments. FIG. 11C shows TEM images showing tauKL fibers before (left) and after (right) incubation with 100 nM PB108 at 37° C. for three days.

FIGS. 12A-12D depict inhibition of amyloid assembly by GAIM-Ig fusion proteins of the invention. Error bars represent standard deviation from three or more independent experiments. FIG. 12A shows concentration-dependent inhibition of Aβ42 fiber assembly. PB120 (control scaffold) is represented by circles, PB108 by squares, and PB116 by triangles. FIG. 12B compares inhibition of Aβ42 fiber assembly at 250 nM GAIM fusion. FIG. 12C shows concentration-dependent inhibition of tauKL fiber assembly. PB120 (control scaffold) is represented by circles, PB108 by squares, and PB116 by triangles. FIG. 12D compares inhibition of tauKL fiber assembly at 250 nM GAIM fusion.

Brief Description of Sequences

SEQ ID NO: 1 = AETVESCLAKPHTENSFTNVWKDDKTLDRYAN

SEQ ID NO: 2 = ATTDAECLSKPAFDGTLSNVWKEGDSRYAN

Figure 2:
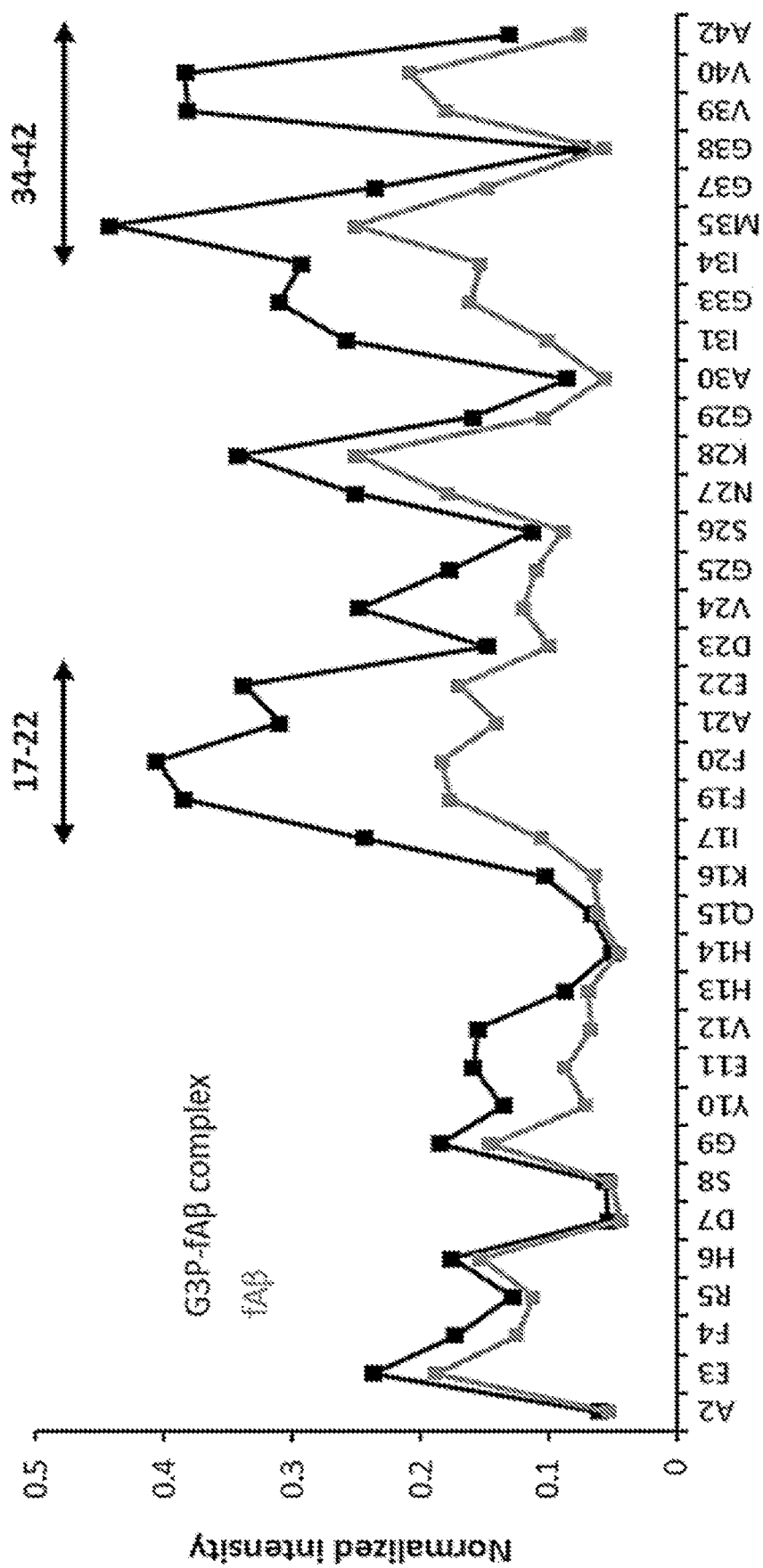
FIG. 2 depicts results of hydrogen/deuterium (H/D) exchange studies showing the GAIM-interacting sequences in fAβ42.

SEQ ID NO: 3 = DDKTLD;

SEQ ID NO: 4 = EGDS

SEQ ID NO: 5 = FQNN;

SEQ ID NO: 6 = RQGA;

SEQ ID NO: 7 = QGTDPVK;

SEQ ID NO: 8 = FQGN;

SEQ ID NO: 9 = VNGV;

SEQ ID NO: 10 = QGGK

SEQ ID NO: 11 =
MAETVESCLAKPHTENSFTNVWKDDKTLDRYANYEGCLWNAGGVVVCTGDET
QCYGTWVPIGLAIPENEGGGSEGGGSEGGGSEGGGTKPPEYGDTPIPGYTYI
NPLDGTYPPGTEQNPANPNPSLEESQPLNTFMFQNNRFRNRQGALTVYTGTF
TQGTDPVKTYYQYTPVSSRAMYDAYWNGKFRDCAFHSGFNEDPFVCEYQGQ
SSDLPQPPANAGGESGGGSGGGSEGGGSEGGGSEGGGSEGGGSGGGSGS
GARSDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSV
MHEALHNHYTQKSLSLSPGK

SEQ ID NO: 12 =
MAETVESCLAKPHTENSFTNVWKDDKTLDRYANYEGCLWNAGGVVVCTGDE
TQCYGTWVPIGLAIPENEGGGSEGGGSEGGGSEGGGTKPPEYGDTPIPGYTYI
NPLDGTYPPGTEQNPANPNPSLEESQPLNTFMFQNNRFRNRQGALTVYTGTF
TQGTDPVKTYYQYTPVSSRAMYDAYWNGKFRDCAFHSGFNEDPFVCEYQGQ
SSDLPQPPANAGGESGGGSGGGSEGGGSEGGGSEGGGSEGGGSGGGSGS
G

SEQ ID NO: 13 =
MAETVESCLAKPHTENSFTNVWKDDKTLDRYANYEGCLWNAGGVVVCTGDET
QCYGHWVPIGLAIPENEGGGSEGGGSEGGGSEGGGTKPPEYGDTPIPGYTYI
NPLDGTYPPGTEQNPANPNPSLEESQPLNTFMFQNNRFRNRQGALTVYTGTF
TQGTDPVKTYYQYTPVSSRAMYDAYWNGKFRDCAFHSGFNEDPFVCEYQGQ
SSDLPQPPANAGGESGGGSGGGSEGGGSEGGGSEGGGSEGGGSGGGSGS
GARSDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSV
MHEALHNHYTQKSLSLSPGK

SEQ ID NO: 14 =
MAETVESCLAKPHTENSFTNVWKDDKTLDRYANYEGCLWNAGGVVVCTGDE
TQCYGHWVPIGLAIPENEGGGSEGGGSEGGGSEGGGTKPPEYGDTPIPGYTY
INPLDGTYPPGTEQNPANPNPSLEESQPLNTFMFQNNRFRNRQGALTVYTGTF
TQGTDPVKTYYQYTPVSSRAMYDAYWNGKFRDCAFHSGFNEDPFVCEYQGQ
SSDLPQPPANAGGESGGGSGGGSEGGGSEGGGSEGGGSEGGGSGGGSGS
G

SEQ ID NO: 15 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQNNRFRNRQGALTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG
ARSDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVM
HEALHNHYTQKSLSLSPGK

SEQ ID NO: 16 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQNNRFRNRQGALTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG

Brief Description of Sequences

SEQ ID NO: 17 =
MAETVESSLAKPHIEGSFTNVWKDDKTLDWYANYEGILWKATGVVVITGDETQ
VYAIWVPVGLAIPENEGGGSEGGGSEGGGSEGGGTKPPEYGDTPIPGYIYINP
LDGTYPPGTEQNPANPNPSLEESHPLNTFMFQGNRFRNROGALTVYTGTFTQ
GTDPVKTYYQYTPVSSRAMYDAYWNGKFRDVAFHSGFNEDPLVAEYQGQLS
YLPQPPANAGGESGGGSGGGSEGGGSEGGGSEGGGSEGGGSGGGSGSGA
RSDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMH
EALHNHYTQKSLSLSPGK

SEQ ID NO: 18 =
MAETVESSLAKPHIEGSFTNVWKDDKTLDWYANYEGILWKATGVVVITGDETQ
VYAIWVPVGLAIPENEGGGSEGGGSEGGGSEGGGTKPPEYGDTPIPGYIYINP
LDGTYPPGTEQNPANPNPSLEESHPLNTFMFQGNRFRNROGALTVYTGTFTQ
GTDPVKTYYQYTPVSSRAMYDAYWNGKFRDVAFHSGFNEDPLVAEYQGQLS
YLPQPPANAGGESGGGSGGGSEGGGSEGGGSEGGGSEGGGSGGGSGSG

SEQ ID NO: 19 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQGNRFRNRQGALTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG

SEQ ID NO: 20 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQNNRFRNVNGVLTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG

SEQ ID NO: 21 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQGNRFRARQGALTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG

SEQ ID NO: 22 =
MAETVESCLAKPHTENSFTNVWKEGDSRYANYEGCLWNAGGVVVCTGDETQ
CYGHWVPIGLAIPENEGGGSEGGGSEGGGSEGGGTKPPEYGDTPIPGYTYIN
PLDGTYPPGTEQNPANPNPSLEESQPLNTFMFQNNRFRAVNGVLTVYTGTFT
QGTDPVKTYYQYTPVSSRAMYDAYWNGKFRDCAFHSGFNEDPFVCEYQGQS
SDLPQPPANAGGESGGGSGGGSEGGGSEGGGSEGGGSEGGGSGGGSGSG

SEQ ID NO: 23 =
MAETVESCLAKPHTENSFTNVWKEGDSRYANYEGCLWNAGGVVVCTGDEHQ
CYGTWPIGLAIPENEGGGSEGGGSEGGGSEGGGTKPPEYGDTPIPGYTYINP
LDGTYPPGTEQNPANPNPSLEESQPLNTFMFQGNRFRARQGALTVYTGTFTQ
GTDPVKTYYQYTPVSSRAMYDAYWNGKFRDCAFHSGFNEDPFVCEYQGQSS
DLPQPPANAGGESGGGSGGGSEGGGSEGGGSEGGGSEGGGSGGGSGSG

SEQ ID NO: 24 =
MAETVESCLAKPHTENSFTNVWKEGDSRYANYEGCLWNAGGVVVCTGDEHQ
CYGTWVPIGLAIPENEGGGSEGGGSEGGGSEGGGTKPPEYGDTPIPGYTYINP
LDGTYPPGTEQNPANPNPSLEESQPLNTFMFQNNRFRAVNGVLTVYTGTFTQ
GTDPVKTYYQYTPVSSRAMYDAYWNGKFRDCAFHSGFNEDPFVCEYQGQSS
DLPQPPANAGGESGGGSGGGSEGGGSEGGGSEGGGSEGGGSGGGSGSG

SEQ ID NO: 25 =
MAETVESCLAKPHTENSFTNVWKEGDSRYANYEGCLWNAGGVVVCTGDEHQ
CYGTWVPIGLAIPENEGGGSEGGGSEGGGSEGGGTKPPEYGDTPIPGYTYINP
LDGTYPPGTEQNPANPNPSLEESQPLNTFMFQGNRFRNRQGALTVYTGTFTQ
GTDPVKTYYQYTPVSSRAMYDAYWNGKFRDCAFHSGFNEDPFVCEYQGQSS
DLPQPPANAGGESGGGSGGGSEGGGSEGGGSEGGGSEGGGSGGGSGSG

SEQ ID NO: 26 =
MAETVESCLAKPHTENSFTNVWKEGDSRYANYEGCLWAAGGVVVCTGDEHQ
CYGTWVPIGLAIPENEGGGSEGGGSEGGGSEGGGTKPPEYGDTPIPGYTYINP
LDGTYPPGTEQNPANPNPSLEESQPLNTFMFQGNRFRNRQGALTVYTGTFTQ
GTDPVKTYYQYTPVSSRAMYDAYWNGKFRDCAFHSGFNEDPFVCEYQGQSS
DLPQPPANAGGESGGGSGGGSEGGGSEGGGSEGGGSEGGGSGGGSGSG

Brief Description of Sequences

SEQ ID NO: 27 = GGGGS;

SEQ ID NO: 28 = GGGS

SEQ ID NO: 29 =
MAETVESCLAKPHTENSFTNVWKEGDSRYANYEGCLWNAGGVVVCTGDETQCY
GHWVPIGLAIPENEGGGSEGGGSEGGGSEGGGTKPPEYGDTPIPGYTYINPLDG
TYPPGTEQNPANPNPSLEESQPLNTFMFQGNRFRNRQGALTVYTGTFTQGTDPV
KTYYQYTPVSSRAMYDAYWNGKFRDCAFHSGFNEDPFVCEYQGQSSDLPQPPA
NAGGESGGGSGGGSEGGGSEGGGSEGGGSEGGGSGGGSGSGARSDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

SEQ ID NO: 30 =
MAETVESCLAKPHTENSFTNVWKEGDSRYANYEGCLWNAGGVVVCTGDETQCY
GHWVPIGLAIPENEGGGSEGGGSEGGGSEGGGTKPPEYGDTPIPGYTYINPLDG
TYPPGTEQNPANPNPSLEESQPLNTFMFQNNRFRNVNGVLTVYTGTFTQGTDPV
KTYYQYTPVSSRAMYDAYWNGKFRDCAFHSGFNEDPFVCEYQGQSSDLPQPPA
NAGGESGGGSGGGSEGGGSEGGGSEGGGSEGGGSGGGSGSGARSDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

SEQ ID NO: 31 =
MAETVESCLAKPHTENSFTNVWKEGDSRYANYEGCLWNAGGVVVCTGDETQCY
GHWVPIGLAIPENEGGGSEGGGSEGGGSEGGGTKPPEYGDTPIPGYTYINPLDG
TYPPGTEQNPANPNPSLEESQPLNTFMFQGNRFRARQGALTVYTGTFTQGTDPV
KTYYQYTPVSSRAMYDAYWNGKFRDCAFHSGFNEDPFVCEYQGQSSDLPQPPA
NAGGESGGGSGGGSEGGGSEGGGSEGGGSEGGGSGGGSGSGARSDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

SEQ ID NO: 32 =
MAETVESCLAKPHTENSFTNVWKEGDSRYANYEGCLWNAGGVVVCTGDETQCY
GHWVPIGLAIPENEGGGSEGGGSEGGGSEGGGTKPPEYGDTPIPGYTYINPLDG
TYPPGTEQNPANPNPSLEESQPLNTFMFQNNRFRAVNGVLTVYTGTFTQGTDPV
KTYYQYTPVSSRAMYDAYWNGKFRDCAFHSGFNEDPFVCEYQGQSSDLPQPPA
NAGGESGGGSGGGSEGGGSEGGGSEGGGSEGGGSGGGSGSGARSDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

SEQ ID NO: 33 =
MAETVESCLAKPHTENSFTNVWKEGDSRYANYEGCLWNAGGVVVCTGDEHQC
YGTWVPIGLAIPENEGGGSEGGGSEGGGSEGGGTKPPEYGDTPIPGYTYINPLD
GTYPPGTEQNPANPNPSLEESQPLNTFMFQGNRFRARQGALTVYTGTFTQGTDP
VKTYYQYTPVSSRAMYDAYWNGKFRDCAFHSGFNEDPFVCEYQGQSSDLPQPP
ANAGGESGGGSGGGSEGGGSEGGGSEGGGSEGGGSGGGSGSGARSDKTHT
CPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSL
SPGK

SEQ ID NO: 34 =
MAETVESCLAKPHTENSFTNVWKEGDSRYANYEGCLWNAGGVVVCTGDEHQC
YGTWVPIGLAIPENEGGGSEGGGSEGGGSEGGGTKPPEYGDTPIPGYTYINPLD
GTYPPGTEQNPANPNPSLEESQPLNTFMFQNNRFRAVNGVLTVYTGTFTQGTDP
VKTYYQYTPVSSRAMYDAYWNGKFRDCAFHSGFNEDPFVCEYQGQSSDLPQPP
ANAGGESGGGSGGGSEGGGSEGGGSEGGGSEGGGSGGGSGSGARSDKTHT
CPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSL
SPGK

Brief Description of Sequences

SEQ ID NO: 35 =
MAETVESCLAKPHTENSFTNVWKEGDSRYANYEGCLWNAGGVVVCTGDEHQC
YGTWVPIGLAIPENEGGGSEGGGSEGGGSEGGGTKPPEYGDTPIPGYTYINPLD
GTYPPGTEQNPANPNPSLEESQPLNTFMFQGNRFRNRQGALTVYTGTFTQGTDP
VKTYYQYTPVSSRAMYDAYWNGKFRDCAFHSGFNEDPFVCEYQGQSSDLPQPP
ANAGGESGGGSGGGSEGGGSEGGGSEGGGSEGGGSGGGSGSGARSDKTHT
CPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSL
SPGK

SEQ ID NO: 36 =
MAETVESCLAKPHTENSFTNVWKEGDSRYANYEGCLWAAGGVVVCTGDEHQCY
GTWVPIGLAIPENEGGGSEGGGSEGGGSEGGGTKPPEYGDTPIPGYTYINPLDG
TYPPGTEQNPANPNPSLEESQPLNTFMFQGNRFRNRQGALTVYTGTFTQGTDPV
KTYYQYTPVSSRAMYDAYWNGKFRDCAFHSGFNEDPFVCEYQGQSSDLPQPPA
NAGGESGGGSGGGSEGGGSEGGGSEGGGSEGGGSGGGSGSGARSDKTHTC
PPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

SEQ ID NO: 37 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGACTCAGT
GCTACGACACTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAGG
GAACCGCTTCAGGAACAGACAGGGAGCGCTGACCGTGTACACTGGCACCTTC
ACACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGTGGATCCGAAGGAGGCGGATCCGAGGGT
GGAGGCTCCGAAGGGGGAGGCTCTGGTGGTGGCTCCGGATCGGGA

SEQ ID NO: 38 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGACTCAGT
GCTACGACACTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAAAC
AACCGCTTCAGGAACGTGAACGGAGTGCTGACCGTGTACACTGGCACCTTCA
CACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGTGGATCCGAAGGAGGCGGATCCGAGGGT
GGAGGCTCCGAAGGGGGAGGCTCTGGTGGTGGCTCCGGATCGGGA

SEQ ID NO: 39 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGACTCAGT
GCTACGACACTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAGG
GAACCGCTTCAGGTAGACAGGGAGCGCTGACCGTGTACACTGGCACCTTC
ACACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGTGGATCCGAAGGAGGCGGATCCGAGGGT
GGAGGCTCCGAAGGGGGAGGCTCTGGTGGTGGCTCCGGATCGGGA

Brief Description of Sequences

SEQ ID NO: 40 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGACTCAGT
GCTACGGACACTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAAAC
AACCGCTTCAGGGCCGTGAACGGAGTGCTGACCGTGTACACTGGCACCTTCA
CACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGA

SEQ ID NO: 41 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGCACCAGT
GCTACGGAACTTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAGG
GAACCGCTTCAGGGCTAGACAGGGAGCGCTGACCGTGTACACTGGCACCTTC
ACACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGA

SEQ ID NO: 42 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGCACCAGT
GCTACGGAACTTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAAAC
AACCGCTTCAGGGCCGTGAACGGAGTGCTGACCGTGTACACTGGCACCTTCA
CACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGA

SEQ ID NO: 43 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGCATCAGT
GCTACGGAACCTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAGG
GAACCGCTTCAGGAACAGACAGGGAGCGCTGACCGTGTACACTGGCACCTTC
ACACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGA

SEQ ID NO: 44 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGGCCGCCGGTGGAGTGGTCGTCTGCACCGGGGATGAGCATCAGT
GCTACGGAACCTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC

| Brief Description of Sequences |
|---|
| CAAACCCTAGCCTCGAGGAATCCCAGCCGTTGAACACCTTCATGTTCCAAGG<br>GAACCGCTTCAGGAACAGACAGGGAGCGCTGACCGTGTACACTGGCACCTTC<br>ACACAAGGCACCGACCCCGTCAAGACCTACTACCAGTACACTCCTGTGTCCTC<br>GCGGGCTATGTACGATGCGTACTGGAATGGGAAGTTTCGGGACTGCGCTTTC<br>CACTCCGGCTTCAACGAGGATCCATTCGTGTGCGAATATCAGGGCCAGAGCT<br>CCGACCTCCCCCAACCCCTGCAAACGCCGGCGGAGAATCCGGAGGGGGAT<br>CAGGAGGCGGAAGCGAAGGGGGTGGATCCGAAGGAGGCGGATCCGAGGGT<br>GGAGGCTCCGAAGGGGGAGGCTCTGGTGGTGGCTCCGGATCGGGA<br><br>SEQ ID NO: 45 =<br>ATGGCCGAAACCGTGGAATCATGTCTGGCGAAGCCCCATACCGAGAACTCCT<br>TCACCAACGTCTGGAAAGAGGGCGACAGCCGCTACGCCAACTACGAGGGCT<br>GCCTGTGGAACGCCGGTGGAGTGGTCGTCTGCACCGGGGATGAGACTCAGT<br>GCTACGGACACTGGGTGCCTATCGGACTGGCCATTCCCGAGAACGAGGGGG<br>GTGGTAGCGAAGGCGGCGGATCGGAAGGCGGAGGATCTGAGGGAGGGGGA<br>ACCAAGCCTCCGGAATACGGCGACACTCCGATCCCCGGGTATACGTACATCA<br>ATCCGCTGGACGGGACCTACCCGCCTGGAACTGAGCAGAACCCGGCCAACC<br>CAAACCCTAGCCTCGAGGAATCCCAGCCGTTGAACACCTTCATGTTCCAAGG<br>GAACCGCTTCAGGAACAGACAGGGAGCGCTGACCGTGTACACTGGCACCTTC<br>ACACAAGGCACCGACCCCGTCAAGACCTACTACCAGTACACTCCTGTGTCCTC<br>GCGGGCTATGTACGATGCGTACTGGAATGGGAAGTTTCGGGACTGCGCTTTC<br>CACTCCGGCTTCAACGAGGATCCATTCGTGTGCGAATATCAGGGCCAGAGCT<br>CCGACCTCCCCCAACCCCTGCAAACGCCGGCGGAGAATCCGGAGGGGGAT<br>CAGGAGGCGGAAGCGAAGGGGGTGGATCCGAAGGAGGCGGATCCGAGGGT<br>GGAGGCTCCGAAGGGGGAGGCTCTGGTGGTGGCTCCGGATCGGGAGCCAG<br>ATCTGACAAAACTCACACATGCCCACCGTGCCCAGCACCTGAACTCCTGGGG<br>GGACCGTCAGTCTTCCTCTTCCCCCCAAAACCCAAGGACACCCTCATGATCTC<br>CCGGACCCCTGAGGTCACATGCGTGGTGGTGGACGTGAGCCACGAAGACCC<br>TGAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAGG<br>TCTCCAACAAAGCCCTCCCAGCCCCCATCGAGAAAACCATCTCCAAAGCCAAA<br>GGGCAGCCCCGAGAACCACAGGTGTACACCCTGCCCCCATCCCGGGAGGAG<br>ATGACCAAGAACCAGGTCAGCCTGACCTGCCTGGTCAAAGGCTTCTATCCCA<br>GCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAA<br>GCTCACCGTGGACAAGAGCAGGTGGCAGCAGGGGAACGTCTTCTCATGCTCC<br>GTGATGCACGAGGCTCTGCACAACCACTACACGCAGAAGAGCCTCTCCCTGT<br>CTCCGGGTAAATGA<br><br>SEQ ID NO: 46 =<br>ATGGCCGAAACCGTGGAATCATGTCTGGCGAAGCCCCATACCGAGAACTCCT<br>TCACCAACGTCTGGAAAGAGGGCGACAGCCGCTACGCCAACTACGAGGGCT<br>GCCTGTGGAACGCCGGTGGAGTGGTCGTCTGCACCGGGGATGAGACTCAGT<br>GCTACGGACACTGGGTGCCTATCGGACTGGCCATTCCCGAGAACGAGGGGG<br>GTGGTAGCGAAGGCGGCGGATCGGAAGGCGGAGGATCTGAGGGAGGGGGA<br>ACCAAGCCTCCGGAATACGGCGACACTCCGATCCCCGGGTATACGTACATCA<br>ATCCGCTGGACGGGACCTACCCGCCTGGAACTGAGCAGAACCCGGCCAACC<br>CAAACCCTAGCCTCGAGGAATCCCAGCCGTTGAACACCTTCATGTTCCAAAAC<br>AACCGCTTCAGGAACGTGAACGGAGTGCTGACCGTGTACACTGGCACCTTCA<br>CACAAGGCACCGACCCCGTCAAGACCTACTACCAGTACACTCCTGTGTCCTC<br>GCGGGCTATGTACGATGCGTACTGGAATGGGAAGTTTCGGGACTGCGCTTTC<br>CACTCCGGCTTCAACGAGGATCCATTCGTGTGCGAATATCAGGGCCAGAGCT<br>CCGACCTCCCCCAACCCCTGCAAACGCCGGCGGAGAATCCGGAGGGGGAT<br>CAGGAGGCGGAAGCGAAGGGGGTGGATCCGAAGGAGGCGGATCCGAGGGT<br>GGAGGCTCCGAAGGGGGAGGCTCTGGTGGTGGCTCCGGATCGGGAGCCAG<br>ATCTGACAAAACTCACACATGCCCACCGTGCCCAGCACCTGAACTCCTGGGG<br>GGACCGTCAGTCTTCCTCTTCCCCCCAAAACCCAAGGACACCCTCATGATCTC<br>CCGGACCCCTGAGGTCACATGCGTGGTGGTGGACGTGAGCCACGAAGACCC<br>TGAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAGG<br>TCTCCAACAAAGCCCTCCCAGCCCCCATCGAGAAAACCATCTCCAAAGCCAAA<br>GGGCAGCCCCGAGAACCACAGGTGTACACCCTGCCCCCATCCCGGGAGGAG<br>ATGACCAAGAACCAGGTCAGCCTGACCTGCCTGGTCAAAGGCTTCTATCCCA<br>GCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAA<br>GCTCACCGTGGACAAGAGCAGGTGGCAGCAGGGGAACGTCTTCTCATGCTCC<br>GTGATGCACGAGGCTCTGCACAACCACTACACGCAGAAGAGCCTCTCCCTGT<br>CTCCGGGTAAATGA<br><br>SEQ ID NO: 47 =<br>ATGGCCGAAACCGTGGAATCATGTCTGGCGAAGCCCCATACCGAGAACTCCT<br>TCACCAACGTCTGGAAAGAGGGCGACAGCCGCTACGCCAACTACGAGGGCT<br>GCCTGTGGAACGCCGGTGGAGTGGTCGTCTGCACCGGGGATGAGACTCAGT<br>GCTACGGACACTGGGTGCCTATCGGACTGGCCATTCCCGAGAACGAGGGGG<br>GTGGTAGCGAAGGCGGCGGATCGGAAGGCGGAGGATCTGAGGGAGGGGGA |

| Brief Description of Sequences |
|---|
| ACCAAGCCTCCGGAATACGGCGACACTCCGATCCCCGGGTATACGTACATCA |
| ATCCGCTGGACGGGACCTACCCGCCTGGAACTGAGCAGAACCCGGCCAACC |
| CAAACCCTAGCCTCGAGGAATCCCAGCCGTTGAACACCTTCATGTTCCAAGG |
| GAACCGCTTCAGGGCTAGACAGGGAGCGCTGACCGTGTACACTGGCACCTTC |
| ACACAAGGCACCGACCCCGTCAAGACCTACTACCAGTACACTCCTGTGTCCTC |
| GCGGGCTATGTACGATGCGTACTGGAATGGGAAGTTTCGGGACTGCGCTTTC |
| CACTCCGGCTTCAACGAGGATCCATTCGTGTGCGAATATCAGGGCCAGAGCT |
| CCGACCTCCCCCAACCCCCTGCAAACGCCGGCGGAGAATCCGGAGGGGGAT |
| CAGGAGGCGGAAGCGAAGGGGGTGGATCCGAAGGAGGCGGATCCGAGGGT |
| GGAGGCTCCGAAGGGGGAGGCTCTGGTGGTGGCTCCGGATCGGGAGCCAG |
| ATCTGACAAAACTCACACATGCCCACCGTGCCCAGCACCTGAACTCCTGGGG |
| GGACCGTCAGTCTTCCTCTTCCCCCCAAAACCCAAGGACACCCTCATGATCTC |
| CCGGACCCCTGAGGTCACATGCGTGGTGGTGGACGTGAGCCACGAAGACCC |
| TGAGGTCAAGTTCAACTGGTACGTGGACGGCGTGGAGGTGCATAATGCCAAG |
| ACAAAGCCGCGGGAGGAGCAGTACAACAGCACGTACCGTGTGGTCAGCGTC |
| CTCACCGTCCTGCACCAGGACTGGCTGAATGGCAAGGAGTACAAGTGCAAGG |
| TCTCCAACAAAGCCCTCCCAGCCCCCATCGAGAAAACCATCTCCAAAGCCAAA |
| GGGCAGCCCCGAGAACCACAGGTGTACACCCTGCCCCCATCCCGGGAGGAG |
| ATGACCAAGAACCAGGTCAGCCTGACCTGCCTGGTCAAAGGCTTCTATCCCA |
| GCGACATCGCCGTGGAGTGGGAGAGCAATGGGCAGCCGGAGAACAACTACA |
| AGACCACGCCTCCCGTGCTGGACTCCGACGGCTCCTTCTTCCTCTACAGCAA |
| GCTCACCGTGGACAAGAGCAGGTGGCAGCAGGGGAACGTCTTCTCATGCTCC |
| GTGATGCACGAGGCTCTGCACAACCACTACACGCAGAAGAGCCTCTCCCTGT |
| CTCCGGGTAAATGA |
| |
| SEQ ID NO: 48 = |
| ATGGCCGAAACCGTGGAATCATGTCTGGCGAAGCCCCATACCGAGAACTCCT |
| TCACCAACGTCTGGAAAGAGGGCGACAGCCGCTACGCCAACTACGAGGGCT |
| GCCTGTGGAACGCCGGTGGAGTGGTCGTCTGCACCGGGGATGAGACTCAGT |
| GCTACGACACTGGGTGCCTATCGGACTGGCCATTCCCGAGAACGAGGGGG |
| GTGGTAGCGAAGGCGGCGGATCGGAAGGCGGAGGATCTGAGGGAGGGGGA |
| ACCAAGCCTCCGGAATACGGCGACACTCCGATCCCCGGGTATACGTACATCA |
| ATCCGCTGGACGGGACCTACCCGCCTGGAACTGAGCAGAACCCGGCCAACC |
| CAAACCCTAGCCTCGAGGAATCCCAGCCGTTGAACACCTTCATGTTCCAAAAC |
| AACCGCTTCAGGGCCGTGAACGGAGTGCTGACCGTGTACACTGGCACCTTCA |
| CACAAGGCACCGACCCCGTCAAGACCTACTACCAGTACACTCCTGTGTCCTC |
| GCGGGCTATGTACGATGCGTACTGGAATGGGAAGTTTCGGGACTGCGCTTTC |
| CACTCCGGCTTCAACGAGGATCCATTCGTGTGCGAATATCAGGGCCAGAGCT |
| CCGACCTCCCCCAACCCCCTGCAAACGCCGGCGGAGAATCCGGAGGGGGAT |
| CAGGAGGCGGAAGCGAAGGGGGTGGATCCGAAGGAGGCGGATCCGAGGGT |
| GGAGGCTCCGAAGGGGGAGGCTCTGGTGGTGGCTCCGGATCGGGAGCCAG |
| ATCTGACAAAACTCACACATGCCCACCGTGCCCAGCACCTGAACTCCTGGGG |
| GGACCGTCAGTCTTCCTCTTCCCCCCAAAACCCAAGGACACCCTCATGATCTC |
| CCGGACCCCTGAGGTCACATGCGTGGTGGTGGACGTGAGCCACGAAGACCC |
| TGAGGTCAAGTTCAACTGGTACGTGGACGGCGTGGAGGTGCATAATGCCAAG |
| ACAAAGCCGCGGGAGGAGCAGTACAACAGCACGTACCGTGTGGTCAGCGTC |
| CTCACCGTCCTGCACCAGGACTGGCTGAATGGCAAGGAGTACAAGTGCAAGG |
| TCTCCAACAAAGCCCTCCCAGCCCCCATCGAGAAAACCATCTCCAAAGCCAAA |
| GGGCAGCCCCGAGAACCACAGGTGTACACCCTGCCCCCATCCCGGGAGGAG |
| ATGACCAAGAACCAGGTCAGCCTGACCTGCCTGGTCAAAGGCTTCTATCCCA |
| GCGACATCGCCGTGGAGTGGGAGAGCAATGGGCAGCCGGAGAACAACTACA |
| AGACCACGCCTCCCGTGCTGGACTCCGACGGCTCCTTCTTCCTCTOTACAGCAA |
| GCTCACCGTGGACAAGAGCAGGTGGCAGCAGGGGAACGTCTTCTCATGCTCC |
| GTGATGCACGAGGCTCTGCACAACCACTACACGCAGAAGAGCCTCTCCCTGT |
| CTCCGGGTAAATGA |
| |
| SEQ ID NO: 49 = |
| ATGGCCGAAACCGTGGAATCATGTCTGGCGAAGCCCCATACCGAGAACTCCT |
| TCACCAACGTCTGGAAAGAGGGCGACAGCCGCTACGCCAACTACGAGGGCT |
| GCCTGTGGAACGCCGGTGGAGTGGTCGTCTGCACCGGGGATGAGCACCAGT |
| GCTACGAACTTGGGTGCCTATCGGACTGGCCATTCCCGAGAACGAGGGGG |
| GTGGTAGCGAAGGCGGCGATCGGAAGGCGGAGGATCTGAGGGAGGGGGA |
| ACCAAGCCTCCGGAATACGGCGACACTCCGATCCCCGGGTATACGTACATCA |
| ATCCGCTGGACGGGACCTACCCGCCTGGAACTGAGCAGAACCCGGCCAACC |
| CAAACCCTAGCCTCGAGGAATCCCAGCCGTTGAACACCTTCATGTTCCAAGG |
| GAACCGCTTCAGGGCTAGACAGGGAGCGCTGACCGTGTACACTGGCACCTTC |
| ACACAAGGCACCGACCCCGTCAAGACCTACTACCAGTACACTCCTGTGTCCTC |
| GCGGGCTATGTACGATGCGTACTGGAATGGGAAGTTTCGGGACTGCGCTTTC |
| CACTCCGGCTTCAACGAGGATCCATTCGTGTGCGAATATCAGGGCCAGAGCT |
| CCGACCTCCCCCAACCCCCTGCAAACGCCGGCGGAGAATCCGGAGGGGGAT |
| CAGGAGGCGGAAGCGAAGGGGGTGGATCCGAAGGAGGCGGATCCGAGGGT |
| GGAGGCTCCGAAGGGGGAGGCTCTGGTGGTGGCTCCGGATCGGGAGCCAG |
| ATCTGACAAAACTCACACATGCCCACCGTGCCCAGCACCTGAACTCCTGGGG |
| GGACCGTCAGTCTTCCTCTTCCCCCCAAAACCCAAGGACACCCTCATGATCTC |
| CCGGACCCCTGAGGTCACATGCGTGGTGGTGGACGTGAGCCACGAAGACCC |
| TGAGGTCAAGTTCAACTGGTACGTGGACGGCGTGGAGGTGCATAATGCCAAG |
| ACAAAGCCGCGGGAGGAGCAGTACAACAGCACGTACCGTGTGGTCAGCGTC |

CTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAA
GCTCACCGTGGACAAGAGCAGGTGGCAGCAGGGGAACGTCTTCTCATGCTCC
GTGATGCACGAGGCTCTGCACAACCACTACACGCAGAAGAGCCTCTCCCTGT
CTCCGGGTAAATGA\

SEQ ID NO: 50 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACCGGGGATGAGCACCAGT
GCTACGGAACTTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAAAC
AACCGCTTCAGGGCCGTGAACGGAGTGCTGACCGTGTACACTGGCACCTTCA
CACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGAGCCAG
ATCTGACAAAACTCACACATGCCCACCGTGCCCAGCACCTGAACTCCTGGGG
GGACCGTCAGTCTTCCTCTTCCCCCCAAAACCCAAGGACACCCTCATGATCTC
CCCGGACCCCTGAGGTCACATGCGTGGTGGTGGACGTGAGCCACGAAGACCC
TGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTC
CTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAA
GCTCACCGTGGACAAGAGCAGGTGGCAGCAGGGGAACGTCTTCTCATGCTCC
GTGATGCACGAGGCTCTGCACAACCACTACACGCAGAAGAGCCTCTCCCTGT
CTCCGGGTAAATGA

SEQ ID NO: 51 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGAACGCCGGTGGAGTGGTCGTCTGCACTGGGGATGAGCACCAGT
GCTACGGAACCTGGGTGCCTATCGGACTGGCCATTCCCGAGAACGAGGGGG
GTGGTAGCGAAGGCGGCGGATCGGAAGGCGGAGGATCTGAGGGAGGGGGA
ACCAAGCCTCCGGAATACGGCGACACTCCGATCCCCGGGTATACGTACATCA
ATCCGCTGGACGGGACCTACCCGCCTGGAACTGAGCAGAACCCGGCCAACC
CAAACCCTAGCCTCGAGGAATCCCAGCCGTTGAACACCTTCATGTTCCAAGG
GAACCGCTTCAGGAACAGACAGGGAGCGCTGACCGTGTACACTGGCACCTTC
ACACAAGGCACCGACCCCGTCAAGACCTACTACCAGTACACTCCTGTGTCCTC
GCGGGCTATGTACGATGCGTACTGGAATGGGAAGTTTCGGGACTGCGCTTTC
CACTCCGGCTTCAACGAGGATCCATTCGTGTGCGAATATCAGGGCCAGAGCT
CCGACCTCCCCCAACCCCCTGCAAACGCCGGCGGAGAATCCGGAGGGGGAT
CAGGAGGCGGAAGCGAAGGGGGTGGATCCGAAGGAGGCGGATCCGAGGGT
GGAGGCTCCGAAGGGGGAGGCTCTGGTGGTGGCTCCGGATCGGGAGCCAG
ATCTGACAAAACTCACACATGCCCACCGTGCCCAGCACCTGAACTCCTGGGG
GGACCGTCAGTCTTCCTCTTCCCCCCAAAACCCAAGGACACCCTCATGATCTC
CCCGGACCCCTGAGGTCACATGCGTGGTGGTGGACGTGAGCCACGAAGACCC
TGAGGTCAAGTTCAACTGGTACGTGGACGGCGTGGAGGTGCATAATGCCAAG
ACAAAGCCGCGGGAGGAGCAGTACAACAGCACGTACCGTGTGGTCAGCGTC
CTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAG
ATGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACA
AGACCACGCCTCCCGTGCTGGACTCCGACGGCTCCTTCTTCCTCTACAGCAA
GCTCACCGTGGACAAGAGCAGGTGGCAGCAGGGGAACGTCTTCTCATGCTCC
GTGATGCACGAGGCTCTGCACAACCACTACACGCAGAAGAGCCTCTCCCTGT
CTCCGGGTAAATGA

SEQ ID NO: 52 =
ATGGCCGAAACCGTGGAATCATGTCTGGCGAAGCCCCATACCGAGAACTCCT
TCACCAACGTCTGGAAAGAGGGCGACAGCCGCTACGCCAACTACGAGGGCT
GCCTGTGGGCCGCCGGTGGAGTGGTCGTCTGCACTGGGGATGAGCACCAGT
GCTACGGAACCTGGGTGCCTATCGGACTGGCCATTCCCGAGAACGAGGGGG

| Brief Description of Sequences |
|---|
| GTGGTAGCGAAGGCGGCGGATCGGAAGGCGGAGGATCTGAGGGAGGGGGA<br>ACCAAGCCTCCGGAATACGGCGACACTCCGATCCCCGGGTATACGTACATCA<br>ATCCGCTGGACGGGACCTACCCGCCTGGAACTGAGCAGAACCCGGCCAACC<br>CAAACCCTAGCCTCGAGGAATCCCAGCCGTTGAACACCTTCATGTTCCAAGG<br>GAACCGCTTCAGGAACAGACAGGGAGCGCTGACCGTGTACACTGGCACCTTC<br>ACACAAGGCACCGACCCCGTCAAGACCTACTACCAGTACACTCCTGTGTCCTC<br>GCGGGCTATGTACGATGCGTACTGGAATGGGAAGTTTCGGGACTGCGCTTTC<br>CACTCCGGCTTCAACGAGGATCCATTCGTGTGCGAATATCAGGGCCAGAGCT<br>CCGACCTCCCCCAACCCCCTGCAAACGCCGGCGGAGAATCCGGAGGGGGAT<br>CAGGAGGCGGAAGCGAAGGGGGTGGATCCGAAGGAGGCGGATCCGAGGGT<br>GGAGGCTCCGAAGGGGGAGGCTCTGGTGGTGGCTCCGGATCGGGAGCCAG<br>ATCTGACAAAACTCACACATGCCCACCGTGCCCAGCACCTGAACTCCTGGGG<br>GGACCGTCAGTCTTCCTCTTCCCCCAAAACCCAAGGACACCCTCATGATCTC<br>CCGGACCCCTGAGGTCACATGCGTGGTGGTGGACGTGAGCCACGAAGACCC<br>TGAGGTCAAGTTCAACTGGTACGTGGACGGCGTGGAGGTGCATAATGCCAAG<br>ACAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAAGG<br>TCTCCAACAAAGCCCTCCCAGCCCCATCGAGAAAACCATCTCCAAAGCCAAA<br>GGGCAGCCCCGAGAACCACAGGTGTACACCCTGCCCCCATCCCGGGAGGAG<br>ATGACCAAGAACCAGGTCAGCCTGACCTGCCTGGTCAAAGGCTTCTATCCCA<br>GCGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGCAA<br>GCTCACCGTGGACAAGAGCAGGTGGCAGCAGGGGAACGTCTTCTCATGCTCC<br>GTGATGCACGAGGCTCTGCACAACCACTACACGCAGAAGAGCCTCTCCCTGT<br>CTCCGGGTAAATGA |
| SEQ ID NO: 53 = HHHHHH; |
| SEQ ID NO: 54 = EDGS |

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them. The articles "a" and "an" refer to one or to more than one (i.e., to at least one) of the grammatical object of the article. The term "or" means, and is used interchangeably with, the term "and/or," unless context clearly indicates otherwise. In this application, the use of the singular includes the plural unless specifically stated otherwise. Furthermore, the use of the term "comprising," as well as other forms, such as "comprises" and "comprised," are not limiting. Any range described herein will be understood to include the endpoints and all values between the endpoints.

The term "g3p" when used alone or in terms such as "g3p-derived" or "g3p fusion" refers to any wild type or recombinant filamentous phage g3p protein, including fragments, variants, and mutants of g3p that retain the ability to bind to amyloid. These terms should not be construed as limited to any particular filamentous bacteriophage g3p.

The terms "filamentous bacteriophage," "bacteriophage," and "phage" are used interchangeably herein and include both wild type and recombinant filamentous bacteriophage.

The term "wild type filamentous bacteriophage" as used herein refers to filamentous bacteriophage found in nature, filamentous bacteriophage that have been indicated as "wild type" in any nucleotide or amino acid sequence database, filamentous bacteriophage that are commercially available and characterized as "wild type," and filamentous bacteriophage that have acquired non-recombinant mutations relative to any of the foregoing through passaging.

As used herein, the term "domain" means a region of a polypeptide or protein having some distinctive physical feature or distinctive role, including, for example, an independently folded structure composed of a section of a polypeptide chain. A domain may contain the sequence of the distinctive physical feature of the polypeptide or it may contain a fragment of the physical feature that retains its binding characteristics (e.g., it retains the ability to bind to a second domain). A domain may be associated with another domain. For example, the g3p N2 domain binds F-pili and the g3p N1 domain binds TolA.

As used herein, "general amyloid interaction motif" or "GAIM" refers to a two-domain polypeptide (N1 and N2 domains of g3p) that mediates amyloid binding using a combination of both hydrophobic and polar residues lining the inner surfaces of the molecule. The N1 and the N2 domains of the GAIM monomer have an asymmetric distribution of aromatic amino acids. The GAIM N2 domain contains 11 Tyrosine (Tyr) residues and 1 exposed Tryptophan (Trp) residue; the N1 domain contains 3 Trp and 3 Tyr residues. The N1 and N2 domains adopt an inverted horseshoe conformation and are held together in a closed conformation (locked conformation) by an intricate network of hydrogen bonds (Weininger et al., 2009). A cis-trans isomerization of the prolines in the inter-domain linker leads to progressive breakage of the hydrogen-bonds and partial opening of the two domains. The "opening" rearrangement of the N1 and N2 domains of GAIM exposes β-strands 4 and 5 of N1 (comprising polar residues) and β-strands 9 and 10 of N2 (comprising aromatic/hydrophobic residues) and allows for binding to amyloid. See FIG. 1A.

As used herein, "control scaffold" or "GAIM scaffold" corresponds to the GAIM-Ig fusion protein PB120, having the amino acid sequence of SEQ ID NO:11. The GAIM portion of the GAIM scaffold has the amino acid sequence of SEQ ID NO:12. PB120 is derived from PB106, having the amino acid sequence of SEQ ID NO:13. The GAIM portion of PB106 has the amino acid sequence of SEQ ID NO:14.

As used herein, "PB106+EDGS" ("EDGS" disclosed as SEQ ID NO:54) represents an open-conformation polypeptide having the amino acid sequence as provided by SEQ ID NO:15. The GAIM portion of "PB106+EDGS" ("EDGS" disclosed as SEQ ID NO:54) has the amino acid sequence of SEQ ID NO:16.

As used herein, "super-stabilized" GAIM or GAIM fusion refers to the GAIM-Ig fusion PB113, having the amino acid sequence of SEQ ID NO:17. The GAIM portion of PB113 has the amino acid sequence of SEQ ID NO:18.

The terms "GAIM-Ig fusion," "GAIM-Ig fusion protein," and "GAIM fusion" are herein used interchangeably and refer to a polypeptide comprising a g3p GAIM domains connected directly to or through a small linker to an immunoglobulin constant region. As shown in FIG. 1B, the Fc region of the GAIM-Ig fusions of the invention dimerize, resulting in a complex that comprises two copies of GAIM attached directly or through a small linker to an immunoglobulin constant region. A GAIM fusion of the invention may further comprising a signal sequence. The present invention contemplates GAIM fusions with any immunoglobulin constant region, for example, the immunoglobulin constant region of IgG (e.g., IgG1, IgG2, IgG3, or IgG4), IgD, IgA, IgE, or IgM. In some aspects, the GAIM-Ig fusion is an open-stabilized GAIM-Ig fusion. In some aspects, the GAIM-Ig fusion is partially or fully deimmunized.

"GAIM dimer." as used herein, refers to the two GAIM domains of a GAIM-Ig fusion described herein. A GAIM dimer is graphically represented by FIG. 1C.

The terms "open-stabilized fusion," "open-stabilized GAIM-Ig fusion," "open-stabilized variant," and "open-stabilized GAIM-Ig variant" are used interchangeably herein and refer to a GAIM-Ig fusion comprising at least one open conformation mutation and at least one stabilizing mutation in the GAIM portion of the fusion. The open-conformation mutation of the open-stabilized variants described herein is a substitution of SEQ ID NO:3 (DDKTLD; amino acids 24-29 relative to SEQ ID NO:13 and SEQ ID NO:15) with SEQ ID NO:4 (EGDS). A stabilizing mutation may be an N2-stabilizing mutation, for example, selected from substitution of SEQ ID NO:5 (FQNN; amino acids 137-140 relative to SEQ ID NO:13; amino acids 135-138 relative to SEQ ID NO:15) with SEQ ID NO:8 (FQGN), substitution of SEQ ID NO:6 (RQGA; amino acids 145-148 relative to SEQ ID NO:13; amino acids 143-146 relative to SEQ ID NO:15) with SEQ ID NO:9 (VNGV), substitution of SEQ ID NO:7 (QGTDPVK; amino acids 158-164 relative to SEQ ID NO:13; amino acids 156-162 relative to SEQ ID NO:15) to SEQ ID NO:10 (QGGK), or a combination thereof. Other N2-stabilizing mutations are described below. Open-stabilized fusions as described herein may further comprise one or more substitutions, insertions, or deletions. For example, an open-stabilized GAIM-Ig fusion may be further modified to reduce or eliminate immunogenicity, to remove a potential glycosylation site, or to further modulate binding activity or specificity to amyloid protein.

As used herein, a GAIM-Ig fusion protein of the invention that "consists essentially" of a given amino acid sequence may further include a small linker connecting the GAIM domain and Fc domain of the fusion, an N-terminal signal sequence or a fragment thereof, a deletion of the N-terminal methionine (ΔM1) or a deletion of both the N-terminal methionine and alanine (ΔM1 and ΔA2), and/or a deletion of the C-terminal lysine (K) of the Fc domain of the fusion.

As used herein, a "small linker" refers to a peptide linker up to 25 amino acids in length, which connects the GAIM domain and the Fc domain of a GAIM-Ig fusion. As described further below, an exemplary "small linker" connecting the GAIM and Fc domains of a GAIM-Ig fusion may comprise a GS-rich sequence or may comprise the amino acid sequence ARS.

As used herein, a "signal sequence" refers to a short peptide of approximately 16 to 30 amino acids present at the N-terminus of a polypeptide of the invention. For example, the signal sequence may comprise the 18-amino acid N-terminal sequence of GenBank Ref Seq NP_510891.1. A signal sequence is used by a eukaryotic cell to secrete a polypeptide of the invention. It is typically cleaved from the polypeptide prior to secretion and therefore is typically absent in the secreted polypeptide.

The term "amyloid" or "amyloid fiber" is used herein as a generic term for a tertiary structure that is formed by misfolding or aggregation of any of several different proteins and that comprises an ordered arrangement of β-sheets stacked perpendicular to a fiber axis. Sunde et al., J. Mol Biol. (1997) 273:729-39.

Amyloid, as used herein, can be formed from any of the following proteins: Androgen receptor; apolipoprotein AI; apolipoprotein AII; apolipoprotein AIV; aposerum amyloid A; Aβ; ABri; ADan; Atrophin-1; atrial natriureticfactor; ataxin; calcitonin; γ-crystallin; cystatin C; fibrinogen; gelsolin; huntingtin; insulin; islet amyloid polypeptide; immunoglobulin kappa light chain; immunoglobulin lambda light chain; kerato-epithelin; keratin; lactahedrin; lactoferrin; lysozyme; lung surfactant protein C; medin; odontogenic ameloblast-associated protein; prion protein: procalcitonin; prolactin; semenogelin I; serum amyloid A; superoxide dismutase I; β2-microglobulin; TATA box binding protein; tau; transthyretin; and α-synuclein, or to a combination of the above. Amyloid, as used herein, can also be formed from truncated or post-translationally modified forms of any of the above proteins. "Amyloid" or "amyloid fiber" includes different or multiple conformations or morphologies of amyloid.

As used herein, "toxic oligomer" refers to a small assembly or aggregate of monomers that is typically on-pathway for formation of amyloid.

Exemplary amyloid includes amyloid-β aggregates formed in Alzheimer's disease, which comprises beta-amyloid peptide "Aβ," 39-43 amino acid internal fragments cleaved from the human amyloid precursor protein (hAPP). Aβ includes truncated and post-translationally modified forms. For example, Aβ40 is a short form of Aβ, and the more fibrillogenic isoform Aβ42 is a long form. Further examples of Aβ include, but are not limited to, N-truncated Aβ11-42, Aβ11-42-Pyro, Aβ3-42-Pyro, and Aβ1-42-E22Q-Dutch mutation. See Levy et al, 1990; Van Broeckhoven et al, 1990. Other exemplary amyloid proteins include α-synuclein (associated with Parkinson's disease), huntingtin (associated with Huntington's disease), tau (associated with Alzheimer's Disease), the abnormal conformation of the prion protein, PrP$^{Sc}$, and amyloid associated with various amyloidosis diseases, including but not limited to: immunoglobulin light chain (kappa or lambda), transthyretin, gelsolin, and islet amyloid polypeptide. Additional examples are provided throughout the description and are known to those of skill in the art (see, e.g., Aguzzi (2010), and Eichner and Radford, Mol. Cell (2011) 43.8-18). Unless a protein or peptide is specified, use of the terms "amyloid" or "amyloid fibers" should not be construed as limited to any particular protein, morphology, disease, or condition.

The term "beta amyloid peptide" is synonymous with "β-amyloid peptide," βAP," "βA," and "Aβ." All of these terms refer to an amyloid forming peptide derived from the human amyloid precursor protein (hAPP).

As used herein, "PrP protein," "PrP," and "prion," refer to polypeptides that are capable under appropriate conditions of inducing the formation of aggregates responsible for protein misfolding diseases. For example, normal cellular prion protein ($PrP^c$) is converted under appropriate conditions into the corresponding scrapie isoform ($PrP^{Sc}$) that is responsible for diseases such as, but not limited to, bovine spongiform encephalopathy (BSE) (mad cow disease), feline spongiform encephalopathy of cats, kuru, Creutzfeldt-Jakob Disease (CJD), Gerstmann-Straussler-Scheinker disease (GSS), and fatal familial insomnia (FFI).

As used herein, a "disease associated with misfolded and/or aggregated amyloid protein" includes but is not limited to Alzheimer's disease; early onset Alzheimer's disease; late onset Alzheimer's disease; presymptomatic Alzheimer's disease; AL amyloidosis; amyotrophic lateral sclerosis (ALS); Amyotrophic lateral sclerosis/parkinsonism-dementia complex: Argyrophilic grain dementia; Aortic medial amyloidosis; ApoAI amyloidosis; ApoAII amyloidosis; ApoAIV amyloidosis; Atrial amyloidosis; British/Danish dementia; Cataract; Corticobasal degeneration; Corneal amyloidosis associated with trichiasis; cystatin C plaque-related disease; cystatin C plaque-related coronary disease; cystatin C plaque-related kidney disease; cutaneous lichen amyloidosis; Dementia pugilistica; dentatorubral-pallidoluysian atrophy; diffuse neurofibrillary tangles with calcification; dementia with Lewy bodies; Down's syndrome; Familial Amyloidotic Cardiomyopathy (FAC); Familial Amyloidotic Polyneuropathy (FAP); Familial British dementia; Familia Danish dementia; familial encephalopathy; Familial Mediterranean fever; Fibrinogen amyloidosis; Finnish hereditary amyloidosis; Frontotemporal dementia with Parkinsonism; frontotemporal lobar degeneration (FTLDs); frontotemporal lobe dementia; Hallervorden-Spatz disease; Hemodialysis-related amyloidosis; hereditary cerebral amyloid angiopathy; hereditary cerebral hemorrhage with amyloidosis; hereditary lattice corneal dystrophy; Huntington's disease; Icelandic hereditary cerebral amyloid angiopathy; Inclusion-body myositis; Injection-localized amyloidosis; islet amyloid polypeptide amyloidosis; Lysozyme amyloidosis; multiple myeloma; Myotonic dystrophy; Niemann-Pick disease type C; Non-Guamanian motor neuron disease with neurofibrillary tangles; Parkinson's disease; peripheral amyloidosis; Pick's disease; Pituitary prolactinoma; Postencephalitic parkinsonism; Prion protein cerebral amyloid angiopathy; prion-mediated disease; kuru; Creutzfeldt-Jakob disease (CJD); Gerstmann-Straussler-Scheinker disease (GSS); fatal familial insomnia (FFI); scrapie; spongiform encephalopathy; pulmonary alveolar proteinosis; Progressive subcortical gliosis; Progressive supranuclear palsy; Senile Systemic Amyloidosis; serum AA amyloidosis; spinal and bulbar muscular atrophy: spinocerebellar ataxia (SCA1, SCA3, SCA6, or SCA7); Subacute sclerosing panencephalitis; systemic amyloidosis; familial amyloidosis; wild-type amyloidosis; Tangle only dementia; and Tauopathies. See, for example, Chiti & Dobson, Annu Rev Biochem (2006) 75:333-66; and Josephs et al., Acta Neuropathol (2011) 122:137-153. There is a great need to prevent and/or reduce amyloid aggregate formation (i.e., misfolded and/or aggregated proteins) to treat or reduce the symptoms or severity of these diseases.

As used herein, a polypeptide, composition, formulation, or nucleic acid that "reduces amyloid" does one or more of the following: inhibits amyloid formation, causes amyloid disaggregation, causes amyloid remodeling, promotes amyloid clearance, inhibits amyloid aggregation, blocks and/or prevents the formation of toxic oligomers, and/or promotes the clearance of toxic oligomers.

Polypeptides, nucleic acids or compositions of the invention or described as "disaggregating" or "mediating disaggregation" reduce aggregates that have already formed. Disaggregation can be measured by the filter trap assay (Wanker et al., Methods Enzymol (1999) 309:375-86) or other methods known in the art. The filter trap assay can be used both to detect aggregates and to monitor disaggregation mediated by compositions of the invention. Disaggregation is detected as decreased retention of amyloid on the filter, as shown by a decrease in staining, in the presence of increasing concentrations of the disaggregating agent.

Polypeptides, nucleic acids, or compositions of the invention described as "protecting neurons from amyloid damage" prevent the accumulation of new amyloid and/or prevent the formation of toxic oligomers. Products or compositions of the invention described as "protecting neurons from amyloid damage" may be taken prophylactically. Whether or not a product or composition protects neurons from amyloid damage may be measured by a neuronal cell culture cytotoxicity assay as described in WO 2014/055515, hereby incorporated by reference in its entirety.

Polypeptides, nucleic acids, or compositions of the invention described as "remodeling" amyloid cause partial or complete transformation of fibrillar conformers into amorphous aggregates. Remodeling may be measured through denaturation studies using urea (e.g., for forms of Aβ) or a sarkosyl solubility assay (e.g., for forms of tau). Increased remodeling may be detected by the loss or failure of amyloid to bind Thioflavin T (ThT), resulting in reduced ThT fluorescence. Remodeling may also be detected using transmission electron microscopy (TEM).

Polypeptides, nucleic acids, or compositions of the invention described as "inhibiting amyloid aggregation" partially or completely prevent aggregation of amyloid. Inhibition of amyloid aggregation may be measured by a ThT fluorescence assay (e.g., lower fluorescence indicating a lower percentage of amyloid aggregation).

The term "variant" as used herein in conjunction with a bacteriophage, protein, polypeptide, or amino acid sequence (e.g., a GAIM variant), refers to a corresponding substance that contains at least one amino acid difference (at least one mutation, being a substitution, insertion, or deletion) as compared to the reference substance. In certain embodiments, a "variant" has high amino acid sequence homology and/or conservative amino acid substitutions, deletions, and/or insertions as compared to the reference sequence. In some embodiments, a variant has no more than 25, 20, 17, 15, 12, 10, 9, 8, 7, 6, 5, 4, 3, 2, or 1 amino acid differences as compared to the reference sequence. A variant as described herein may preserve or increase: amyloid-binding activity, amyloid-binding specificity, and/or protein quality as compared to the reference sequence. A variant as described herein may be deglycosylated. A variant as described herein may reduce or eliminate immunogenicity.

A "conservative substitution" refers to the replacement of a first amino acid by a second amino acid that does not substantially alter the chemical, physical and/or functional properties of the g3p protein or amyloid binding fragment of g3p (e.g., the g3p protein or amyloid binding fragment retains the same charge, structure, polarity, hydrophobicity/hydrophilicity, and/or preserves functions such as the ability to recognize, bind to, and/or reduce amyloid). Such conservative amino acid modifications are based on the relative similarity of the amino acid side-chain substituents, for example, their hydrophobicity, hydrophilicity, charge, size, and the like. Exemplary sets of amino acids which are interchangeable as conservative substitutions, and which take various of the foregoing characteristics into consideration, are well known to those of skill in the art and include: arginine and lysine; glutamate and aspartate; serine and threonine; glutamine and asparagine; and valine, leucine, and isoleucine.

The term "immunogenic" or "immunogenicity" is used herein to refer to the ability of a composition to elicit an immune response in a mammal that has been exposed to the composition. In some aspects, the present invention relates to polypeptides or compositions with reduced immunogenicity or that are fully deimmunized. Full deimmunization indicates the removal of all five of the T-cell recognition epitopes present in the native GAIM amino acid sequence by one or more mutations in those epitopic sequences. Such deimmunizing mutations may constitute a substitution, insertion, or deletion of one or more amino acid residues in an epitope, or may constitute partially or fully deleting the epitopic sequence.

General Amyloid Interaction Motif (GAIM) of G3p and GAIM-Ig Fusions Thereof

The general amyloid interaction motif (GAIM) is a two-domain polypeptide comprising the N1 and N2 domains of g3p. The GAIM N2 domain consists of three distinct structural elements: a globular part resembling N1 in structure (Holliger et al. (1999) J Mol Biol, 288:649-57), an alpha-helix, and a disordered region that forms an extensive network of H-bonds with the N1 domain. The N2 hinge region also contains several proline residues, one of which (P213) has been implicated in maintaining GAIM in an open, TolA binding-competent state. The N1 and the N2 domains of the GAIM monomer have an asymmetric distribution of aromatic amino acids. The GAIM N2 domain contains 11 Tyrosine (Tyr) residues and 1 exposed Tryptophan (Trp) residue; the N1 domain contains 3 Trp and 3 Tyr residues. Thus, the intrinsic fluorescence of tyrosine and tryptophan residues allow specific monitoring of conformational changes in N2 and N1 domains, respectively (Martin and Schmid (2003) J Mol Biol, 405:989-1003), allowing for detection of an open conformation of GAIM.

H/D exchange studies show that GAIM binds to the central core of Aβ42 fibers. As demonstrated by FIG. 2, H/D exchange studies also show that GAIM engages discontinuous sequences on the fibril-core and binds both sequences rich in aromatic residues (e.g., residues 17-25 in Aβ42) and aliphatic residues (e.g., residues 31-40 in Aβ42). This results in robust inhibition of amyloid assembly and efficient remodeling of fibers into amorphous aggregates (Krishnan et al. (2014) J Mol Biol, 426:2500-19).

In some aspects, a polypeptide or composition comprising the polypeptide comprises a GAIM variant. In some embodiments, a GAIM variant has no more than 25 amino acid differences as compared to the reference sequence. In some embodiments, a GAIM variant has no more than 17 amino acid differences as compared to the reference sequence. In some embodiments, a GAIM variant has no more than 10 amino acid differences as compared to the reference sequence. In some embodiments, a variant has no more than 7 amino acid differences as compared to the reference sequence. In some embodiments, the reference sequence is SEQ ID NO:12 (GAIM portion of PB120). In some embodiments, the reference sequence is SEQ ID NO:14 (GAIM portion of PB106). In some embodiments, the reference sequence is SEQ ID NO:16 (GAIM portion of "PB106+EDGS" ("EDGS" disclosed as SEQ ID NO:54)).

Unless otherwise specified, all GAIM amino acid sequence numbering is based on the amino acid sequence of SEQ ID NO:16 and all GAIM-Ig amino acid sequence numbering is based on the amino acid sequence of SEQ ID NO:15, which constitutes SEQ ID NO:16 fused at the C-terminal end to a human IgG1-Fc amino acid sequence by the short linker ARS.

Polypeptides of the invention comprise any of the GAIM variants described herein. The GAIM variants disclosed herein comprise a substitution of SEQ ID NO:3 (DDKTLD; amino acids 24-29 relative to SEQ ID NO:13) with SEQ ID NO:4 (EGDS). This substitution is present in reference sequence SEQ ID NO: 16 and results in the GAIM variants of the invention having an open-conformation ("open" or "unlocked") GAIM variant.

The GAIM variants of the invention also include at least one additional set of amino acid changes selected from (i) alternative T-cell epitope 1-deimmunizing changes, (ii) T-cell epitope 2-deimmunizing changes, and (iii) N2-stabilizing changes.

In some embodiments, the at least one other set of amino acid changes increases amyloid affinity while still being deimmunized in T-cell epitope 1. In reference SEQ ID NO:16, deimmunized T-cell epitope 1 spans from amino acids G47 to H55. The H55 in that sequence causes the deimmunization; wild-type g3p (in which T-cell epitope 1 is not deimmunized) has a threonine at the corresponding position. Although amyloid affinity remains significant for g3p polypeptide variants comprising the threonine-to-histidine change at amino acid 55 of SEQ ID NO:16, this affinity is somewhat reduced relative to wild-type. Interestingly, it has been reported that that the sequence YGT, which is present in native g3p, is a TolA binding motif (S Pommier et al, J. Bacteriol. (2005), 187 (21), pp. 7526-34). Without being bound by theory, we believe that GAIM-amyloid binding may require similar amino acid interactions as g3p-TolA binding. Thus, we explored regenerating the 53YGT55 sequence in SEQ ID NO:16 by making a H55T substitution (e.g., reverting to the wild-type T-cell epitope 1 sequence) and looking for an alternative substitution in the now-regenerated T-cell epitope that would affect deimmunization. We found that a T50 substitution causes deimmunization of T-cell epitope 1 without affecting amyloid affinity. Therefore, in some embodiments, a GAIM variant of the invention comprises a T50 substitution accompanied by a H55T substitution. In some aspects of these embodiments, the T50 substitution is T50R, T50K, T50G, or T50H. In at least one aspect of these embodiments, the T50 substitution is T50H.

In some embodiments, the at least one other set of amino acid changes deimmunizes T-cell epitope 2 without significantly altering amyloid affinity. In reference SEQ ID NO:16, T-cell epitope 2 spans from amino acid M134 to N142 (see U.S. Pat. No. 9,988,444 B2 and U.S. Patent Publication US 2018/0207231 A1, each incorporated by reference in its entirety), and is unchanged as compared to the corresponding wild-type g3p sequence. Prior to the present invention, we have been unable to deimmunize this epitope without significant reduction in amyloid binding and/or significant decrease in the stability of the resulting GAIM. We have now discovered that substitution of N142 and/or N137 with another amino acid deimmunizes T-cell epitope 2 without significant effect on amyloid binding or stability. Thus, in some embodiments, a GAIM variant of the invention comprises a substitution of N142. In some aspects of these embodiments, the N142 substitution is N142A. In alternate embodiments, a GAIM variant of the invention comprises a substitution of N137. In some aspects of these embodiments, the N137 substitution is N137G. In other alternate embodiments, a GAIM variant of the invention comprises a substitution of N137 and a substitution of N142. In some aspects of these embodiments, the N137 substitution is N137G and the N142 substitution is N142A.

Figures 3A, 3B:
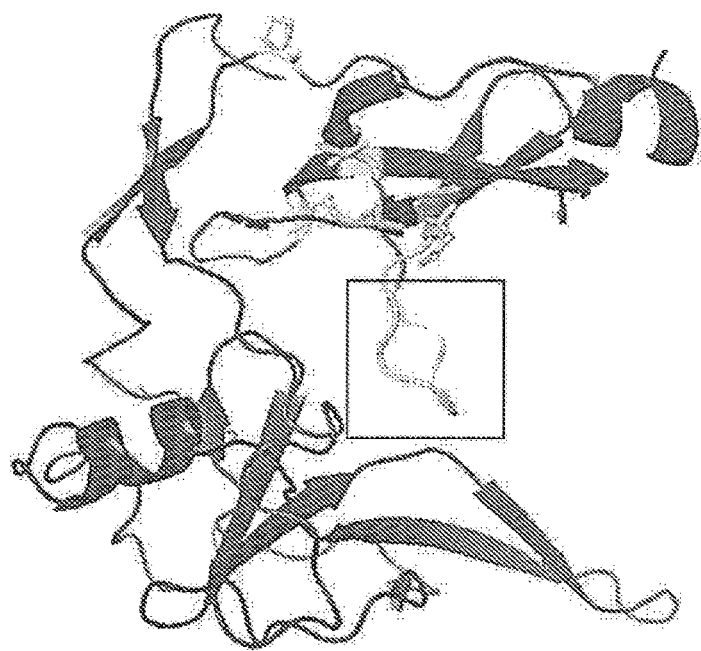
FIG. 3A compares corresponding portions of the amino acid sequence of the N1 portion of g3p from fd phage (SEQ ID NO:1) and the corresponding N1 portion of g3p from IF1 phage (SEQ ID NO:2). The open box depicts, on top, the amino acids 23-28 (DDKTLD; SEQ ID NO:3) of PB106 and the GAIM scaffold PB120 (derived from PB106) and, on bottom, the EGDS (SEQ ID NO: 4) substitution present in the open-stabilized GAIM-Ig fusions of the invention (EGDS=SEQ ID NO:4).
FIG. 3B is a graphical representation of the tertiary structure of the GAIM N1 and N2 domains (shown using PDB structure 2G3P). The open box in FIG. 3B shows the location of SEQ ID NO:3 in fd g3p.
Figure 3C:
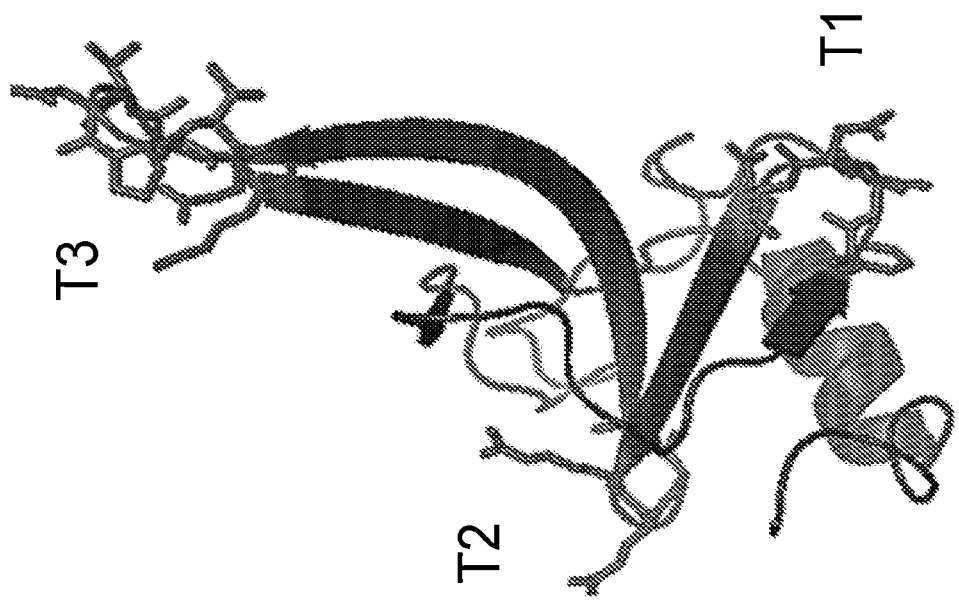
FIG. 3C is a graphical representation of three slow-folding loops (also referred to as "turns") implicated in stabilization of the N2 domain. T1=Turn 1 (FQNN; SEQ ID NO: 5); T2=Turn 2 (RQGA; SEQ ID NO: 6); T3=Turn 3 (QGTDPVK; SEQ ID NO: 7). As demonstrated below, removing one or more of T1, T2, or T3 by mutagenesis stabilizes the N2 domain.
Figure 3D:
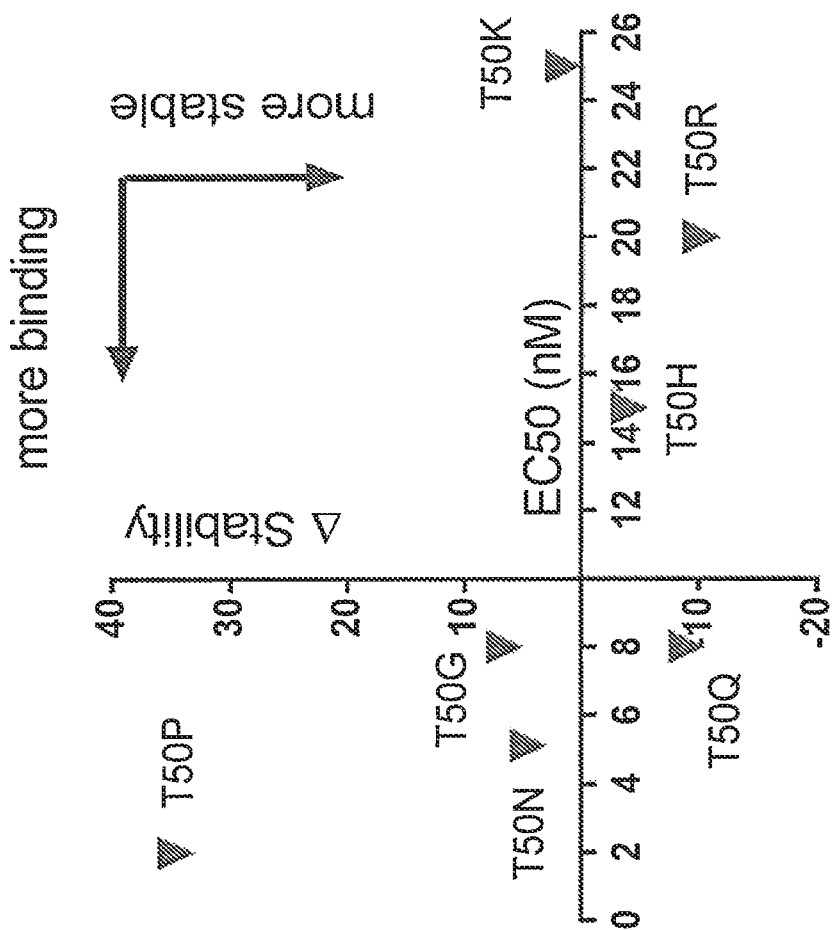
FIG. 3D depicts changes in binding and stability based on select amino acid substitutions of T50.

In some embodiments, the at least one other set of amino acid changes increases the stability of N2. These changes target one or more of the so-called slow folding loops present in SEQ ID NO:16, which span amino acids 135-138 (FQNN: SEQ ID NO:5; Turn 1), 143-146 (RQGA; SEQ ID NO.6, Turn 2), and 156-162 (QGTDPVK; SEQ ID NO:7; Turn 3), as depicted by FIG. 3C. We have discovered that certain amino acid substitutions and/or deletions in one or more of these regions will increase the stability of N2 in a GAIM. Thus, in some embodiments, at least one other set of amino acid changes is selected from: (i) N137G: (ii) R143V, Q144N, and, optionally, A146V, A146T, or A146K; and (iii) V161G, deletion of T158, D159, and P160, optionally, Q156V or Q156Y, and, optionally, G157N. As provided above, the N137G substitution that stabilizes N2 by removing the slow-folding loop at Turn 1 also deimmunizes T-cell epitope 2. In some aspects of these embodiments, the GAIM variant comprises amino acid changes in only one of Turn 1, Turn 2, and Turn 3, e.g., one of: (i) N137G; (ii) R143V, Q144N, and, optionally, A146V, A146T, or A146K; and (iii) V161G, deletion of T158, D159, and P160, optionally, Q156V or Q156Y, and, optionally, G157N. In some aspects of these embodiments, the GAIM variant comprises amino acid changes in at least two of the turns, e.g., two of (i) N137G; (ii) R143V, Q144N, and, optionally, A146V, A146T, or A146K; and (iii) V161G, deletion of T158, D159, and P160, optionally, Q156V or Q156Y, and, optionally, G157N. In some aspects of these embodiments, the amino acid change is N137G, resulting in SEQ ID NO:8 at amino acids 135-138. In some aspects of these embodiments, the amino acid change is R143V, Q144N, and A146V, resulting in SEQ ID NO:9 at amino acids 143-146. In some aspects of these embodiments, the amino acid change is deletion of T158, D159, and P160, and the substitution V161G, resulting in SEQ ID NO:10 as a replacement for amino acids 156-162. In at least one aspect of these embodiments, the GAIM variant does not comprise amino acid changes in all three of the turns.

In some embodiments, a polypeptide of the invention comprises a GAIM variant having at least one set of amino acid changes selected from any of the above-described alternative T-cell epitope 1-deimmunizing changes and at least one set of amino acid changes selected from any of the above-described T-cell epitope 2-deimmunizing changes.

In some embodiments, the GAIM variants has at least one set of amino acid changes selected from any of the above-described alternative T-cell epitope 1-deimmunizing changes and at least one set of amino acid changes selected from any of the above-described N2-stabilizing changes.

In some embodiments, the GAIM variant has at least one set of amino acid changes selected from any of the above-described T-cell epitope 2-deimmunizing changes and at least one set of amino acid changes selected from any of the above-described N2-stabilizing changes.

In some embodiments, the GAIM variant has at least one set of amino acid changes selected from any of the above-described alternative T-cell epitope 1-deimmunizing changes, at least one set of amino acid changes selected from any of the above-described T-cell epitope 2-deimmunizing changes, and at least one set of amino acid changes selected from any of the above-described N2-stabilizing changes.

The choice of the specific set of amino acid changes for each of the aforementioned types of changes can be made from any of the changes described herein for that given type. Non-limiting examples of sets of amino acid changes can be found in Table 1.

TABLE 1

Mutations of Open-Stabilized GAIM-Ig Fusion Relative to SEQ ID NO: 16

| GAIM-Ig Fusion Protein | SEQ ID NO: | T-cell Epitope 1 Mutation(s)* | T-cell Epitope 2 Mutation(s) | N2-stabilizing Mutation(s) | Glycosylation Signal Mutation(s)*** |
|---|---|---|---|---|---|
| PB108 | 29 | None | N137G** | N137G | None |
| PB122 | 30 | None | None | R143V Q144N A146V | None |
| PB116 | 31 | None | N137G N142A | N137G | None |
| PB114 | 32 | None | N142A | R143V Q144N A146V | None |
| PB109 | 33 | T50H H55T | N137G N142A | N137G | None |
| PB110 | 34 | T50H H55T | N142A | R143V Q144N A146V | None |
| PB105 | 35 | T50H H55T | N137G | N137G | None |
| PB127 | 36 | T50H H55T | N137G | N137G | N38A |

*T-cell epitope 1 of SEQ ID NO: 16 is deimmunized by a T55H substitution relative to wild-type g3p. Mutations in T-cell epitope 1 in the open-stabilized GAIM-Ig fusions represent alternative deimmunizing substitutions.
**The N137G substitution deimmunizes T-cell epitope 2 and stabilizes the N2 domain.
***SEQ ID NO: 16 is deglycosylated by a T40G mutation relative to wild-type g3p. Mutations in the potential glycosylation signal in the open-stabilized GAIM-Ig fusions represent additional deglycosylating substitutions.

The polypeptides of the invention comprise a deglycosylated GAIM variant. The reference sequence SEQ ID NO:16 is deglycosylated because it comprises a T40G mutation relative to wild-type g3p, thus altering the native NAT glycosylation signal to NAG. Examples of other deglycosylated g3p mutants and/or variants can be found in U.S. Patent Publication US 2018/0207231 A1. However, GAIM variants that have different and/or additional deglycosylating mutations in the native glycosylation signal are also part of the present invention. For example, the three amino acid sequence NX(T/S), where X is any amino acid, is a known glycosylation signal. Substitution of the asparagine (N) in such a sequence with any amino acid other than cysteine will destroy the glycosylation signal. Similarly, substitution of threonine (T) or serine (S) in such a sequence with any amino acid other than cysteine will destroy the glycosylation signal.

Thus, in some embodiments, a GAIM variant described herein comprises a substitution of N38 with any amino acid other than cysteine as compared to SEQ ID NO:16, and further comprises one or more of an alternative T-cell epitope 1-deimmunizing change, a T-cell epitope 2-deimmunizing change, and/or an N2-stabilizing change. In some aspects of these embodiments, the substitution of N38 is N38A. In some aspects of these embodiments, the GAIM variant further comprises a substitution of G40 to any amino acid other than cysteine.

In some alternate embodiments, a GAIM variant described herein comprises a substitution of G40 with any amino acid other than cysteine, threonine, or serine as compared to SEQ ID NO:16, and further comprises one or more of a T-cell epitope 1-deimmunizing change, a T-cell epitope 2-deimmunizing change, and/or an N2-stabilizing change.

SEQ ID NO:16 includes the N-terminal amino acids M1 and A2. Recombinant production of GAIM in animal cell lines can result in polypeptides that are missing M1 or both M1 and A2 (an "N-terminal truncation"). Such N-terminal truncations do not affect amyloid-binding activity. Thus, in some embodiments, a GAIM variant optionally lacks amino acid 1 (ΔM1) or both amino acids 1 and 2 (ΔM1 and ΔA2) of SEQ ID NO:16, in addition to comprising one or more of a T-cell epitope 1-deimmunizing change, a T-cell epitope 2-deimmunizing change, and/or an N2-stabilizing change. As used herein, a GAIM variant lacking amino acid 1 or both amino acid 1 or 2 may refer to an N-terminal truncation (i.e., removal after translation) or a deletion mutation.

In some embodiments, the GAIM variant is a variant of SEQ ID NO:16 comprising the substitution N137G. In some aspects of these embodiments, the GAIM variant lacks amino acid 1 (e.g., ΔM1). In some aspects of these embodiments, the GAIM variant lacks amino acids 1 and 2 (e.g., ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In some embodiments, the GAIM variant is a variant of SEQ ID NO:16 comprising R143V, Q144N, and, optionally, A146V, A146T, or A146K. In certain embodiments, the GAIM variant is a variant of SEQ ID NO:16 comprising R143V, Q144N, and A146V. In some aspects of these embodiments, the GAIM variant additionally lacks amino acid 1 (e.g., ΔM1). In some aspects of these embodiments, the GAIM variant additionally lacks amino acids 1 and 2 (e.g., ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In some embodiments, the GAIM variant is a variant of SEQ ID NO:16 comprising a substitution of T50 with any other amino acid, the substitution H55T, and the substitution N137G. In at least one aspect of these embodiments, the substitution of T50 is selected from T50H, T50G, T50K, and T50R. In at least one aspect of these embodiments, the substitution of T50 is T50H. In some aspects of these embodiments, the GAIM variant further (i) comprises an N142A substitution; (ii) comprises a deglycosylating mutation of N38 and/or G40; (iii) lacks amino acid 1 or both amino acids 1 and 2; or (iv) any combination thereof. For example, in some aspects of these embodiments, the GAIM variant lacks amino acid 1 (e.g., ΔM1). In some aspects of these embodiments, the GAIM variant lacks amino acids 1 and 2 (e.g., ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In certain embodiments, the GAIM variant is a variant of SEQ ID NO:16 comprising the substitutions N137G and N142A. In some aspects of these embodiments, the GAIM variant further (i) comprises a substitution of T50 with any other amino acid as well as the substitution H55T; (ii) comprises a deglycosylating mutation of N38 and/or G40; (iii) lacks amino acid 1 or both amino acids 1 and 2; or (iv) any combination thereof. In certain aspects of these embodiments, the substitution of T50 is selected from T50H, T50G, T50K, and T50R. In at least one aspect of these embodiments, the substitution of T50 is T50H. In some aspects of these embodiments, the GAIM variant lacks amino acid 1 (e.g., ΔM1). In some aspects of these embodiments, the GAIM variant lacks amino acids 1 and 2 (e.g., ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In certain embodiments, the GAIM variant is a variant of SEQ ID NO:16 comprising the following substitutions: N142A, R143V, Q144N, and, optionally, A146V, A146T, or A146K. In certain embodiments, the GAIM variant is a variant of SEQ ID NO:16 comprising the following substitutions: N142A, R143V, Q144N, and A146V. In some aspects of these embodiments, the GAIM variant further (i) comprises a substitution of T50 with any other amino acid as well as the substitution H55T; (ii) comprises a deglycosylating mutation of N38 and/or G40; (iii) lacks amino acid 1 or both amino acids 1 and 2; or (iv) any combination thereof. In some aspects of these embodiments, the substitution of T50 is selected from T50H, T50G, T50K, and T50R. In at least one aspect of these embodiments, the substitution of T50 is T50H. In some aspects of these embodiments, the GAIM variant lacks amino acid 1 (ΔM1). In some aspects of these embodiments, the GAIM variant lacks amino acids 1 and 2 (ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In certain embodiments, the GAIM variant is a variant of SEQ ID NO:16 comprising the following substitutions: ΔT158, ΔD159, ΔP160, V161G and, optionally, (i) O156V or Q156Y and/or (ii) G157N. In certain aspects of these embodiments, the GAIM variant is a variant of SEQ ID NO:16 comprising the following substitutions: ΔT158, ΔD159, ΔP160, and V161G. In some aspects of these embodiments, the GAIM variant further (i) comprises a substitution of T50 with any other amino acid as well as the substitution H55T; (ii) comprises a deglycosylating mutation of N38 and/or G40; (iii) lacks amino acid 1 or both amino acids 1 and 2; or (iv) any combination thereof. In some aspects of these embodiments, the substitution of T50 is selected from T50H, T50G, T50K, and T50R. In at least one aspect of these embodiments, the substitution of T50 is T50H. In some aspects of these embodiments, the GAIM variant lacks amino acid 1 (ΔM1). In some aspects of these embodiments, the GAIM variant lacks amino acids 1 and 2 (ΔM1 and ΔA2). In some aspects of these embodiments, the GAIM variant further comprises a substitution of N38 with any amino acid other than cysteine, a substitution of G40 with any amino acid other than cysteine, threonine, or serine, or both a substitution of N38 with any amino acid other than cysteine and a substitution of G40 with any amino acid other than cysteine. In at least one aspect of these embodiments, the N38 substitution is N38A.

In at least one embodiment, a polypeptide of the present invention comprises a GAIM variant having the amino acid sequence of SEQ ID NO:19. In at least one embodiment, a polypeptide of the present invention comprises a GAIM variant having the amino acid sequence of SEQ ID NO:20. In at least one embodiment, a polypeptide of the present invention comprises a GAIM variant having the amino acid sequence of SEQ ID NO:21. In at least one embodiment, a polypeptide of the present invention comprises a GAIM variant having the amino acid sequence of SEQ ID NO:22. In at least one embodiment, a polypeptide of the present invention comprises a GAIM variant having the amino acid sequence of SEQ ID NO:23. In at least one embodiment, a polypeptide of the present invention comprises a GAIM variant having the amino acid sequence of SEQ ID NO:24. In at least one embodiment, a polypeptide of the present invention comprises a GAIM variant having the amino acid sequence of SEQ ID NO:25. In at least one embodiment, a polypeptide of the present invention comprises a GAIM variant having the amino acid sequence of SEQ ID NO:26.

Any of the above-described GAIM variants may be fused at the C-terminal end, directly or through a short linker, to an immunoglobulin constant region, to yield a GAIM-Ig fusion protein. The immunoglobulin constant region of the GAIM-Ig fusion proteins described herein may be the immunoglobulin constant region of IgG (including IgG1, IgG2, IgG3, and IgG4), IgA, IgD, IgE, or IgM. In some aspects, the immunoglobulin constant region is IgG. In certain aspects, the IgG is IgG1. In other aspects, the IgG is IgG2. In some embodiments, the immunoglobulin constant region is a human immunoglobulin constant region. In some embodiments, the immunoglobulin constant region is the Fc portion of a human IgG, or a fragment thereof. Fc portions of a human IgG suitable for the fusion proteins of the invention include wild-type or modified Fc portions. For example, a suitable modified Fc portion of a human IgG may stabilize the fusion protein and/or increase its half-life relative to wild-type Fc. Nonlimiting examples of modified Fc include those disclosed in U.S. Pat. Nos. 7,083,784, 7,217,797, 7,217,798, U.S. patent application Ser. No. 14/214,146, and WO-1997034631. In at least one embodiment, the immunoglobulin constant region is the Fc portion of human IgG1. In at least one embodiment, the immunoglobulin constant region is the Fc portion of human IgG2. In some embodiments, the immunoglobulin constant region of the GAIM-Ig fusion protein comprises a C-terminal lysine (e.g., K485). In other embodiments, the GAIM-Ig fusion lacks a C-terminal lysine (e.g., ΔK485).

In some embodiments, the GAIM-Ig fusion protein consists essentially of a polypeptide comprising any GAIM variant disclosed herein and the Fc portion of a human IgG (e.g., human IgG1). In at least one embodiment, the GAIM-Ig fusion protein consists essentially of a sequence at least 95%, 96%, 97%, 98%, or 99% identical to that described by SEQ ID NO:19 and the Fc portion of a human IgG (e.g., human IgG1). In some aspects of this embodiment, the amino acid sequence of the GAIM portion of the GAIM-Ig fusion protein differs from that described by SEQ ID NO: 19 by 10-15, 1-10, or 1-5 conservative substitutions. In other aspects of this embodiment, the GAIM-Ig fusion protein consists essentially of SEQ ID NO:19 and the Fc portion of a human IgG (e.g., human IgG1). For example, in some aspects, the GAIM-Ig fusion protein consists essentially of the amino acid sequence of SEQ ID NO:29 (PB108). In other aspects of this embodiment, the GAIM-Ig fusion protein consists essentially of a variant of SEQ ID NO:29 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:20 and the Fc portion of a human IgG (e.g., human IgG1). In some aspects of this embodiment, the amino acid sequence of the GAIM portion of the GAIM-Ig fusion protein differs from that described by SEQ ID NO: 20 by 10-15, 1-10, or 1-5 conservative substitutions. In other aspects of this embodiment, the GAIM-Ig fusion protein consists essentially of SEQ ID NO:20 and the Fc portion of a human IgG (e.g., human IgG1). For example, in some aspects, the GAIM-Ig fusion protein consists essentially of the amino acid sequence of SEQ ID NO:30 (PB122). In other aspects of this embodiment, the GAIM-Ig fusion protein consists essentially of a variant of SEQ ID NO:30 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:21 and the Fc portion of a human IgG (e.g., human IgG1). In some aspects of this embodiment, the amino acid sequence of the GAIM portion of the GAIM-Ig fusion protein differs from that described by SEQ ID NO: 21 by 10-15, 1-10, or 1-5 conservative substitutions. In other aspects of this embodiment, the GAIM-Ig fusion protein consists essentially of SEQ ID NO:21 and the Fc portion of a human IgG (e.g., human IgG1). For example, in some aspects, the GAIM-Ig fusion protein consists essentially of the amino acid sequence of SEQ ID NO:31 (PB116). In other aspects of this embodiment, the GAIM-Ig fusion protein consists essentially of a variant of SEQ ID NO:31 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1. ΔA2, and ΔK485).

In at least one embodiment, the GAIM-Ig fusion protein consists essentially of a sequence at least 95%, 96%, 97%, 98%, or 99% identical to that described by SEQ ID NO:22 and the Fc portion of a human IgG (e.g., human IgG1). In some aspects of this embodiment, the amino acid sequence of the GAIM portion of the GAIM-Ig fusion protein differs from that described by SEQ ID NO: 22 by 10-15, 1-10, or 1-5 conservative substitutions. In other aspects of this embodiment, the GAIM-Ig fusion protein consists essentially of SEQ ID NO:22 and the Fc portion of a human IgG (e.g., human IgG1). For example, in some aspects, the GAIM-Ig fusion protein consists essentially of the amino acid sequence of SEQ ID NO:32 (PB114). In other aspects of this embodiment, the GAIM-Ig fusion protein consists essentially of a variant of SEQ ID NO:32 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:23 and the Fc portion of a human IgG (e.g., human IgG1). In some aspects of this embodiment, the amino acid sequence of the GAIM portion of the GAIM-Ig fusion protein differs from that described by SEQ ID NO: 23 by 10-15, 1-10, or 1-5 conservative substitutions. In other aspects of this embodiment, the GAIM-Ig fusion protein consists essentially of SEQ ID NO:23 and the Fc portion of a human IgG (e.g., human IgG1). For example, in some aspects, the GAIM-Ig fusion protein consists essentially of the amino acid sequence of SEQ ID NO:33 (PB109). In other aspects of this embodiment, the GAIM-Ig fusion protein consists essentially of a variant of SEQ ID NO:33 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:24 and the Fc portion of a human IgG (e.g., human IgG1). In some aspects of this embodiment, the amino acid sequence of the GAIM portion of the GAIM-Ig fusion protein differs from that described by SEQ ID NO: 24 by 10-15, 1-10, or 1-5 conservative substitutions. In other aspects of this embodiment, the GAIM-Ig fusion protein consists essentially of SEQ ID NO:24 and the Fc portion of a human IgG (e.g., human IgG1). For example, in some aspects, the GAIM-Ig fusion protein consists essentially of the amino acid sequence of SEQ ID NO:34 (PB1110). In some embodiments, the GAIM-Ig fusion protein consists essentially of a variant of SEQ ID NO:34 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:25 and the Fc portion of a human IgG (e.g., human IgG1). In some aspects of this embodiment, the amino acid sequence of the GAIM portion of the GAIM-Ig fusion protein differs from that described by SEQ ID NO: 25 by 10-15, 1-10, or 1-5 conservative substitutions. In other aspects of this embodiment, the GAIM-Ig fusion protein consists essentially of SEQ ID NO:25 and the Fc portion of a human IgG (e.g., human IgG1). For example, in some aspects, the GAIM-Ig fusion protein consists essentially of the amino acid sequence of SEQ ID NO:35 (PB105). In other aspects of this embodiment, the GAIM-Ig fusion protein consists essentially a variant of SEQ ID NO:35 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In at least one embodiment, the GAIM-Ig fusion protein consists essentially of a sequence at least 95%, 96%, 97%, 98%, or 99% identical to that described by SEQ ID NO:26 and the Fc portion of a human IgG (e.g., human IgG1). In some aspects of this embodiment, the amino acid sequence of the GAIM portion of the GAIM-Ig fusion protein differs from that described by SEQ ID NO: 26 by 10-15, 1-10, or 1-5 conservative substitutions. In other aspects of this embodiment, the GAIM-Ig fusion protein consists essentially of SEQ ID NO:26 and the Fc portion of a human IgG (e.g., human IgG1). For example, in some aspects, the GAIM-Ig fusion protein consists essentially of the amino acid sequence of SEQ ID NO:36 (PB127). In other aspects of this embodiment, the GAIM-Ig fusion protein consists essentially of a variant of SEQ ID NO:36 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In some aspects of the invention, the GAIM portion and Ig portion of the GAIM-Ig fusions described herein are connected by a small linker. In some embodiments, the small linker is rich in glycine, serine, and/or threonine, comprising at least 80%, 85%, 90%, 91%, 92%, 93%, 94%, 95%, 96%, 97%, 98%, or 99% glycine, serine, and/or threonine. In some embodiments, the small linker comprises at least or about 50%, 55%, 60%, 70%, or 75% glycine, serine, and/or threonine. In some embodiments, the small linker is comprised substantially or entirely of glycine, serine, and/or threonine. A small linker of a GAIM-Ig fusion may be up to 25 amino acids in length, for example, from 1 to 5 amino acids in length, from 1 to 20 amino acids in length, from 5 to 10 amino acids in length, from 5 to 25 amino acids in length, or from 10 to 25 amino acids in length. Small linkers may have, for example, 1, 2, 3, 4, 5, 6, 7, 8, 9, 10, 11, 12, 13, 14, 15, 16, 17, 18, 19, 20, 21, 22, 23, 24, or 25 amino acids. In some embodiments, the small linker does not contain a human T-cell epitope or create a human T-cell epitope with either the GAIM variant or Fc domain to which it is bound. Exemplary small linkers include linkers having various numbers of repeats of the sequence GGGGS (4GS; SEQ ID NO:27) or GGGS (3GS; SEQ ID NO:28), such as from 2, 3, 4, to 5 repeats of such a sequence. Exemplary small linkers may include one or more lysine residues. Other exemplary small linkers include the amino acid sequence ARS.

The GAIM-Ig fusions described herein demonstrate several advantages over the prior art. Studies aimed at identifying the pathological forms of Aβ in the Alzheimer's disease (AD)-brain have shown that both insoluble plaque and soluble Aβ consists of a heterogeneous population of N- and C-terminal truncated Aβ peptides (Wildburger et al., (2017) Sci Rep 7:9520) forming structurally diverse conformations (Condello et al. (2018) PNAS, 115:E782-91; Rasmussen et al. (2017) PNAS, 114:13018-23; Liu et al. (2016) Sci Rep, 6:33079). It is also observed that majority of N-terminally truncated Aβ fragments constitute the major part of the amyloid plaque (Wildburger et al., (2017) Sci Rep 7:9520). However, the majority of antibody-related therapies against amyloid aggregation or misfolding have failed in the clinic at least in part due to their inability to effectively engage with N-terminally truncated or modified forms of amyloid. The GAIM-Ig fusions of the invention address the previously unmet need for a composition that can target a variety of amyloid proteins, as these fusions are capable of engaging various Aβ aggregates, even aggregates having different morphologies and aggregation properties.

The GAIM-Ig fusions disclosed herein bind, among other aggregates, the truncated 11-42 Aβ aggregates and/or post-translationally-modified pyro-glutamate Aβ aggregates, both of which are clinically relevant to Alzheimer's disease. As shown further in Tables 2 and 3, the GAIM-Ig fusions of the invention target multiple types of amyloid protein, including but not limited to Aβ aggregates, N-terminal truncated Aβ aggregates, tau, multiple conformers of transthyretin (TTR), and diverse morphologies of immunoglobulin light chain (LC) aggregates. These targets include amyloid protein found in patients at risk of or suffering from diseases described herein.

Antibody-related therapies of the prior art may also fail in the clinic because they fail to block aggregation of phosphorylated tau and/or fail to block tau's spread from one region of the brain to another. The open-stabilized GAIM-Ig fusions of the present invention address this need. The GAIM-Ig fusions of the invention cause remodeling of tau, thus preventing tau aggregates from seeding soluble tau and blocking tau aggregate propagation.

Taken together, GAIM-Ig fusions disclosed herein present a unique approach to prevent or remove pathological amyloid aggregates. Relative to prior art alternatives, the open-stabilized GAIM fusions described herein show greater potency, structural stability, and specificity to amyloid, including both Aβ and tau fibers, and are also either partially or fully deimmunized.

Preparation of Polypeptides

Polypeptides of the invention (e.g., polypeptides comprising one or more GAIM variants, including fusion proteins) can be synthesized using techniques well known in the art. For example, the polypeptides of the invention can be synthesized recombinantly in cells (see, e.g., Sambrook et al. 1989, Molecular Cloning A Laboratory Manual, Cold Spring Harbor Laboratory, N.Y. and Ausubel et al. 1989, Current Protocols in Molecular Biology, Greene Publishing Associates and Wiley Interscience, N.Y.). Alternatively, the polypeptides of the invention can be synthesized using known synthetic methods such as solid phase synthesis. Synthetic techniques are well known in the art (see, e.g., Merrifield, 1973, Chemical Polypeptides, (Katsoyannis and Panayotis eds.) pp. 335-61; Merrifield 1963, J. Am. Chem. Soc. 85:2149; Davis et al. 1985, Biochem. Intl. 10:394; Finn et al. 1976, The Proteins (3d ed.) 2:105; Erikson et al. 1976, The Proteins (3d ed.) 2:257; U.S. Pat. No. 3,941,763. Alternatively, the final construct may share essentially the same function as a recombinantly produced fusion protein, but simply be produced using non-recombinant techniques, such as ligation chemistry. Components of the fusion proteins may be prepared using the same general methodology described for g3p expression and g3p mutations.

In some embodiments, the polypeptide may be fused to a marker sequence, such as a peptide that facilitates purification of the fused polypeptide (either alone or in addition to fusion to another protein or incorporation of a carrier molecule). The marker amino acid sequence may be a hexa-histidine peptide (SEQ ID NO:53) such as the tag provided in a pQE vector (Qiagen, Mississauga, Ontario, Canada), among others, many of which are commercially available. As described in Gentz et al., Proc. Natl. Acad. Sci. (1989) 86:821-824, for instance, hexa-histidine (SEQ ID NO:53) provides for convenient purification of the fusion protein. Another peptide tag useful for purification, the hemagglutinin (HA) tag, corresponds to an epitope derived from the influenza HA protein. (Wilson et al., (1984) Cell 37:767).

Pharmaceutical Compositions

In some embodiments, the invention provides a pharmaceutical composition comprising any polypeptide comprising a GAIM variant described herein, optionally together with a pharmaceutically acceptable carrier, diluent or excipient. A "pharmaceutical composition" refers to a therapeutically effective amount of a composition as described herein with a physiologically suitable carrier and/or excipient. A pharmaceutical composition does not cause significant irritation to an organism. The phrases "physiologically suitable carrier" and "pharmaceutically acceptable carrier" may be used interchangeably to refer to a carrier or a diluent that does not cause significant irritation to an organism and does not abrogate the biological activity and properties of the administered composition. The term "excipient" refers to an inert substance added to a pharmaceutical composition to further facilitate administration of an active ingredient. Examples, without limitation, include, saline, calcium carbonate, calcium phosphate, various sugars and types of starch, cellulose derivatives, gelatin, vegetable oils, polyethylene glycols, and surfactants, including, for example, polysorbate 20.

Pharmaceutical compositions for use in accordance with the present invention may be formulated in a conventional manner using one or more physiologically acceptable carriers comprising excipients and auxiliaries, which facilitate processing of the active ingredients into compositions which can be used pharmaceutically. Proper formulation is dependent upon the route of administration chosen and upon the nature of the composition delivered (e.g., size and solubility of the polypeptide). In one aspect of these embodiments, the pharmaceutical composition is formulated for injection or infusion into the bloodstream of a patient. In another aspect of these embodiments, the pharmaceutical composition is formulated for direct administration to the brain or central nervous system of the patient, for example, by direct intramedullary, intrathecal, or intraventricular injection.

The compositions described herein may be formulated for parenteral administration, e.g., by bolus injection or continuous infusion. Pharmaceutical compositions for parenteral administration include aqueous solutions of the composition in water-soluble form. Additionally, suspensions of the active ingredients may be prepared as oily or water-based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents (e.g., surfactants such as polysorbate (Tween 20)) which increase the solubility of the active ingredients to allow for the preparation of highly-concentrated solutions. A protein-based agent such as, for example, albumin may be used to prevent adsorption of polypeptide of the invention to the delivery surface (i.e., IV bag, catheter, needle, etc.).

For oral administration, the pharmaceutical compositions can be formulated by combining the polypeptides described herein with pharmaceutically acceptable carriers well known in the art.

Formulations may be presented in unit dosage form, e.g., in vials, ampoules or in multidose containers with optionally, an added preservative. The compositions may be suspensions, solutions or emulsions in oily or aqueous vehicles, and may contain formulatory agents such as suspending, stabilizing and/or dispersing agents. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, such as by infusion, or via an implanted pump, such as an ICV pump. In the latter embodiment, the single dosage form may be an infusion bag or pump reservoir pre-filled with the appropriate amount of a polypeptide comprising a GAIM variant. Alternatively, the infusion bag or pump reservoir may be prepared just prior to administration to a patient by mixing an appropriate dose of the polypeptide comprising a GAIM variant with the infusion bag or pump reservoir solution.

Another aspect of the invention includes methods for preparing a pharmaceutical composition of the invention. Techniques for formulation of drugs may be found, for example, in "Remington's Pharmaceutical Sciences," Mack Publishing Co., Easton, Pa., latest edition, which is incorporated herein by reference in its entirety.

Pharmaceutical compositions suitable for use in the context of the present invention include compositions wherein the active ingredients are contained in an amount effective to achieve the intended purpose.

Determination of a therapeutically or diagnostically effective amount is well within the capability of those skilled in the art, especially in light of the detailed disclosure provided herein.

Dosage amount and interval may be adjusted individually to provide brain levels of the phage display vehicle which are sufficient to treat or diagnose a particular brain disease, disorder, or condition (minimal effective concentration, MEC). The MEC will vary for each preparation but can be estimated from in vitro data. Dosages necessary to achieve the MEC will depend on individual characteristics.

Dosage intervals can also be determined using the MEC value. Preparations should be administered using a regimen that maintains brain levels above the MEC for 10-90% of the time, preferably between 30-90% of the time and most preferably 50-90% of the time.

Depending on the severity and responsiveness of the disease to be treated, dosing can be of a single or a plurality of administrations, with a course of treatment lasting from several days to several weeks or until cure is effected or diminution of the disease state is achieved.

The amount of a composition to be administered will, of course, be dependent on the subject being treated or diagnosed, the severity of the affliction, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labelling approved by the U.S. Food and Drug Administration for prescription drugs or of an approved product insert. Compositions comprising a preparation of the invention formulated in a compatible pharmaceutical carrier may also be prepared, placed in an appropriate container, and labelled for treatment of an indicated disease, as further detailed herein.

Therapeutic Uses

Another aspect of the invention relates to the use of any of the polypeptides, nucleic acid molecules, or compositions of the invention, in the treatment one or more diseases associated with misfolded and/or aggregated amyloid protein, including, but not limited to, those diseases involving any of: transthyretin, immunoglobulin light chain (kappa or lambda), fAβ42, fasyn, fNM, or ftau.

In the context of treatments, the terms "patient", "subject," and "recipient" are used interchangeably and include humans as well as other mammals. In some embodiments, a patient is a human who is positive for a biomarker associated with a protein misfolding disease. In one embodiment, the patient exhibits β-amyloid deposits as detected by PET imaging with florbetapir.

The term "treating" and its cognates refer to reducing, slowing, or reversing the progression of a disease in a patient exhibiting one or more clinical symptoms of a disease. "Treating" also refers to reducing, slowing, or reversing the symptoms of a disease in a patient exhibiting one more clinical symptoms of a disease. In one embodiment, the patient exhibits β-amyloid deposits as detected by PET imaging with florbetapir and the number of β-amyloid deposits is reduced by the treatment. In one embodiment, the patient exhibits β-amyloid deposits as detected by the polypeptide or polypeptide compositions of the present invention and the number of f-amyloid deposits are reduced or maintained by the treatment. In another embodiment, the patient exhibits any type of amyloid deposits as detected by PET imaging and the cognitive function of the patient is improved by the treatment. Improvement in cognitive function may be assayed by the methods and tests of McKhann et al., Alzheimer's & Dementia 7(3):263-9(2011).

"Prophylaxis" or "prevention" (used herein interchangeably) is distinct from treating and refers to administration of a polypeptide, nucleic acid, or composition to an individual before the onset of any clinical symptoms. Prophylaxis using any of the polypeptides, nucleic acids, or compositions thereof of the present invention is encompassed. Prophylaxis may be implicated in individuals who are known to be at increased risk for a disease, or who are certain to develop a disease, solely on the basis of one or more genetic markers. Many genetic markers have been identified for the various protein misfolding diseases. For example, individuals with one or more of the Swedish mutation, Indiana mutation, or London mutation in hAPP are at increased risk for developing early-onset Alzheimer's Disease and so are candidates for prophylaxis. Likewise, individuals with the trinucleotide CAG repeats in the huntingtin gene, particularly those with 36 or more repeats, will eventually develop Huntington's Disease and so are candidates for prophylaxis.

Diseases associated with or characterized by misfolded and/or aggregated amyloid protein encompass diseases associated with (e.g., caused or correlated at least in part by) misfolded amyloid protein, aggregated amyloid protein, or both misfolded and aggregated amyloid protein. Peptides or proteins that may form amyloid are described above. For example, in some embodiments, amyloid is formed by Aβ, including but not limited to Aβ40, Aβ42, N-truncated Aβ11-42, Aβ11-42-Pyro, Aβ3-42-Pyro, Aβ1-42-E22Q-Dutch mutation, or a combination thereof. In some embodiments, amyloid is formed a prion protein, e.g., PrP$^{Sc}$. In some embodiments, amyloid is formed by transthyretin. In some embodiments, amyloid is formed by immunoglobulin light chain, for example immunoglobulin kappa light chain and/or immunoglobulin lambda light chain. In some embodiments, amyloid is formed by tau. In some embodiments, amyloid is formed by α-synuclein.

Diseases associated with or characterized by misfolded and/or aggregated amyloid protein are described above. Many of the above misfolded and/or aggregated amyloid protein diseases occur in the central nervous system (CNS). Nonlimiting examples of diseases occurring in the CNS are Parkinson's Disease: Alzheimer's Disease; frontotemporal dementia (FTD) including those patients having the following clinical syndromes: behavioral variant FTD (bvFTD), progressive non-fluent aphasia (PNFA) and semantic dementia (SD); frontotemporal lobar degenerations (FTLDs); and Huntington's Disease. The polypeptides, nucleic acids, and compositions of the invention may be used to treat diseases characterized by misfolded and/or aggregated amyloid protein that occur in the central nervous system (CNS).

Misfolding and/or aggregation of proteins may also occur outside the CNS. Amyloidosis A (AA) (for which the precursor protein is serum acute phase apolipoprotein, SAA) and multiple myeloma (precursor proteins immunoglobulin light and/or heavy chain) are two widely known protein misfolding and/or aggregated protein diseases that occur outside the CNS. Other examples include disease involving amyloid formed by α2-microglobulin, transthyretin (e.g., FAP, FAC, SSA), (apo)serum AA, apolipoproteins AI, AII, and AIV, gelsolin (e.g., Finnish form of FAP), immunoglobulin light chain (kappa or lambda), lysozyme, fibrinogen, cystatin C (e.g., Cerebral Amyloid Angiopathy, Hereditary Cerebral Hemorrhage with Amyloidosis, Icelandic Type), calcitonin, procalcitonin, islet amyloid polypeptide (e.g., IAPP amyloidosis), atrial natriuretic factor, prolactin, insulin, lactahedrin, kerato-epithelin, lactoferrin, odontogenic ameloblast-associated protein, and semenogelin I. The polypeptides, nucleic acids, and compositions of the invention may be used to treat diseases involving misfolding and/or aggregation of proteins occuring outside the CNS.

Diseases associated with or characterized by misfolded and/or aggregated amyloid protein may also involve tau lesions. Reviewed in Lee et al., Annu. Rev. Neurosci. 24:1121-159 (2001). Tau proteins are microtubule-associated proteins expressed in axons of both central and peripheral nervous system neurons. Neurodegenerative tauopathies (sometimes referred to as tauopathies) are encompassed. Examples of tauopathies include Alzheimer's Disease, Amyotrophic lateral sclerosis/parkinsonism-dementia complex, Argyrophilic grain dementia, Corticobasal degeneration, Creutzfeldt-Jakob disease, Dementia pugilistica, diffuse neurofibrillary tangles with calcification, Down's syndrome, Frontotemporal dementias including frontotemporal dementia with parkinsonism linked to chromosome 17, Gerstmann-Straussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, and Tangle only dementia. Some of these diseases may also include deposits of fibrillar amyloid R peptides. For example, Alzheimer's disease exhibits both amyloid R deposits and tau lesions. Similarly, prion-mediated diseases such as Creutzfeldt-Jakob disease, prion protein cerebral amyloid angiopathy, and Gerstmann-Straussler-Scheinker syndrome may have also have tau lesions. Thus, an indication that a disease is a "tauopathy" should not be interpreted as excluding the disease from other neurodegenerative or misfolded and/or aggregated amyloid protein disease classifications or groupings, which are provided merely as a convenience. The polypeptides and compositions of the invention may be used to treat neurodegenerative diseases as well as diseases involving tau lesions.

In some embodiments, a polypeptide, pharmaceutical composition, or formulation is for use in a method of reducing amyloid in a patient exhibiting symptoms related to the presence of amyloid or that is positive for a biomarker associated with a protein misfolding disease, comprising administering to the patient an effective amount of a pharmaceutical composition or formulation as described herein. In some embodiments, a polypeptide, pharmaceutical composition, or formulation is for use in a method of maintaining the level of amyloid in a patient exhibiting symptoms related to the presence of amyloid or that is positive for a biomarker associated with a protein misfolding disease, comprising administering to the patient an effective amount of a pharmaceutical composition or formulation as described herein. In some aspects of these embodiments, the biomarker is β-amyloid, which can be detected with the radiopharmaceutical agent florbetapir (AV-45, Eli Lilly). In some aspects of these embodiments, the route of administration is intrathecal injection or infusion, direct intraventricular injection or infusion, intraparenchymal injection or infusion, or intravenous injection or infusion.

In some embodiments, a polypeptide, pharmaceutical composition, or formulation is for use in a method of disaggregating or remodeling amyloid in a patient. In some embodiments, a polypeptide, pharmaceutical composition, or formulation is for use in a method of reducing amyloid formation in the brain. In some embodiments, a polypeptide, pharmaceutical composition, or formulation of the invention is for use in a method for promoting amyloid clearance in the brain. In some embodiments, a polypeptide, pharmaceutical composition, or formulation of the invention is for use in a method for inhibiting amyloid aggregation in the brain. In some embodiments, a polypeptide, pharmaceutical composition, or formulation of the invention is for use in a method for clearing toxic oligomers in the brain. In some embodiments, a polypeptide, pharmaceutical composition, or formulation of the invention is for use in a method for preventing the formation of toxic oligomers in the brain. In some embodiments, a polypeptide, pharmaceutical composition, or formulation of the invention is for use in method for protecting neurons from amyloid damage. In some embodiments, a polypeptide, pharmaceutical composition, or formulation is for use in a method of reducing cell-to-cell propagation of α-synuclein aggregates. In some embodiments, a polypeptide, pharmaceutical composition, or formulation is for use in a method of blocking cell-to-cell propagation of α-synuclein aggregates. In some aspects of these embodiments, the polypeptide, pharmaceutical composition, or formulation is administered to a patient in need thereof by intrathecal injection or infusion, direct intraventricular injection or infusion, intraparenchymal injection or infusion, or intravenous injection or infusion.

In some embodiments, a polypeptide, pharmaceutical composition, or formulation of the invention is for use in a method of causing disaggregation of Aβ-amyloid deposits in the brain, comprising injecting directly into the brain of a patient in need thereof an effective amount of the polypeptide, pharmaceutical composition, or formulation, thus causing a reduction in Aβ-amyloid deposits in the brain. In other embodiments, a polypeptide, pharmaceutical composition, or formulation of the invention is for use in a method of causing disaggregation of Aβ-amyloid deposits in the brain, comprising injecting by intravenous delivery into a patient in need thereof an effective amount of the polypeptide, pharmaceutical composition, or formulation, thus causing a reduction in Aβ-amyloid deposits in the brain.

In one embodiment, a pharmaceutical composition or formulation of the invention for use in protecting neurons from amyloid damage is given prophylactically.

In some embodiments, the patient is positive for a biomarker associated with a protein misfolding and/or aggregation disease. In one embodiment, the biomarker is β-amyloid and the agent used to detect β-amyloid is florbetapir (AV45, Eli Lilly).

Figure 10A:
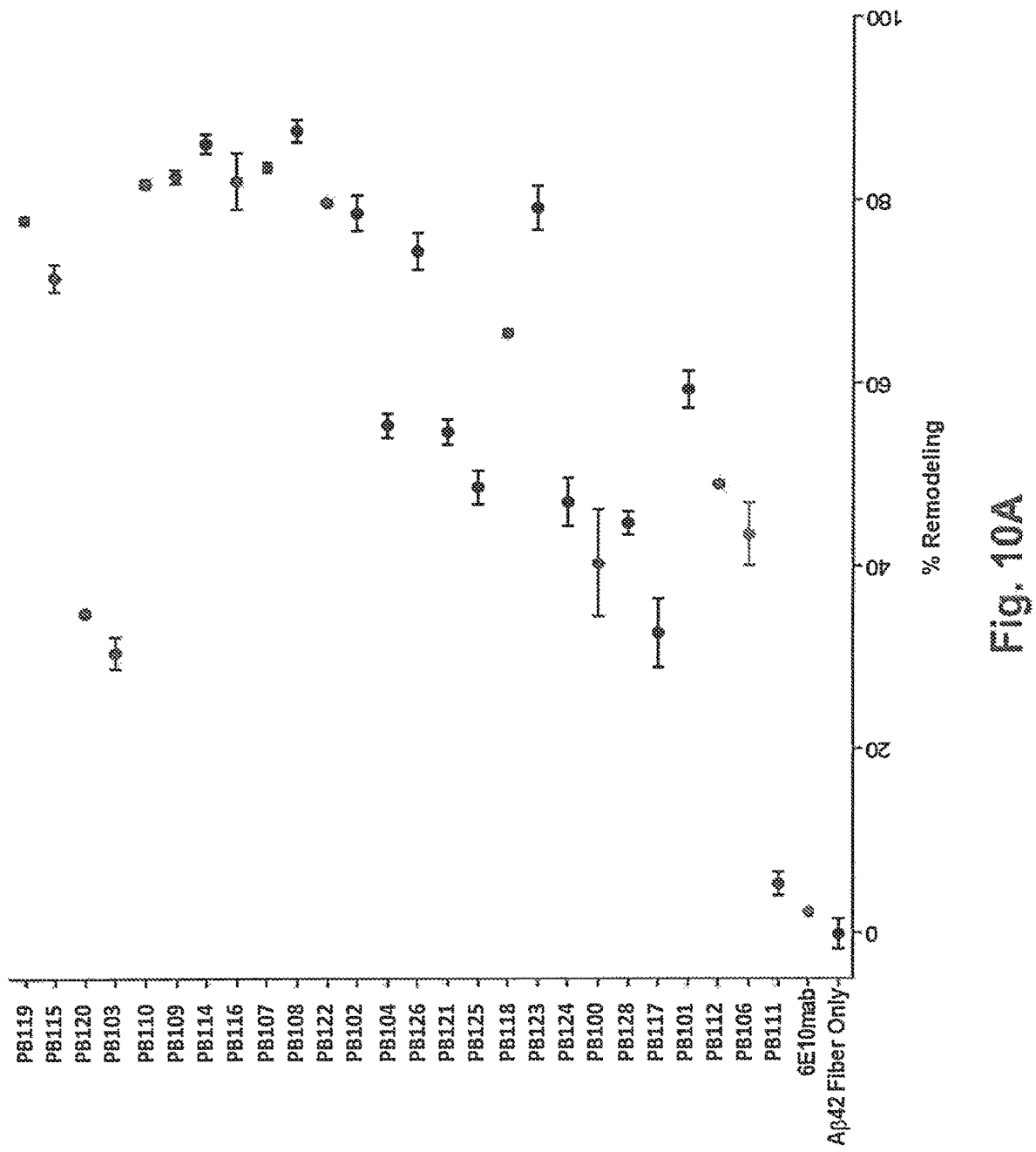
FIGS. 10A-10D address the remodeling efficiencies of different GAIM-Ig fusion proteins incubated with Aβ42 fibers.

Unlike prior art antibody-based therapies (e.g., 6E10), GAIM-Ig fusions as described herein target the core of amyloids rather than unstructured or partially structured N-terminal residues and demonstrate superior remodeling activity (FIG. 10A). Thus, in some embodiments, a polypeptide, pharmaceutical composition, or formulation of the invention is for use in a method of remodeling amyloid. In some aspects of these embodiments, the route of administration is intrathecal injection or infusion, direct intraventricular injection or infusion, intraparenchymal injection or infusion, or intravenous injection or infusion.

In general, the polypeptides disclosed herein bind to amyloid at least as effectively as M13 phage, g3p, or a variant or fusion protein of g3p disclosed in the prior art. In some embodiments, the polypeptides disclosed herein bind to amyloid more effectively than M13 phage, g3p, or a variant or fusion protein of g3p disclosed in the prior art. In some embodiments, the polypeptides disclosed herein remodel amyloid more effectively than do M13 phage, g3p, or a variant or fusion protein of g3p disclosed in the prior art. In some embodiments, the polypeptides disclosed herein inhibit amyloid aggregation more effectively than do M13 phage, g3p, or a variant or fusion protein of g3p disclosed in the prior art. In some embodiments, the polypeptides disclosed herein clear toxic oligomers more effectively than do M13 phage, g3p, or a variant or fusion protein of g3p disclosed in the prior art. In some embodiments, the polypeptides disclosed herein reduce cell-to-cell propagation of α-synuclein aggregates more effectively than do M13 phage, g3p, or a variant or fusion protein of g3p disclosed in the prior art. In some embodiments, the polypeptides disclosed herein detect amyloid more effectively than do M13 phage, g3p, or a variant or fusion protein of g3p disclosed in the prior art. In some embodiments, the polypeptides disclosed herein prevent a disease associated with misfolded and/or aggregated amyloid protein more effectively than do M13 phage, g3p, or a variant or fusion protein of g3p disclosed in the prior art. In some embodiments, the polypeptides disclosed herein treat a disease associated with misfolded and/or aggregated amyloid protein more effectively than do M13 phage, g3p, or a variant or fusion protein of g3p disclosed in the prior art. In some embodiments, the polypeptides disclosed herein elicit a smaller immune response in a patient as compared to M13 phage, g3p, or a variant or fusion protein of g3p disclosed in the prior art. In at least one embodiment, the polypeptides disclosed herein do not elicit an immune response in a patient.

In another embodiment, any of the diseases described above may be treated by administration of a nucleic acid molecule of the invention (i.e., encoding a polypeptide comprising a GAIM variant that exhibits reduced or no immunogenicity and that possesses the ability to bind amyloid, disaggregate/remodel amyloid, and/or inhibit aggregation of amyloid) alone or associated with a suitable carrier, e.g., a lipid nanoparticle, a polymeric carrier, or a vector, such as a viral vector directly to a patient by any suitable route, e.g., inhalation and intravenous infusion. The nucleic acid molecule encoding the polypeptide comprising a GAIM variant may be DNA or RNA.

Diagnostics

Diagnostic compositions are encompassed by the present invention and may comprise any of the above-described polypeptides of the invention (e.g., a polypeptide comprising a GAIM variant, such as a polypeptide comprising a GAIM-Ig fusion. Thus, in some embodiments, the polypeptides, pharmaceutical compositions, and formulations described herein are used in diagnostic applications associated with the various diseases described herein. For example, binding of a polypeptide of the invention to amyloid protein may be used to detect the bound amyloid protein. Similarly, binding of a polypeptide of the invention when used as an imaging agent in vivo or in vitro may be part of a diagnosis of a protein-misfolding, protein-aggregation, or neurodegenerative disease described herein.

In some embodiments, a polypeptide described herein is used as an amyloid-imaging agent, wherein the imaging agent can detect amyloid protein and diagnose a disease associated with misfolded and/or aggregated amyloid protein. Because the polypeptides described herein bind amyloid irrespective of the type of fiber, they can image and detect any amyloid aggregate (Aβ, tau, α-synuclein, transthyretin, immunoglobulin light chain, etc.) and may diagnose a wide range of amyloid-associated diseases and conditions. In some embodiments, the polypeptide used as an amyloid-imaging agent further comprises a detectable label.

Various labels can be attached to a polypeptide comprising a GAIM variant as described herein using standard techniques for labeling proteins. Examples of labels include fluorescent labels and radiolabels. There are a wide variety of radiolabels that can be used, but in general the label is often selected from radiolabels including, but not limited to, $^{18}$F, $^{11}$C, and $^{123}$I. These and other radioisotopes can be attached to the protein using well known chemistry. In one embodiment, the label is detected using positron emission tomography (PET). However, any other suitable technique for detection of radioisotopes may also be used to detect the radiotracer.

The polypeptides and compositions of the invention may be used as diagnostic imaging agents in combination with an imaging agent that is specific for β-amyloid such as, for example, F18-AV-45, Eli Lilly. Because the use of a diagnostic composition of the invention together with a β-amyloid-specific imaging agent will result in the detection of non-β-amyloid aggregates based on differential detection, in one embodiment, a diagnostic composition of the invention is used as an imaging agent in combination with a β-amyloid imaging agent to detect non-β-amyloid aggregates.

In some embodiments, the polypeptides described herein, or compositions thereof, are used to detect β-amyloid in the CNS, including the brain.

Diagnostic compositions of the invention may be administered using the same routes described for therapeutic compositions. In some embodiments, the route of administration is intrathecal injection or infusion, direct intraventricular injection or infusion, intraparenchymal injection or infusion, or intravenous injection or infusion.

Recombinant Techniques

In some aspects, the present invention relates to oligonucleotides comprising a nucleic acid sequence that encodes a polypeptide of the invention. For example, the present invention relates to a nucleic acid sequence encoding polypeptides comprising a GAIM variant, including polypeptides comprising a GAIM variant attached directly or through a small linker to an immunoglobulin constant region, as disclosed herein. In general, nucleic acids encoding a polypeptide comprising a GAIM variant or GAIM-Ig fusion are prepared using conventional recombinant DNA techniques, such as cloning of mutant GAIM domains, direct DNA synthesis, or by isolating the corresponding DNA from a library using, for example, the M13 sequence as a probe. See, e.g., Sambrook et al. 1989, Molecular Cloning A Laboratory Manual, Cold Spring Harbor Laboratory, N.Y.; Ausubel et al. 1989, Current Protocols in Molecular Biology, Greene Publishing Associates and Wiley Interscience, N.Y. Nucleic acids encoding a polypeptide comprising a GAIM variant or GAIM-Ig fusion may also be prepared as provided in the Examples below.

For recombinant production, any of the nucleic acid sequences of the invention may be inserted into an appropriate expression vector which contains the necessary elements for the transcription and translation of the inserted coding sequence, or in the case of an RNA viral vector, the necessary elements for replication and translation. The encoding nucleic acid is inserted into the vector in proper reading frame. Accordingly, the invention provides vectors comprising nucleic acids of the invention. Such vectors include, but are not limited to, DNA vectors, phage vectors, viral vectors, retroviral vectors, etc. Vectors may include, for example, baculovirus, cauliflower mosaic virus, tobacco mosaic virus. Ri plasmid, or Ti plasmid. The choice of appropriate vector in which to clone the nucleic acids of the invention may be made by those of skill in the art using well-known knowledge of the compatibility of the vector with the chosen host cell in which to carry out expression. This may be done in any of mammalian cells, plant cells, insect cells, bacterial cells, fungal cells, transgenic animal cells, etc. Exemplary mammalian cells suitable for producing polypeptides described herein include but are not limited to HEK293 cells, HEK293-derived cells, CHO cells, CHO-derived cells, HeLa cells, and COS cells. Exemplary bacterial cells include but are not limited to *E. coli* cells. Exemplary plant cells include but are not limited to duckweed cells. See, e.g., U.S. Pat. No. 8,022,270. Appropriate vectors for each of these cell types are well-known in the art and are generally commercially available. Nonlimiting exemplary transfection methods are described in Sambrook et al., Molecular Cloning, A Laboratory Manual, 3rd ed. Cold Spring Harbor Laboratory Press (2001). Nucleic acids may be transiently or stably transfected in the desired host cells according to methods known in the art.

In at least one embodiment, the nucleic acid encodes a polypeptide comprising the amino acid sequence of SEQ ID NO:19. In at least one embodiment, the nucleic acid encodes a polypeptide comprising the amino acid sequence of SEQ ID NO:20. In at least one embodiment, the nucleic acid encodes a polypeptide comprising the amino acid sequence of SEQ ID NO:21. In at least one embodiment, the nucleic acid encodes a polypeptide comprising the amino acid sequence of SEQ ID NO:22. In at least one embodiment, the nucleic acid encodes a polypeptide comprising the amino acid sequence of SEQ ID NO:23. In at least one embodiment, the nucleic acid encodes a polypeptide comprising the amino acid sequence of SEQ ID NO:24. In at least one embodiment, the nucleic acid encodes a polypeptide comprising the amino acid sequence of SEQ ID NO:25. In at least one embodiment, the nucleic acid encodes a polypeptide comprising the amino acid sequence of SEQ ID NO:26.

In at least one embodiment, the nucleic acid encodes a polypeptide consisting essentially of SEQ ID NO:19 and the Fc portion of a human IgG (e.g., human IgG1). In at least one embodiment, the nucleic acid encodes a polypeptide consisting essentially of SEQ ID NO:20 and the Fc portion of a human IgG (e.g., human IgG1). In at least one embodiment, the nucleic acid encodes a polypeptide consisting essentially of SEQ ID NO:21 and the Fc portion of a human IgG (e.g., human IgG1). In at least one embodiment, the nucleic acid encodes a polypeptide consisting essentially of SEQ ID NO:22 and the Fc portion of a human IgG (e.g., human IgG1). In at least one embodiment, the nucleic acid encodes a polypeptide consisting essentially of SEQ ID NO:23 and the Fc portion of a human IgG (e.g., human IgG1). In at least one embodiment, the nucleic acid encodes a polypeptide consisting essentially of SEQ ID NO:24 and the Fc portion of a human IgG (e.g., human IgG1). In at least one embodiment, the nucleic acid encodes a polypeptide consisting essentially of SEQ ID NO:25 and the Fc portion of a human IgG (e.g., human IgG1). In at least one embodiment, the nucleic acid encodes a polypeptide consisting essentially of SEQ ID NO:26 and the Fc portion of a human IgG (e.g., human IgG1).

In some embodiments, the nucleic acid encodes a polypeptide consisting essentially of the amino acid sequence of SEQ ID NO:29 (PB108). In some embodiments, the nucleic acid encodes a polypeptide consisting essentially of the amino acid sequence of SEQ ID NO:30 (PB122). In some embodiments, the nucleic acid encodes a polypeptide consisting essentially of the amino acid sequence of SEQ ID NO:31 (PB116). In some embodiments, the nucleic acid encodes a polypeptide consisting essentially of the amino acid sequence of SEQ ID NO:32 (PB114). In some embodiments, the nucleic acid encodes a polypeptide consisting essentially of the amino acid sequence of SEQ ID NO:33 (PB109). In some embodiments, the nucleic acid encodes a polypeptide consisting essentially of the amino acid sequence of SEQ ID NO:34 (PB110). In some embodiments, the nucleic acid encodes a polypeptide consisting essentially of the amino acid sequence of SEQ ID NO:35 (PB105). In some embodiments, the nucleic acid encodes a polypeptide consisting essentially of the amino acid sequence of SEQ ID NO:36 (PB127). As described above, these embodiments encompass a nucleic acid encoding a variant of SEQ ID NOs: 29, 30, 31, 32, 33, 34, 35, or 36 in which the variant lacks amino acid 1 (ΔM1), amino acids 1 and 2 (ΔM1 and ΔA2), amino acid 485 (ΔK485), amino acids 1 and 485 (ΔM1 and ΔK485), or amino acids 1, 2, and 485 (ΔM1, ΔA2, and ΔK485).

In some embodiments, the nucleic acid encoding a polypeptide of the invention comprises SEQ ID NO:37. In some embodiments, the nucleic acid comprises SEQ ID NO:38. In some embodiments, the nucleic acid comprises SEQ ID NO:39. In some embodiments, the nucleic acid comprises SEQ ID NO:40. In some embodiments, the nucleic acid comprises SEQ ID NO:41. In some embodiments, the nucleic acid comprises SEQ ID NO:42. In some embodiments, the nucleic acid comprises SEQ ID NO:43. In some embodiments, the nucleic acid comprises SEQ ID NO:44. In some embodiments, the nucleic acid comprising any of SEQ ID NOs: 37, 38, 39, 40, 41, 42, 43, or 44 further comprises a nucleic acid encoding the Fc portion of IgG (e.g., human IgG1 or IgG2). In at least one embodiment, the nucleic acid encoding an open-stabilized GAIM variant and the nucleic acid encoding the Fc portion of IgG are connected by a nucleic acid encoding a small linker. In at least one embodiment, the nucleic acid encodes the small linker ARS. In some embodiments, the nucleic acid further encodes a signal sequence. In some embodiments, the nucleic acid further encodes a signal sequence having the 18-amino acid N-terminal sequence of GenBank Ref Seq NP_510891.1.

In at least one embodiment, the nucleic acid encoding a polypeptide of the invention is SEQ ID NO:45. In at least one embodiment, the nucleic acid is SEQ ID NO:46. In at least one embodiment, the nucleic acid is SEQ ID NO:47. In at least one embodiment, the nucleic acid is SEQ ID NO:48. In at least one embodiment, the nucleic acid is SEQ ID NO:49. In at least one embodiment, the nucleic acid is SEQ ID NO:50. In at least one embodiment, the nucleic acid is SEQ ID NO:51. In at least one embodiment, the nucleic acid is SEQ ID NO:52.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. Another amplifiable marker is the DHFRr eDNA (Simonsen and Levinson, PNAS (1983) 80:2495). Selectable markers are reviewed by Thilly (Mammalian Cell Technology, Butterworth Publishers, Stoneham, MA) and the choice of selectable markers is well within the level of ordinary skill in the art. The expression elements of the expression systems vary in their strength and specificities. Depending on the host/vector system utilized, any of many suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter), and the like may be used; when cloning in insect cell systems, promoters such as the baculovirus polyhedron promoter may be used; when cloning in plant ceil systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker. In cases where plant expression vectors are used, the expression of sequences encoding linear or non-cyclized forms of the expression product of the invention may be driven by any of a number of promoters. For example, viral promoters such as the 35S RNA and 19S RNA promoters of CaMV (Brisson et al., Nature (1984) 31 0:511-514), or the coat protein promoter of TMV (Takamatsu et al., EMBO J (1987) 6.307-311) may be used; alternatively, plant promoters such as the small subunit of RUBISCO (Coruzzi et al., EMBO J. (1984) 3:1671-1680; Broglie et al., Science (1984) 224:838-843) or heat shock promoters, e.g., soybean hsp17.5-E or hsp17.3-B (Gurley et al., Mol. Cell. Biol. (1986) 6:559-565) may be used. These constructs can be introduced into plant cells using Ti plasmids, Ri plasmids, plant virus vectors, direct DNA transformation, microinjection, electroporation, etc. See, e.g., Weissbach & Weissbach 1988, Methods for Plant Molecular Biology, Academic Press, NY, Section VIII, pp. 421-463; and Grierson & Corey 1988, Plant Molecular Biology, 2d Ed., Blackie, London, Ch. 7-9. In one insect expression system that may be used to produce proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an AcNPV promoter (for example, the polyhedron promoter). Successful insertion of a coding sequence results in inactivation of the polyhedron gene and production of non-occluded recombinant virus, i.e. virus lacking the proteinaceous coat coded for by the polyhedron gene. These recombinant viruses are used to infect *Spodoptera frugiperda* cells in which the inserted gene is expressed. See, e.g., Smith et al., J. Viral. (1983) 46:584; U.S. Pat. No. 4,215,051. Further examples of this expression system may be found in Ausubel et al., eds. 1989, Current Protocols in Molecular Biology, Vol. 2, Greene Publish. Assoc. & Wiley Interscience.

In mammalian host cells, any of several viral based expression systems may be used. In cases where an adenovirus is used as an expression vector, a coding sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts (see, e.g., Logan & Shenk, PNAS (1984) 81:3655). Alternatively, the vaccinia 7.5 K promoter may be used (see, e.g., Mackett et al., PNAS (1982) 79:7415; Mackett et al., J. Viral. (1984) 49:857; Panicali et al., PNAS (1982) 79:4927). Other viral expression systems include adeno-associated virus and lentiviruses.

In another embodiment, the invention provides a host cell harboring the vector containing a nucleic acid of the invention. Methods of transfecting or transforming or otherwise getting a vector of the invention into a host cell are known in the art. A cell harboring the vector, when cultured under appropriate conditions, will produce the polypeptides of the invention. As noted above, suitable host cells include but are not limited to mammalian cells, transgenic animal cells, plant cells, insect cells, bacterial cells, and fungal cells. For example, suitable host cells include but are not limited to HEK293 cells, HEK293-derived cells, CHO cells, CHO-derived cells, HeLa cells, and COS cells.

Host cells comprising nucleic acid constructs (e.g., vectors) are grown in an appropriate growth medium. As used herein, the term "appropriate growth medium" means a medium having nutrients required for the growth of cells. The recombinantly-produced polypeptides of the invention can be isolated from the culture media using techniques known in the art.

Specific examples of vectors and cells used for the recombinant production of the polypeptides of the invention are set forth in the Examples below.

EXAMPLES

Example 1: TauK18P301L Expression, Purification and Fiber Assembly

Human TauK18P301 L fragment corresponding to residues 244-372 of Tau-441 (2N4R) with the P213L mutation were expressed and purified as described for tau-MTBR (Krishnan et al. (2014) J Mol Biol, 426:2500-19). TauK18P301 L fibers were assembled by adding 40 μM low-molecular weight heparin (Fisher Scientific) to 40 μM TauK18P301L monomer in 0.1 M sodium acetate pH 7.0 buffer containing 2 mM DTT and incubating for 3 days at 37° C. Fiber formation was confirmed by Thioflavin T (ThT).

Example 2: Aβ Fiber Assembly

Aβ1-42 (rPeptide), N-truncated Aβ11-42 (Bachem), Aβ11-42-Pyro (AnaSpec), Aβ3-42-Pyro (AnaSpec) and Aβ1-42-E22Q (AnaSpec) were dissolved in hexafluoroisopropanol (HFIP) and incubated at room temperature for 24 hours until a clear solution developed. The peptide solution was dried under vacuum for 1 h. Fibers were assembled as described by Stine et al., 2003. One hundred micrograms Aβ peptide was dissolved in 40 µL DMSO, diluted to 1140 µL in 10 mM HCl solution, and incubated with shaking at 500 rpm for 24 hours at 37° C. Fiber formation was confirmed by ThT.

Example 3: Generation of GAIM-Ig Fusion Proteins

Site-specific mutagenesis of the control scaffold PB120 was performed in β-strands facing the inner groove of the GAIM domains (FIG. 1A). These β-strands, 4 and 5 in the N1 domain and 9 and 10 in the N2 domain, facilitate inter-domain interactions in the closed state of GAIM and prevent the exposure of the TolA binding site (Hoffman-Thoms et al. (2013) J Biol Chem, 288:12979-91) previously shown to in part overlap with the amyloid binding motif in GAIM (Krishnan et al. (2014) J Mol Biol, 426:2500-19). In addition, sites in the N2-hinge region involved in N1-N2 domain assembly and specific regions in N2 important for F-pili binding were mutated (Weininger et al. (2009) PNAS, 106:12335-40; Deng and Perham (2002) J Mol Biol, 319:603-14) to investigate how GAIM amyloid binding activity translates to its function during phage infection.

GAIM-Ig fusion proteins were expressed using the Expi293™ Expression System (Thermo Fisher Scientific) according to manufacturer's instructions. Purification of the proteins was performed on HiTrap® MabSelect™ SuRe™ column (GE Healthcare Lifesciences) in 20 mM sodium phosphate, pH 7.0 followed by a gradient elution in 20 mM sodium acetate from pH 4.0 to pH 3.6 over 20 CV using AKTA™ Pure FPLC system. Fusion proteins were dialyzed into D-PBS pH 7 and filter sterilized (UltrafreeO-MC spin columns, Millipore). Protein purity was analyzed by NuPAGE™ 4-12% Bis-Tris gel system with MES SDS Running Buffer (Thermo Fisher Scientific) followed by InstantBlue™ Staining Solution (Expedeon). In addition, analytical SEC was used to assess the purity of GAIM IgG-fusions using a TSKgel® G3000SW XL, 7.8 mm IDx30 cm, 5 µM column (TOSOH BIOSCIENCES) in an UltiMate™ 3000 UHPLC focused system (ThermoFisher Scientific). For each sample, 7.5 µg of protein was injected onto the SEC column, separation was performed in D-PBS mobile phase at a flow rate of 0.5 mL/min. Peak purity was analyzed using Chromeleon™ 7 software. GAIM IgG-fusion variants were synthesized by ATUM.

Example 4: Generation of GAIM Dimers

GAIM dimers were generated from the GAIM-Ig fusions using the FabRICATOR® (IdeS) enzyme (Genovis), which specifically clips the fusion at the immunoglobulin hinge to yield GAIM dimers linked by two disulfide bonds (FIG. 1C), for 2 hours at 37° C. Cleavage was followed by separation from Fc by Capto™ Adhere according to the manufacturer's protocol. Purity of GAIM dimer was confirmed on a NuPAGE™ 4-12% Bis-Tris gel system separated in MES SDS Running Buffer. GAIM dimer (0.5 µM) was incubated for 2 hours at 25° C. in 100 mM potassium phosphate, pH 7.0 with increasing concentrations of Guanidine (Sigma). The fluorescence was measured in 10-mm cells at 310 nm and 340 nm after excitation at 280 nm and at 360 nm after excitation at 295 nm. The data were analyzed using a two-state folding model assuming a linear dependence of fluorescence emissions on guanidine hydrochloride concentration. After confirming expected molecular size and clearance of Fc fragments on SDS-PAGE gel, the protein was subjected to unfolding studies.

Example 5: Thermal Unfolding of GAIM Monitored by SYPRO® Orange Binding Assay A SYPRO® Orange binding assay was carried out to monitor GAIM domain separation and stability of the N2 domain. SYPRO® Orange binds poorly to the closed conformation of folded GAIM in an aqueous solution. When the two domains of GAIM dissociate and expose hydrophobic residues, the dye binds to the exposed hydrophobic surfaces and shows increased fluorescence. One micromolar GAIM-Ig fusion in PBS was mixed with ×20 excess of SYPRO® Orange (Invitrogen cat. no. S-6650) in a 96-well plate and sealed. Thermal unfolding was monitored in a Roche LightCycler® 480 RT-PCR by continuous increase in temperature from 20° C. to 95° C. at a rate of 0.24° C./minute. Excitation was set to 465 nm and emission at 580 nm with melt factor at 1, quant factor at 10 and maximum integration time for two seconds. The arbitrary unit of fluorescent signal was recorded and normalized to a scale of 0-100 (Layton and Hellinga, 2011).

Figure 4A:
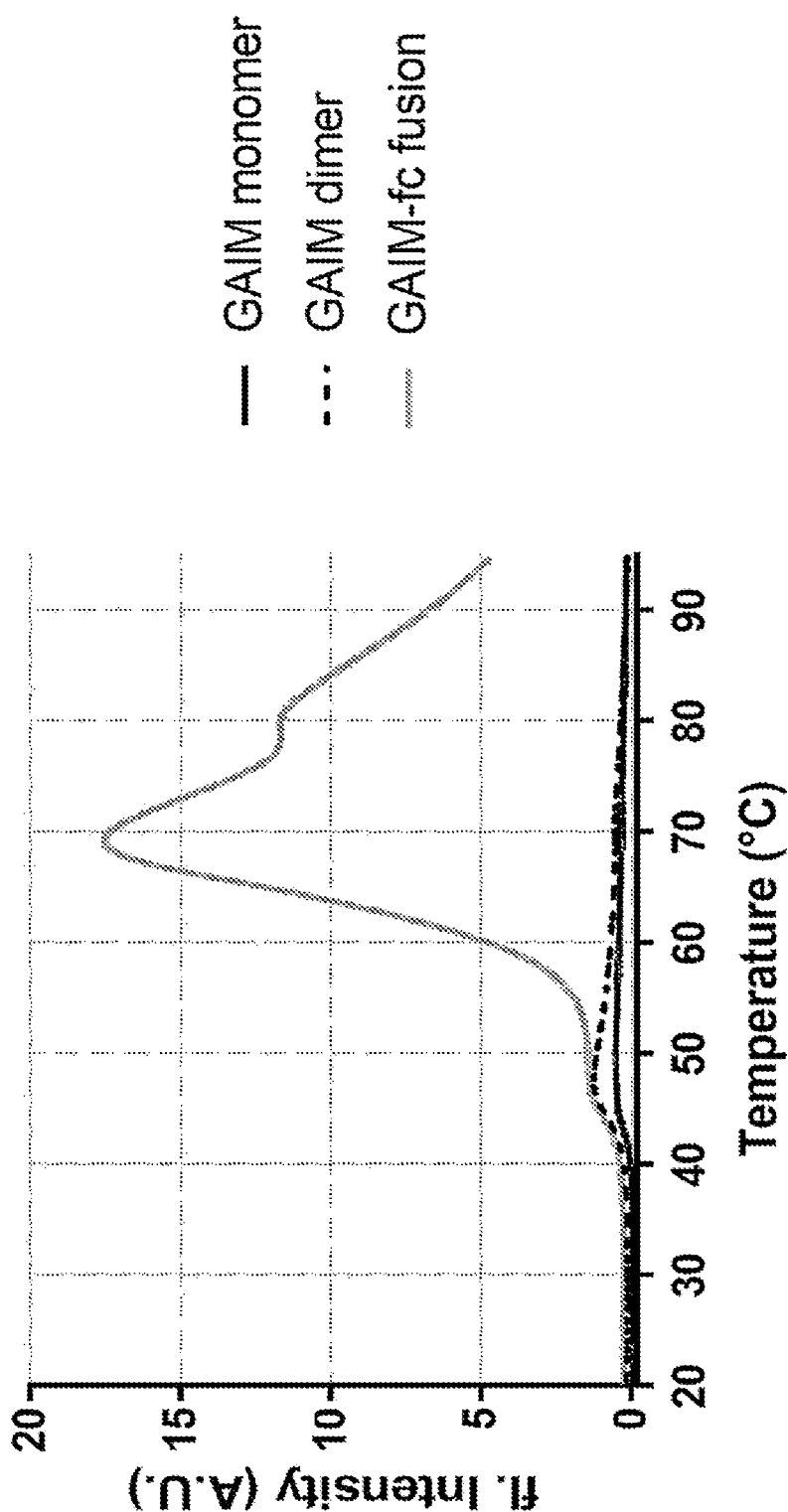
FIGS. 4A and 4B show representative data from thermal melting experiments of a GAIM-Ig fusion compared to a GAIM dimer or monomer. Thermal melting was monitored by SYPRO® Orange binding. The first transition, Tm1, was calculated by non-linear fitting from normalized fluorescence intensities.
Figure 4B:
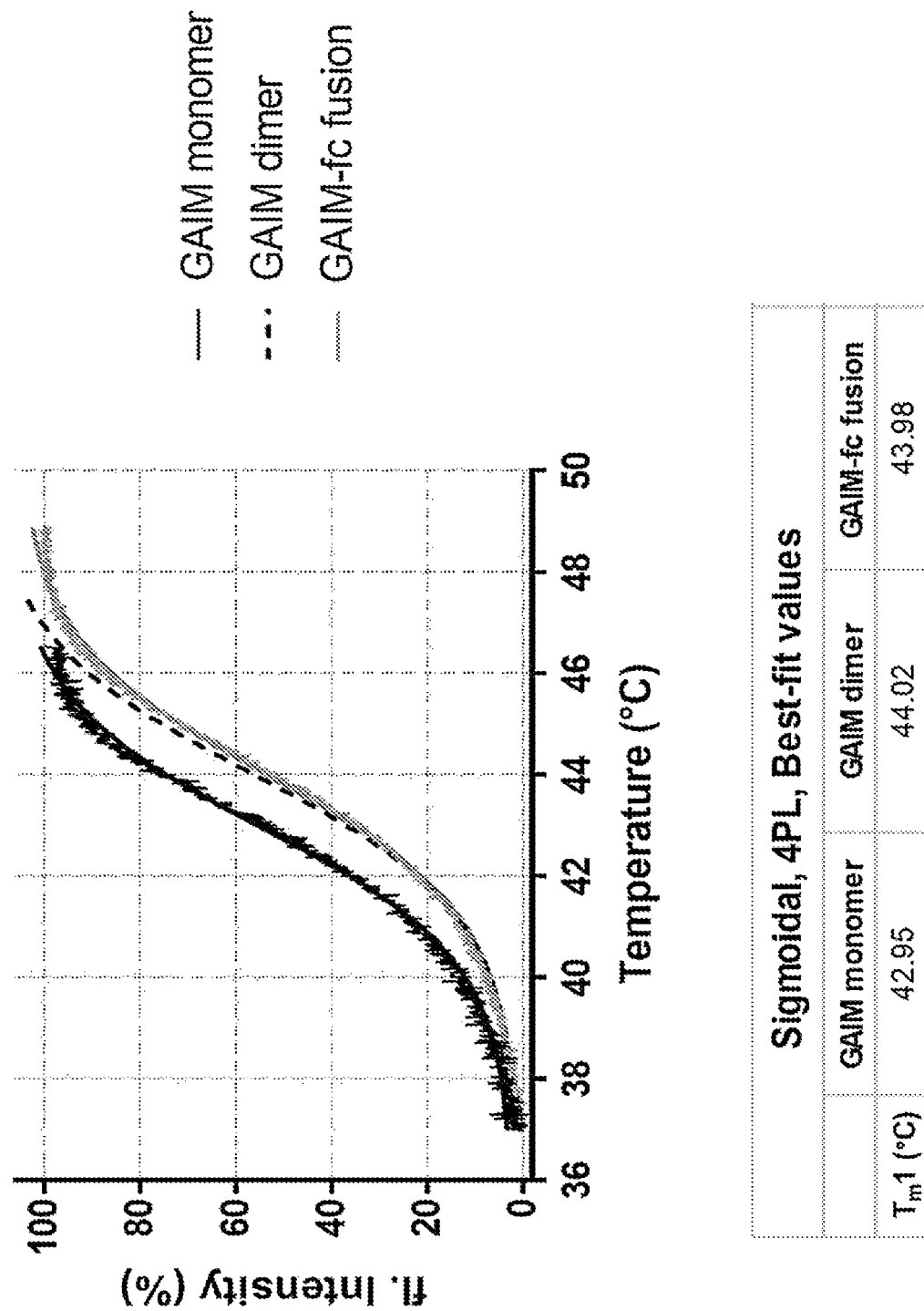

Thermal unfolding of the GAIM monomer monitored by SYPRO® Orange binding showed a single transition around 43° C. that corresponds to the domain opening and N2 unfolding transition (FIGS. 4A-4B). GAIM dimers obtained according to Example 4 showed identical melting profiles to monomers in solution, whereas GAIM-Ig fusions in solution showed three distinct transitions upon thermal unfolding (FIGS. 4A-4B). The first transition, Tm1, occurred around 44° C., as seen in the GAIM-monomers and dimers (FIG. 4B). Two additional transitions at 64° C. and 81° C. are like the Fc domains unfolding transitions (Traxlmayr et al., 2012, Biochim Biophys Acta, 1824:524-529). Comparing the GAIM-specific Tm1 showed that the GAIM and Fc domains remain as independent folding domains and no new structural elements are generated in the chimeric molecule.

Figure 5A:
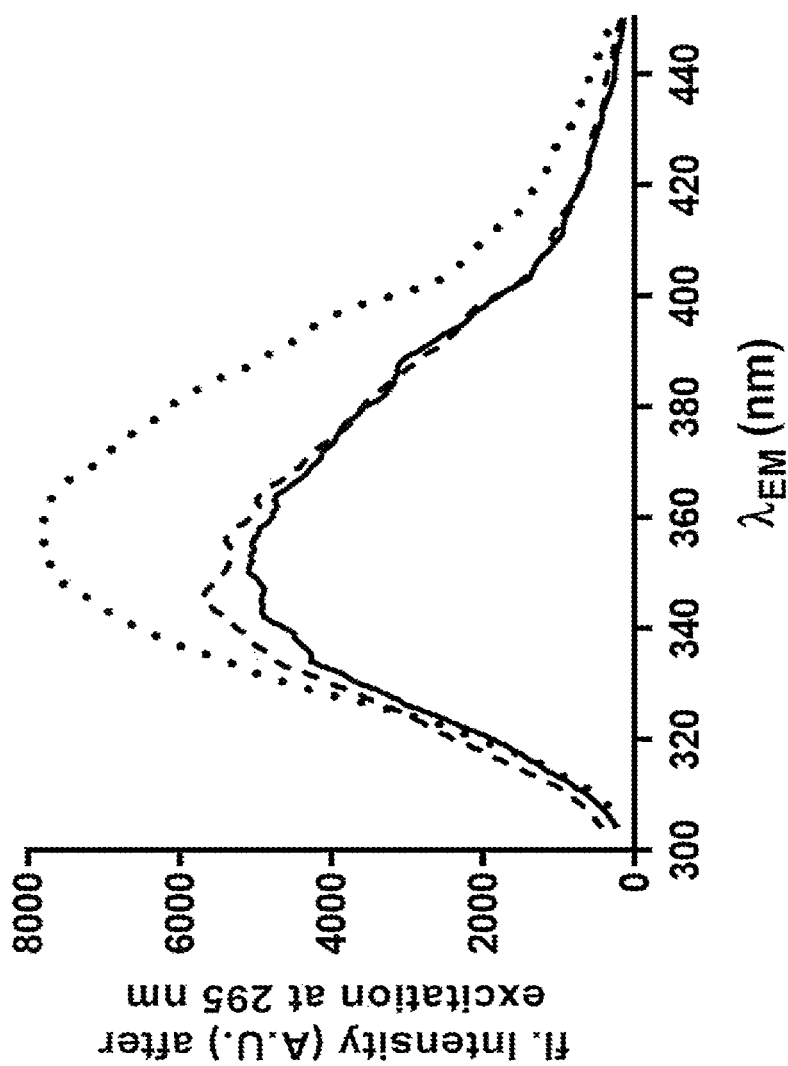
FIGS. 5A and 5B depict fluorescence emission spectra of GAIM at 0 M guanidine hydrochloride (GuHCl) (broken lines), 2 M GuHCl (continuous lines), and 5 M GuHCl (dotted lines) excited at 295 nm (FIG. 5A) and 280 nm (FIG. 5B).
Figure 5B:
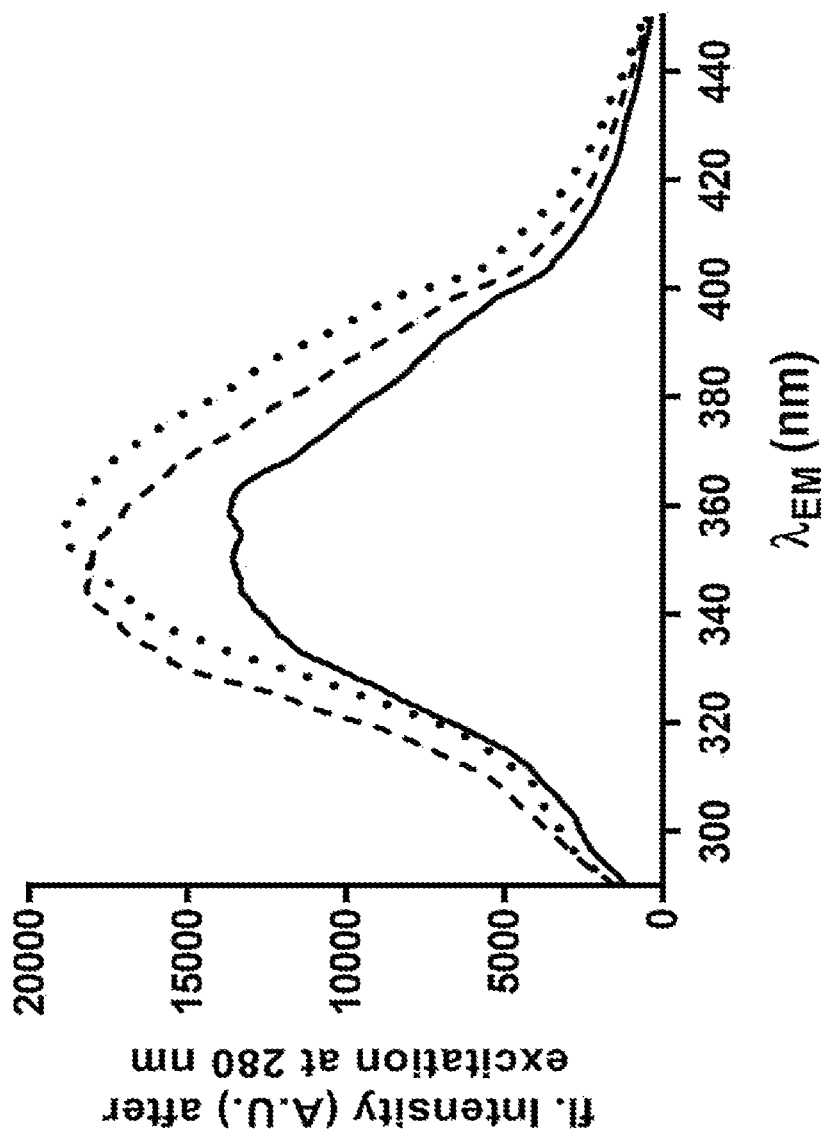

Example 6: GAIM Retains Its Native Conformational Stability in the IgG Fusion Dimer The conformational stability of GAIM in the IgG-fusion was investigated using guanidine hydrochloride (GuHCl)-induced unfolding of GAIM dimer by intrinsic fluorescence. GAIM dimers were generated as described in Example 4 and were equilibrated in 0, 2, and 5 M GuHCl solutions at 25° C. for 2 hours. Selective excitation of the Trp residues at 295 nm showed a minimal change in GAIM dimer fluorescence intensities between 0 and 2 M concentrations, with no change in the emission λmax (345 nm) (FIG. 5A). At 5 M GuHCl, the Trp fluorescence was red-shifted by 15 nm (λmax 360 nm) and the fluorescence intensity was significantly higher than both 0 and 2 M samples. GAIM dimers were then excited at 280 nm (Trp and Tyr residues) and the fluorescence emission spectra was recorded (FIG. 5B). The fluorescence emission intensity at 340 nm decreased between 0 and 2 M GuHCl and then increased by a similar margin at 5 M GuHCl. Similar spectral changes were also observed in g3p (Martin and Schmid, 2003, J Mol Biol, 328:863-75), indicating that GAIM in the GAIM-Ig fusion variants retained the native conformational stability of GAIM in native g3p.

Figure 5C:
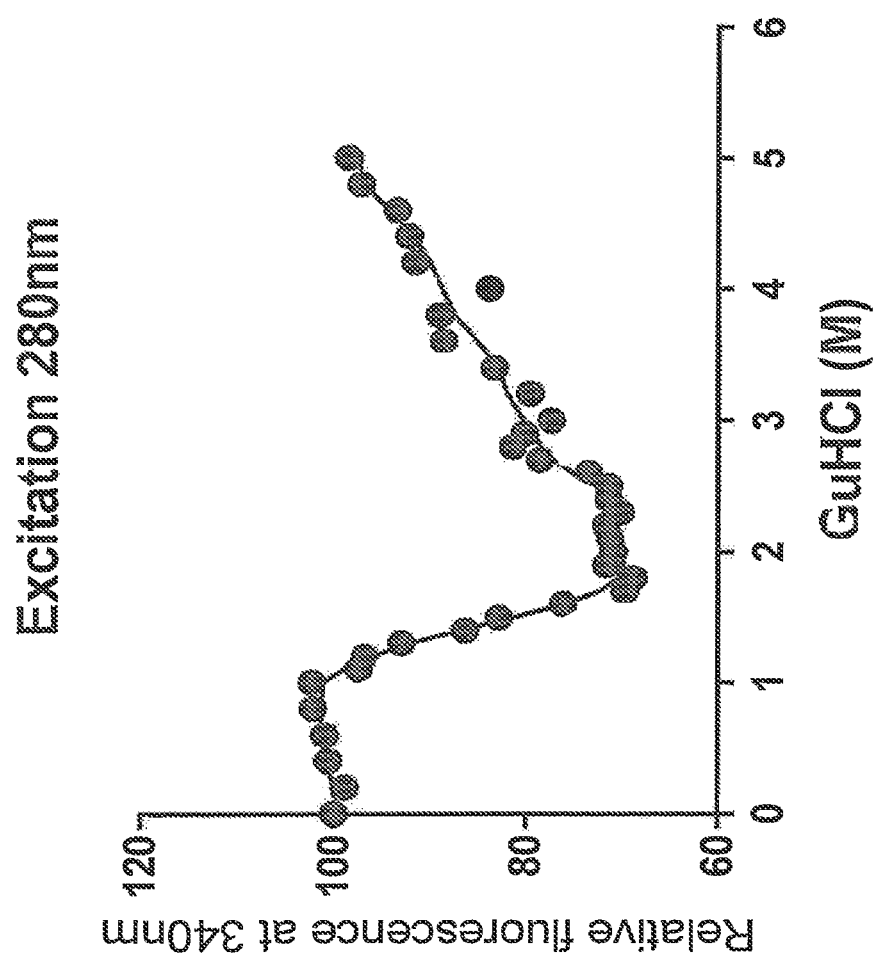
FIG. 5C depicts equilibrium unfolding of GAIM dimer by GuHCl.
Figure 5D:
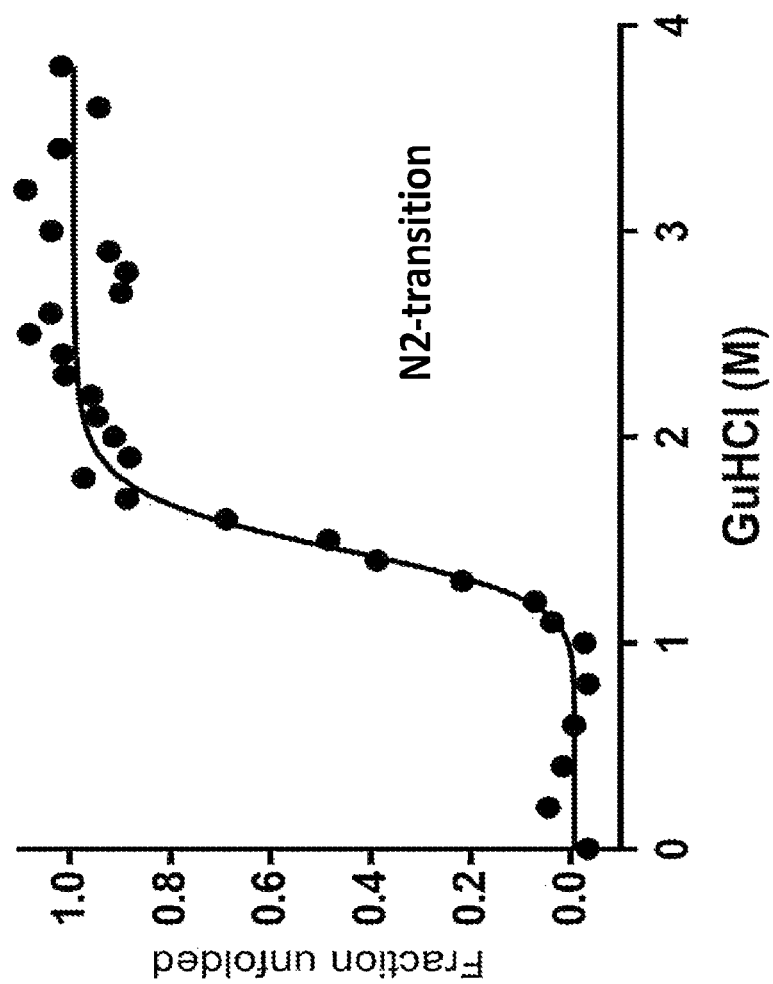
FIG. 5D depicts N2 domain unfolding at 1.5 M GuHCl.
Figure 5E:
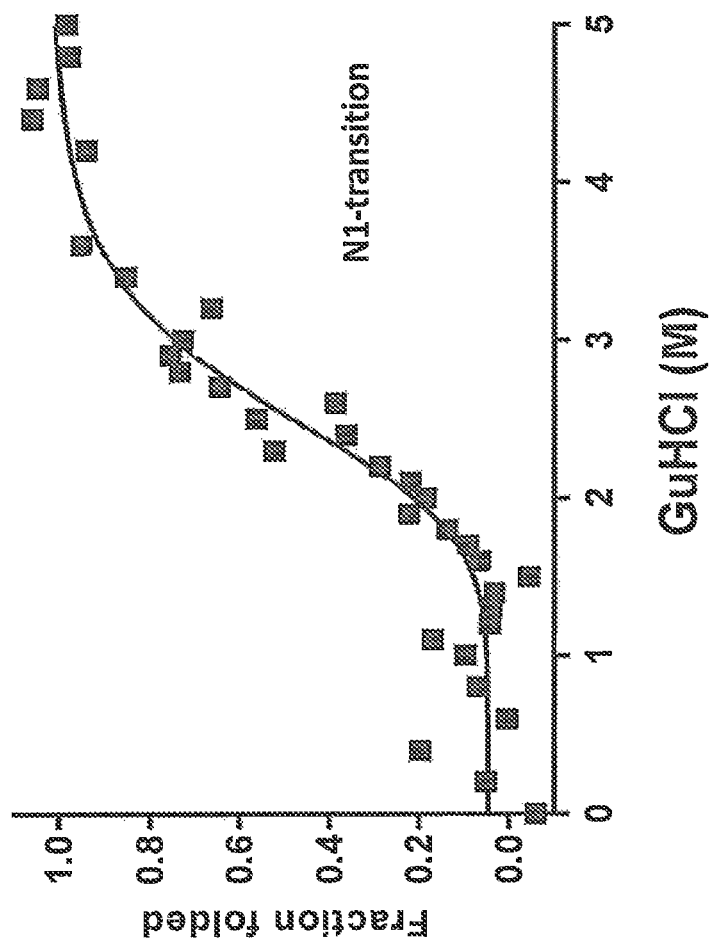
FIG. 5E depicts N1 domain unfolding at 2.6 M GuHCl.

We generated detailed denaturation profiles of GAIM dimers by recording fluorescence emission intensities at 310, 340, and 360 nm in a range of concentrations of GuHCl. GAIM dimers showed a biphasic denaturation profile at 340 nm when excited at 280 nm (FIG. 5C). The first transition occurred between 1 and 2 M GuHCl and the next between 2 and 3 M GuHCl. We then fitted the 310 nm (excitation 280 nm) and 360 nm (excitation 295 nm) denaturation profiles to a two-state protein unfolding model (FIGS. 5D-5E) and calculated the N2 and N1 domain denaturation transitions at 1.5 M and 2.6 M GuHCl respectively. The first transition at 1.5 M GuHCl represents the separation of the two domains N1 and N2 and the simultaneous unfolding of the less stable N2 domain. The second transition represents the unfolding of the more stable N1 domain at 2.6 M GuHCl. These values correspond to previously-reported denaturation transitions in g3p (Martin and Schmid, 2003, J Mol Biol, 328:863-75). Therefore, these data indicate that each GAIM in the GAIM dimer in the GAIM-Ig fusion forms an independent folding unit and adopts a conformation similar to the g3p tip protein from filamentous phages.

Example 7: GAIM-Ig Fusions Bind Aβ and Tau Fibers

Fifty microliters of Aβ fibers (0.8 µM) or tauK18P301L fibers (1 µM) in 50 mM carbonate buffer, pH 9.6 was added per well in a 96-well MaxiSorp® plate (Thermo Fisher) and incubated 16 hours at 4° C. Wells were washed 3 times with DPBS-Tween (0.05%) and 2 times with DPBS, followed by blocking with SuperBlock™ (Thermo Scientific) for 1.5 hours at room temperature. Wells were washed 3 times with PBS. GAIM-Ig fusion was added in high concentration PBS-T (14.7 mM $KH_2PO_4$, 80.6 mM $Na_2HPO_4$-$7H_2O$, 27 mM KCl, 1.38 M NaCl, 0.05% tween) at the indicated concentrations and incubated at 37° C. for 2 hours followed by 3 washes in DPBS-Tween (0.05%) and 3 washes with DPBS. Human specific Fc-HRP antibody (Jackson ImmunoResearch, cat. no. 109-035-008) diluted 1:5000 in DPBS-Tween (0.05%) containing 0.2% gelatin was added for 45 minutes at 37° C. After 2 washes in DPBS-Tween (0.05%) and 2 washes in DPBS the signal was developed with TMB solution (Thermo Fisher), the reaction was stopped by the addition of 0.25 N HCl and the absorbance at 450 nm was recorded with a Tecan Infinite® M1000 PRO plate reader.

Figure 6A:
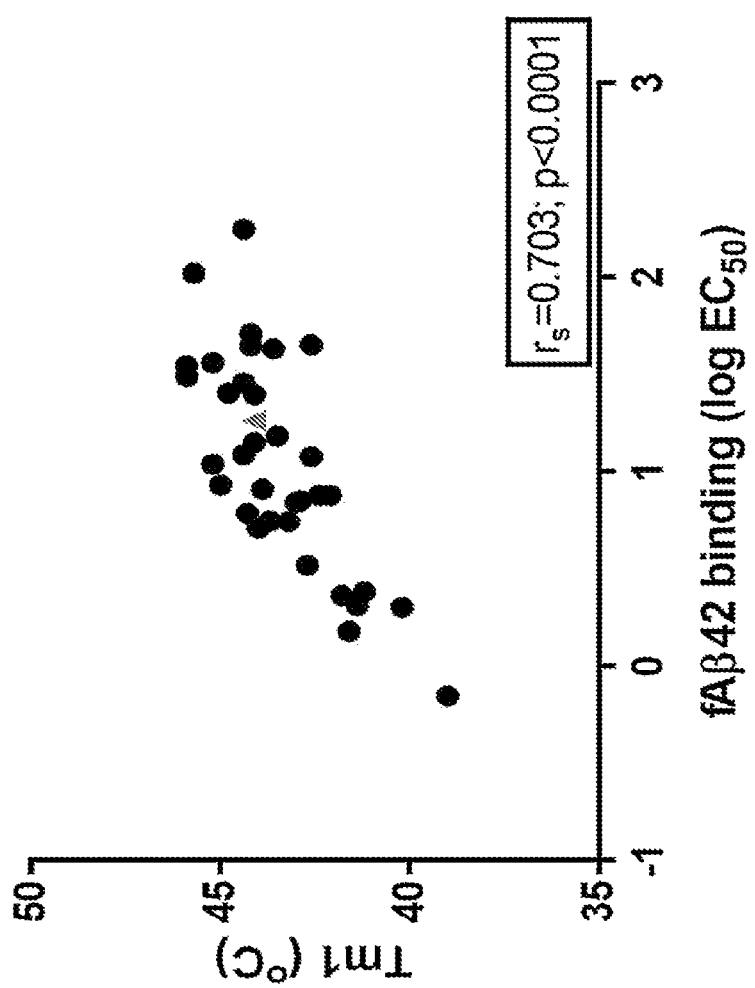
FIGS. 6A and 6B depict the mapping of GAIM residues that modulate amyloid binding.

Most of the mutations in N1 and N2 residues facing the inner groove of GAIM were found to affect the in A31-42 fiber binding by ELISA (FIG. 6A). Binding activities of the mutated GAIM variants ranged from 0.7 nM to 175 nM $EC_{50}$, representing a more than 250-fold change in binding affinity to fAβ42. There was a strong correlation (P-value $10^{-4}$, $r_s$=0.703) between binding efficacy ($EC_{50}$) and the first melting transition (Tm1). A decrease in Tm1 represents a more open conformation of GAIM with increased binding, stabilized variants with higher Tm1 tend to lose their binding activity. This is suggestive of an amyloid fiber binding motif in GAIM being exposed when the inter-domain interactions are weakened and agrees with previous data showing that GAIM binding is temperature dependent (Krishnan et al. (2014) J Mol Biol, 426.2500-19).

Figure 6B:
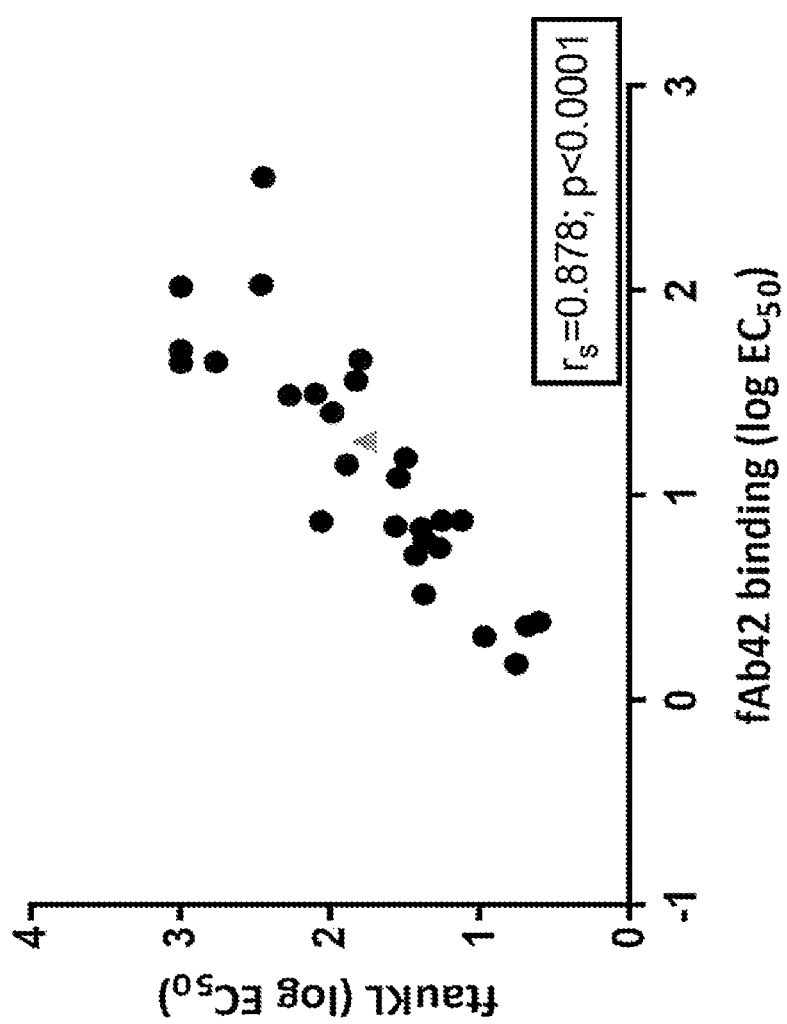

To discern whether the change in binding activity for fAβ42 translates to other amyloids proteins, a subset of the variants was tested by ELISA for binding to amyloid fibers formed from the microtubule-binding region of tau. Comparing GAIM-Ig variants' binding activities ($EC_{50}$) for fAβ42 and ftau (P-value $10^{-4}$, $r_s$=0.878; FIG. 6B) showed a tight correlation in the binding activity of GAIM-Ig (P-value $10^{-4}$, $r_s$=0.862) for the two different amyloids.

Figure 7A:
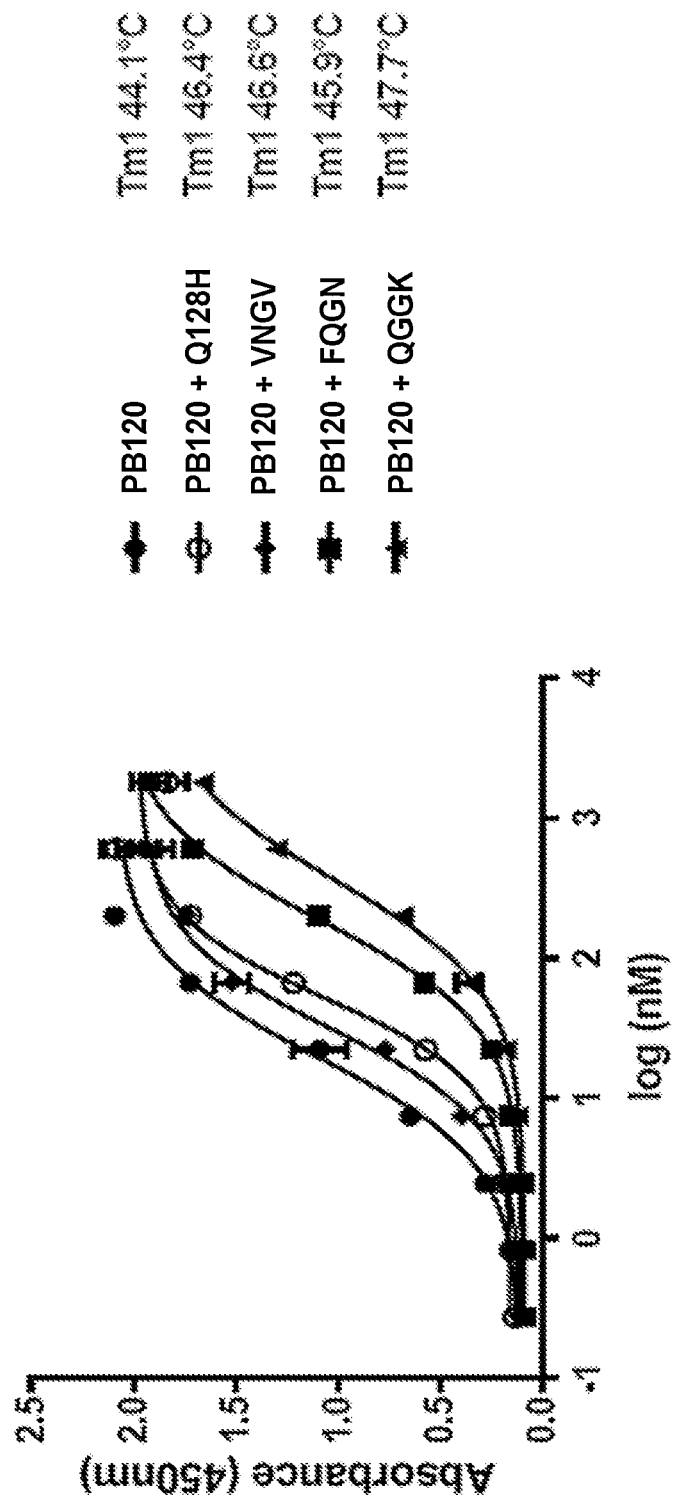
FIGS. 7A and 7B show amyloid binding for select GAIM-Ig fusion proteins.
Figure 9:
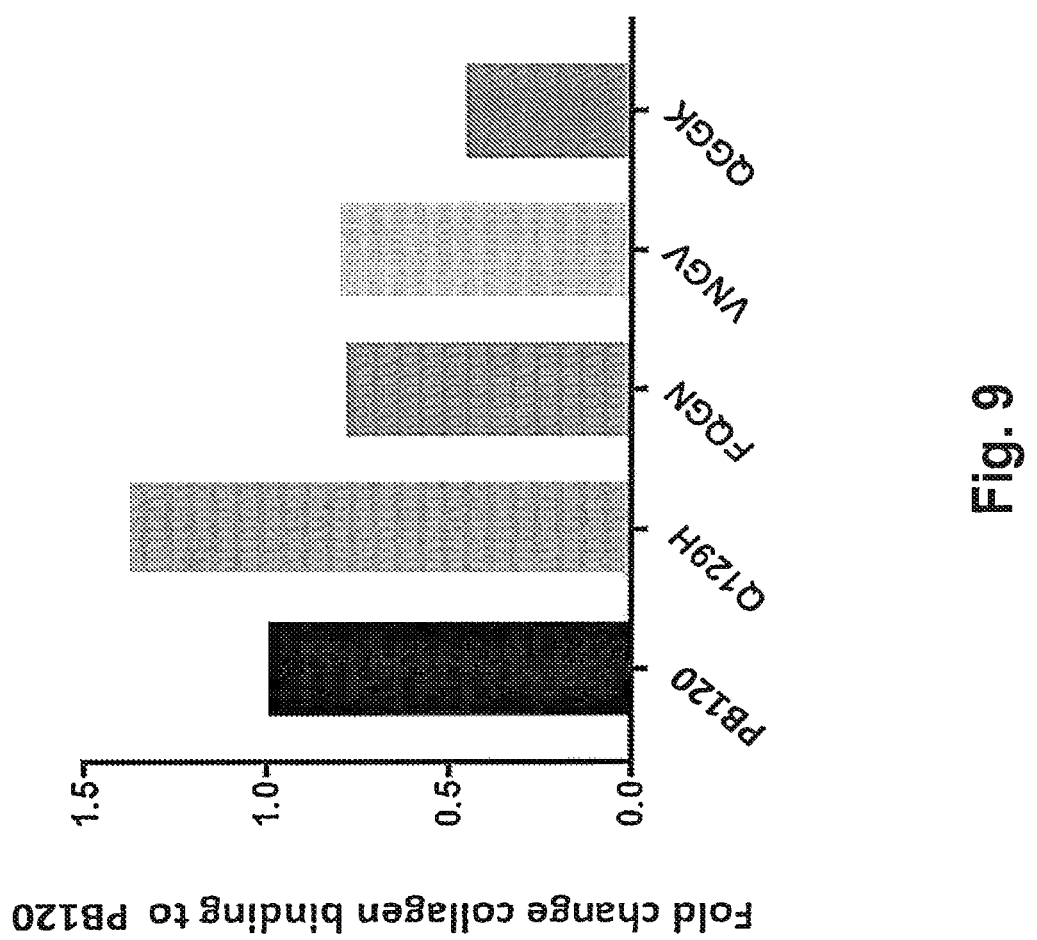
FIG. 9 shows the effect of N2-stabilizing mutations on off-target binding to collagen. FQGN=SEQ ID NO:8, VNGV=SEQ ID NO:9; QGGK=SEQ ID NO:10.

Example 8: Superior Binding of Open-Stabilized GAIM-Ig Fusion Proteins Over Stabilized GAIM-Ig Fusion Proteins Several mutations in GAIM that stabilized the N2 domain and favored a stronger interaction with the N1 domain led to decreased amyloid binding. Elimination of a proline containing loop in the N2 domain by substituting the $Q_{156}GTDPVK_{162}$ loop (SEQ ID NO:7) with QGGK (SEQ ID NO:10) increased Tm1 by 3.6° C. and resulted in 18-fold loss of fAβ42 binding (FIG. 7A). Likewise, amino acid substitutions of $F_{135}QNN_{138}$ (SEQ ID NO:5) to FQGN (SEQ ID NO:8) and $R_{143}QGA_{148}$ (SEQ ID NO:6) to VNGV (SEQ ID NO:9) stabilized N2 (Tm1) by 1.8° C. and 2.5° C. respectively. These stabilized variants showed reduced fAβ42 binding activity compared to the GAIM scaffold. (FIG. 7A). Similarly, introducing the Q128H mutation, which stabilizes the interactions of the N2 hinge subdomain and N1, decreased fiber binding (FIG. 7A). The substitutions of T1, T2, or T3 in the N2 domain all reduced non-specific binding to collagen, although the Q128H showed a marginal 1.4-fold increase (FIG. 9). Such mutants indicate an inverse relationship between the potency of a GAIM variant's amyloid-binding activity and its stability.

Figure 7B:
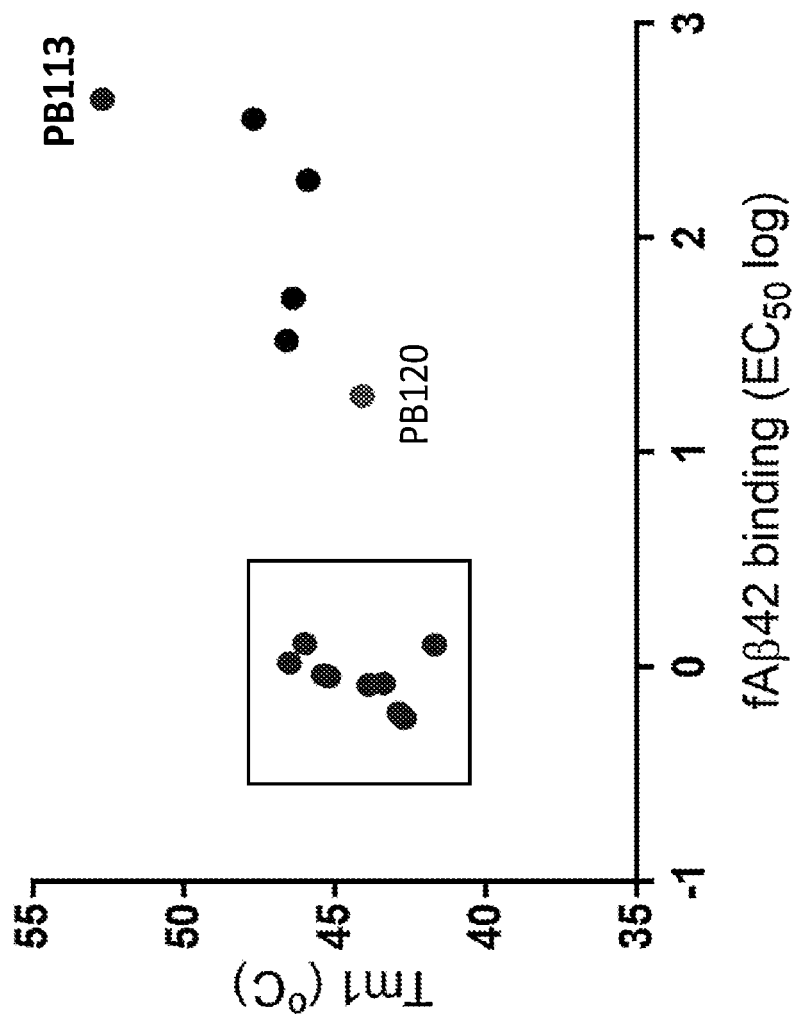
Figure 8A:
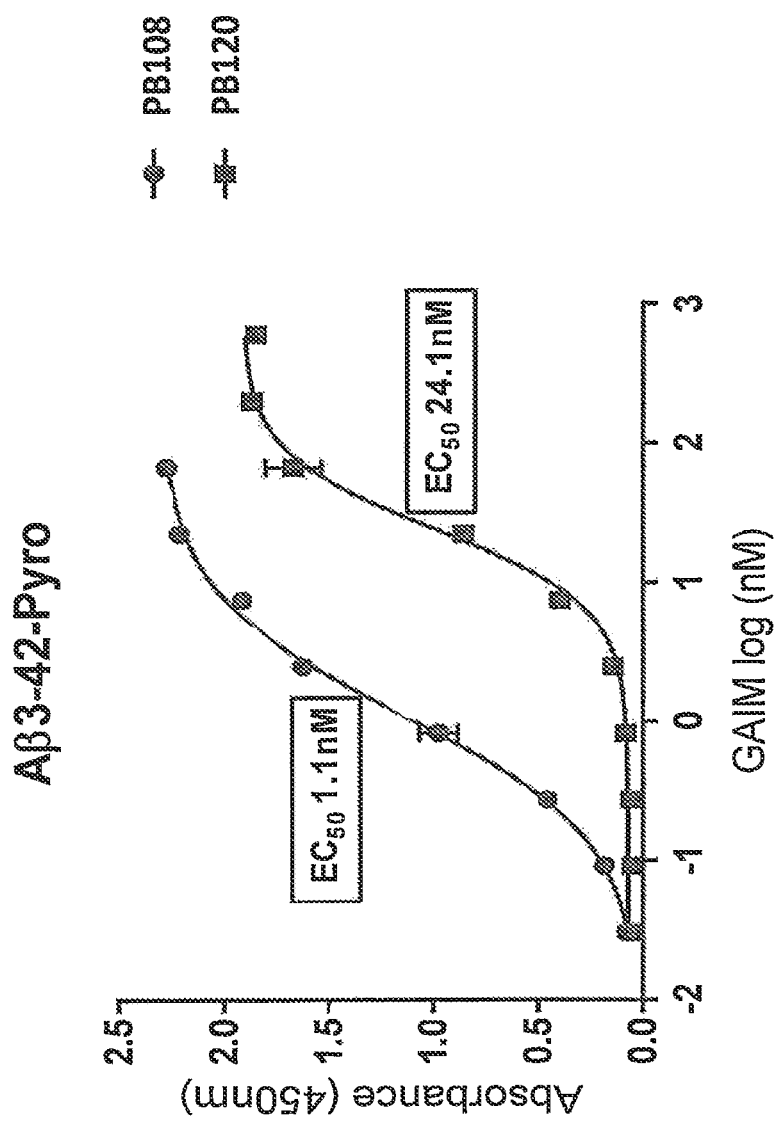
FIGS. 8A-8D shows binding of a representative open-stabilized GAIM-Ig fusion (circles) to various Aβ fibers, compared to binding of the control scaffold to those Aβ fibers (squares).
Figure 8B:
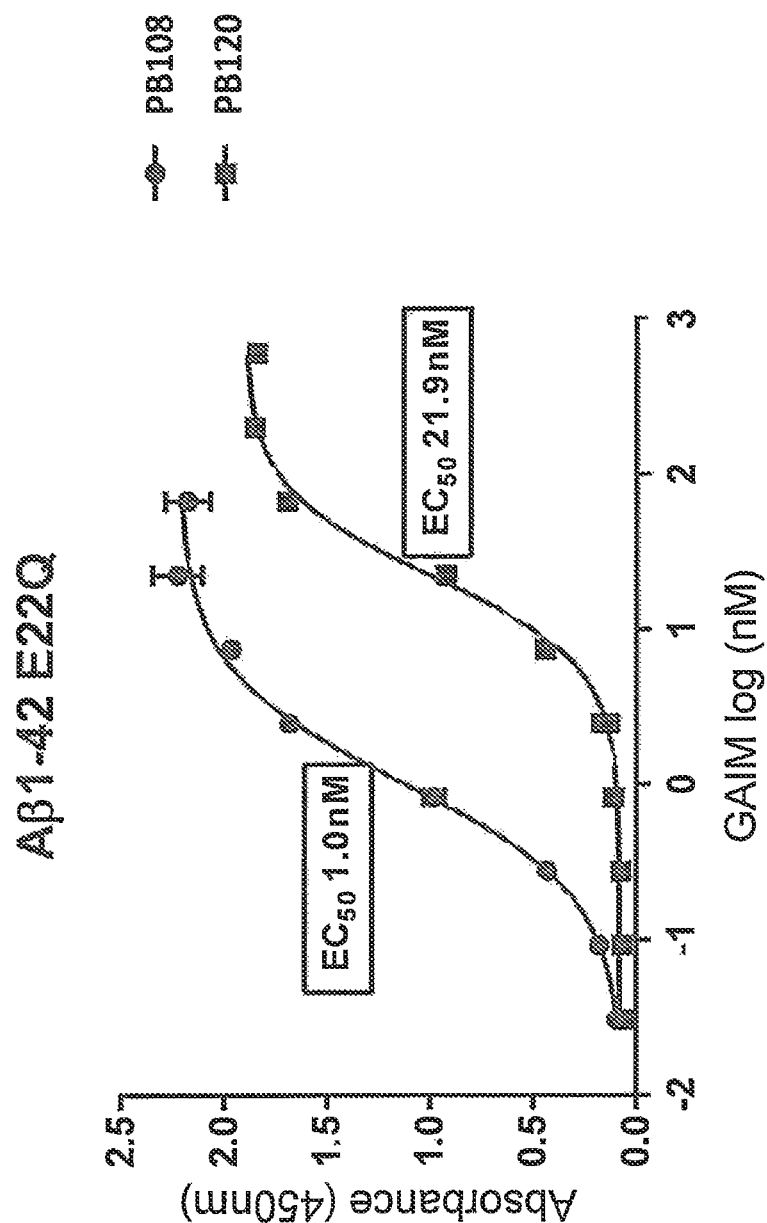
Figure 8C:
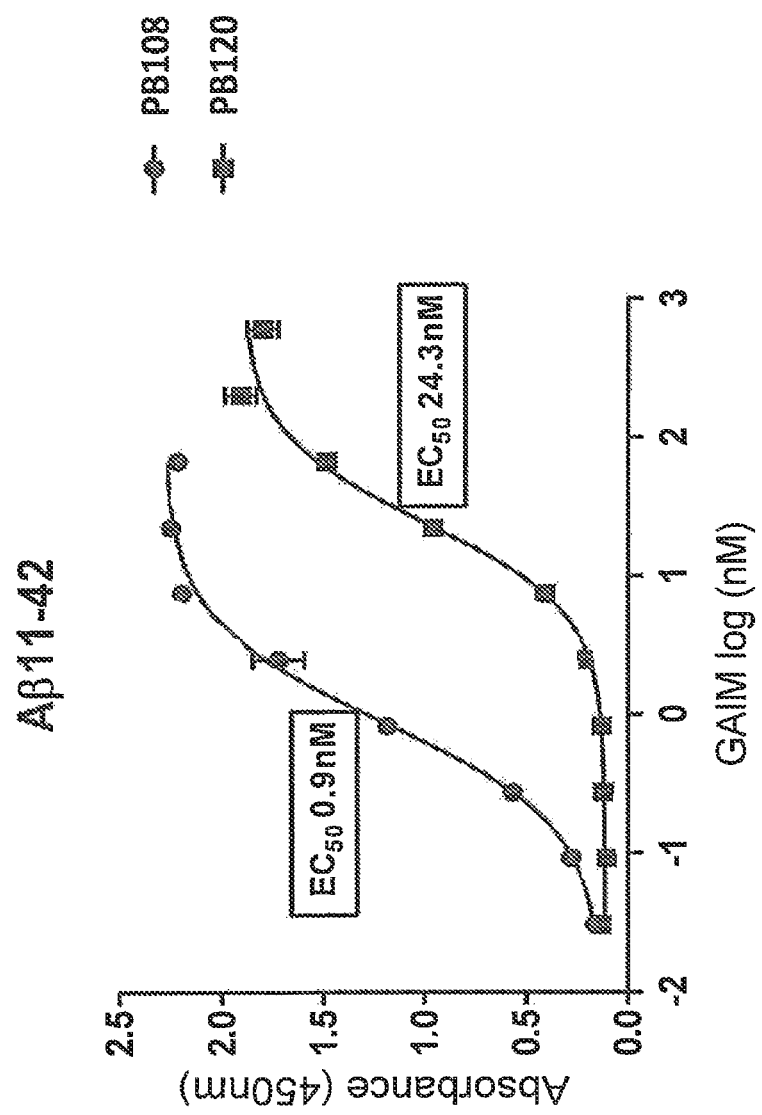
Figure 8D:
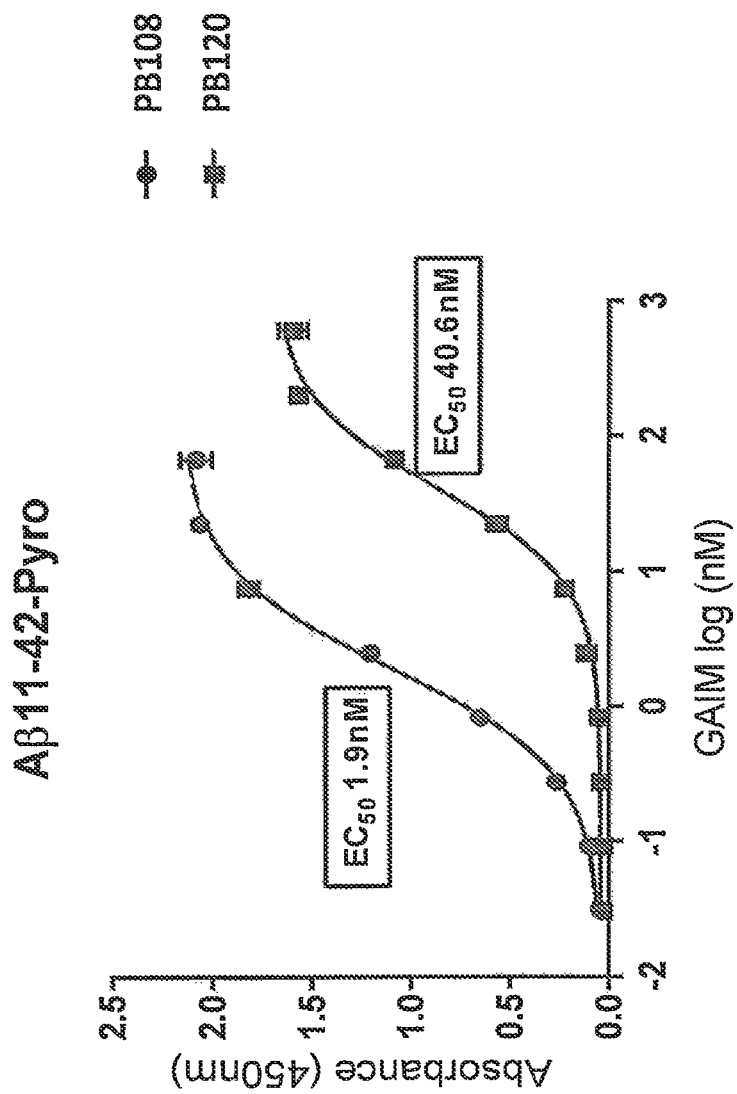

To create a more open conformation of GAIM, the $D_{24}DKTLD_{29}$ (SEQ ID NO:3) loop in N1 (FIG. 3A) was replaced with the homologous sequence EGDS (SEQ ID NO:4) from the filamentous phage IF1 and tested in combination with N2-stabilizing mutations (e.g., at one or more turns/loops indicated in FIG. 3C). The presumed open and N2-stabilized GAIM variants were tested for protein quality and amyloid-binding activity. All open-stabilized variants display improved fiber-binding activity with $EC_{50}$<1.5 nM; consistent with a more exposed and accessible amyloid fiber-binding site (FIG. 7B). One exception was the EGDS (SEQ ID NO: 4) variant with a super stabilized N2 (PB113; SEQ ID NO:17; Tm1=52.7° C.), containing all three N2-stabilizing mutations combined ($F_{135}QGN_{138}$, $V_{143}NGV_{146}$, and $Q_{156}GGK_{162}$) (respectively, SEQ ID NOs:8, 9, 10), resulting in a loss of fAβ42 binding activity (FIG. 7B). This could be due to major structural changes in N2 masking the amyloid interaction site(s) in GAIM, either by introducing intra-domain interactions or by over-stabilizing the N2 domain. The open-stabilized variants with increased fiber binding lost the correlation between Tm1 and fAβ42 binding, suggesting an uncoupling of amyloid binding site(s) and N2-stability in these variants. All EGDS-N2 ("EGDS" disclosed as SEQ ID NO: 4) stabilized variants displayed good protein quality by SDS-PAGE and presented as monomers by size exclusion chromatography (SEC). Additionally, there was a shift in retention time by SEC that further indicated a more open GAIM conformer molecule.

Example 9: GAIM-Ig Fusions Target Multiple Amyloids with Diverse Morphologies

Open-stabilized GAIM-Ig fusions were tested for the ability to engage different types and conformations of Aβ aggregates. Various modified Aβ peptides were fibrillized and binding affinities of GAIM-Ig fusions to these aggregates were measured. N-truncated Aβ11-42, Aβ11-42-Pyro, Aβ3-42-Pyro and Aβ1-42-E22Q-Dutch mutation (Levy et al, 1990; Van Broeckhoven et al, 1990) were aggregated under the same conditions as Aβ42 and fiber formation was verified by ThT (FIGS. 8A-8D) and by TEM (data not shown). The aggregates formed using these peptides showed very diverse morphologies. For example, pyro-glu 3-42 forms fibers that have several bends in their structure, E22Q variant forms smooth long fibers and 11-42 peptides form several short fibers. Both the open-stabilized variant PB108 and the scaffold PB120 were found to engage these fibers by ELISA. PB108 showed ~20-fold improved binding to the various aggregates compared to PB120, $EC_{50}$ 0.9-1.9 nM (FIGS. 8A-8D). Similarly superior binding was observed for the other tested open-stabilized GAIM-Ig fusions (Table 2).

TABLE 2

Open-Stabilized GAIM-Ig Fusions Bind and Remodel Amyloid Protein.

| GAIM-Ig Fusion Protein | fAβ42 Binding (nM) | fTauKL Binding (nM) | fAβ42 Remodeling (%) |
|---|---|---|---|
| PB108 | 1 | 15 | 87 |
| PB122 | 1.3 | 24 | 80 |
| PB116 | 0.8 | 7.0 | 82 |
| PB114 | 0.9 | 8.7 | 86 |
| PB109 | 0.8 | 5.2 | 82 |
| PB110 | 0.9 | 7.6 | 92 |
| PB105 | 0.8 | ND* | ND |
| PB127 | 0.8 | ND | ND |

*ND = no data collected

TABLE 3

Open-Stabilized GAIM-Ig Fusions Targets a Variety of Amyloid Proteins.

| Binding Target | PB120 $EC_{50}$ (nM) | PB108 $EC_{50}$ (nM) |
|---|---|---|
| Aβ (1-42) | 18.0 | 0.8 (0.5 nM $K_D$ by SPR) |
| Aβ (11-42) | 24.3 | 0.9 |
| Aβ3-42 PyroE3 | 24.1 | 1.1 |
| Aβ11-42 PyroE11 | 40.6 | 1.9 |
| Aβ1-42 E22Q | 21.9 | 1.0 |
| TauKL | 59 | 14 |
| Wild-type TTR | 105 | 7 |
| LC lambda_1 (variable + constant) | ND* | 24 |
| LC lambda_1 (variable) | ND | 1.3 |
| LC lambda_2 (variable) | ND | 19 |

*ND = no data collected. Binding determined by ELISA unless otherwise indicated.

The ability of open-stabilized GAIM-Ig fusions to bind different types and conformations of amyloid protein is further shown in Tables 2 and 3. For example, both Tables 2 and 3 show binding of open-stabilized GAIM-Ig fusions to Aβ42 and to tauKL with low nanomolar affinity, and Table 3 further demonstrates their binding to morphologically-diverse immunoglobulin light chain (LC) and transthyretin (TTR) aggregates with low nanomolar affinity. These data show superior targeting across a diverse array of amyloid fibers as compared to the control scaffold and are consistent with previous NMR studies showing that GAIM engages the mid and C-terminal sequences in Aβ42 fibers (Krishnan et al. (2014) J Mol Biol, 426:2500-19).

Example 10: GAIM-Ig Fusions Bind Amyloid Protein Specifically

To rule out non-specific binding, GAIM-Ig fusions were tested at high concentrations (1.8 μM, 100-fold higher than the $EC_{50}$ for a true substrate like fAβ42) for off-target binding to other fibrillar species like collagen. Two hundred twenty-five nanograms per well of human collagen (Sigma cat. no. C5483) in D-PBS was immobilized on MaxiSorp® 96-well plates (Thermo Fisher Scientific) for 16 hours at 37° C. followed by blocking in SuperBlock™ (Thermo Fisher Scientific) for 1 hour at room temperature. GAIM-Ig fusion in PBS-Tween (0.05%) was incubated at 37° C. for 1 hour followed by 3×5-minute washes in PBS-Tween (0.05%). Human specific Fc-HRP antibody (Jackson ImmunoResearch, cat. no. 109-035-008) was added 1:5000 in PBS-Tween (0.05%) for 45 minutes at 37° C. followed by 3×5-minute washes in PBS-Tween (0.05%) and 2×5-minute washes in PBS. The signal was developed with TMB solution (Sigma), the reaction was stopped by the addition of 0.25 N HCl and the absorbance at 450 nm was recorded with a Tecan Infinite® M1000 PRO plate reader. GAIM-Ig fusions showed minimal binding to non-amyloid substrates by ELISA (Krishnan et al. (2014) J Mol Biol, 426:2500-19).

Example 11: Open-stabilized GAIM-Ig Fusions Exhibit Enhanced Remodeling of Aβ Fibers Remodeling assays were carried out in low retention microfuge tubes (Fisher Scientific 02-681-320). Buffers used in these assays contain 0.05% sodium azide to prevent microbial growth. To make sure there was no protease contamination in any sample, all remodeled complexes were run on an SDS-PAGE gel and checked for any degradation. For assays using <1 μM fibers, protein quality was instead confirmed using western blot analysis.

Aβ42 fibers (2.5 μM) were co-incubated with or without GAIM-Ig fusion variants for three days at 37° C. Aliquots of the complexes were then incubated with varying concentrations of urea. The ThT fluorescence of the complexes in urea was plotted against the urea concentration. Remodeling efficiency at a fixed urea concentration was plotted as percent loss in ThT fluorescence compared to fibers without any GAIM-Ig fusion treatment.

Figure 10B:
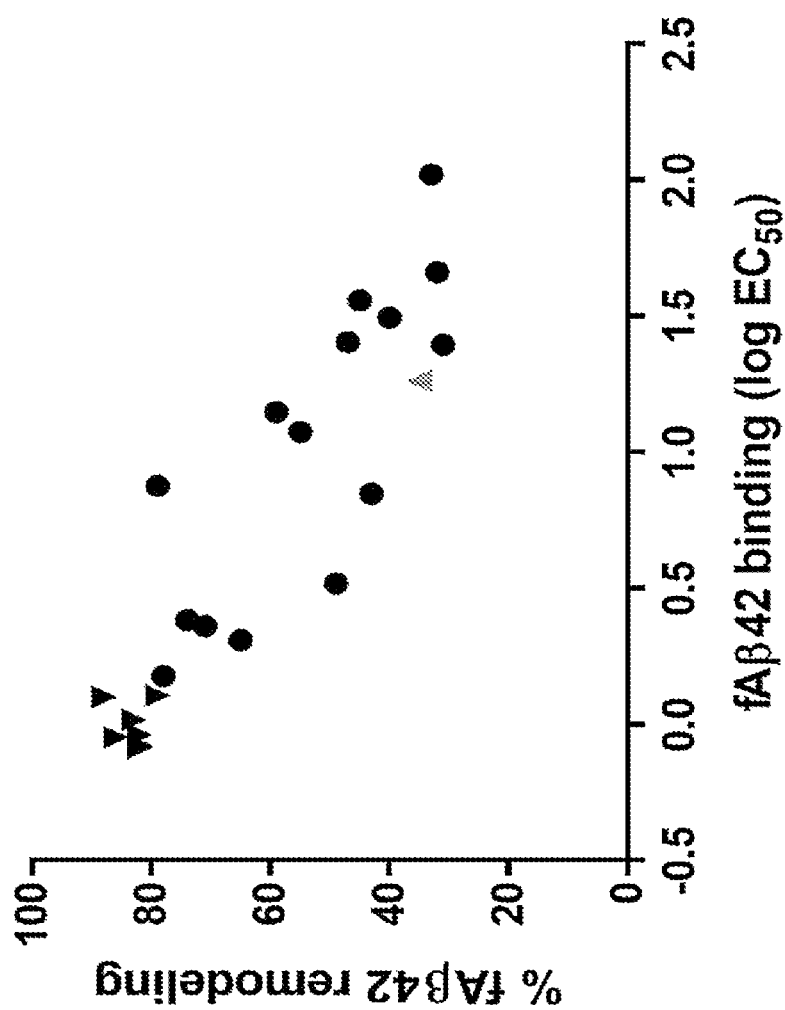

GAIM-Ig fusions with different Aβ42 fiber binding potencies were selected to determine if the remodeling efficiencies depend on the binding potencies and open conformational state. FIG. 10A shows remodeling efficiencies of different GAIM fusions incubated with Aβ42 fibers under identical conditions and concentrations. Open-stabilized variants with low nanomolar fAβ42 binding showed a 2-fold to 3-fold increase in remodeling activity, with an average remodeling activity of 83% compared to the control scaffold (35%). FIG. 10B reveals a positive correlation between altered fAβ42-binding and remodeling activity, such that GAIM-Ig fusions with superior As binding also exhibit superior remodeling activity.

Figure 10C:
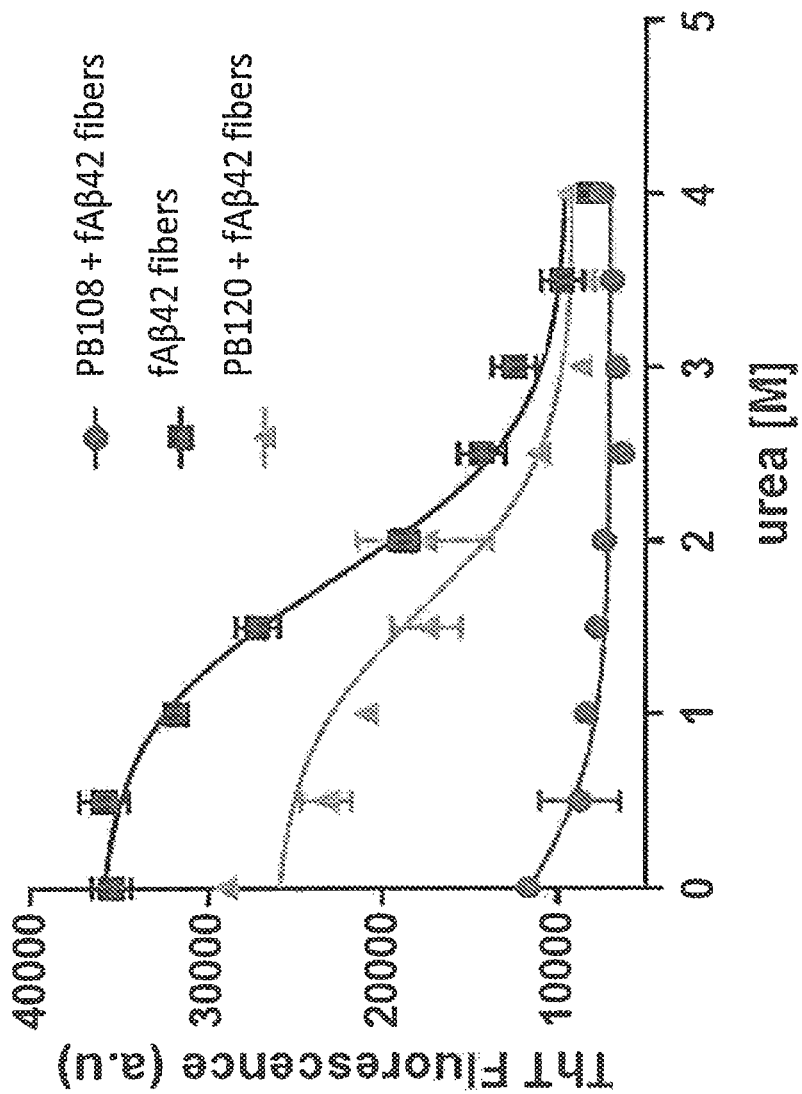
Figure 10D:
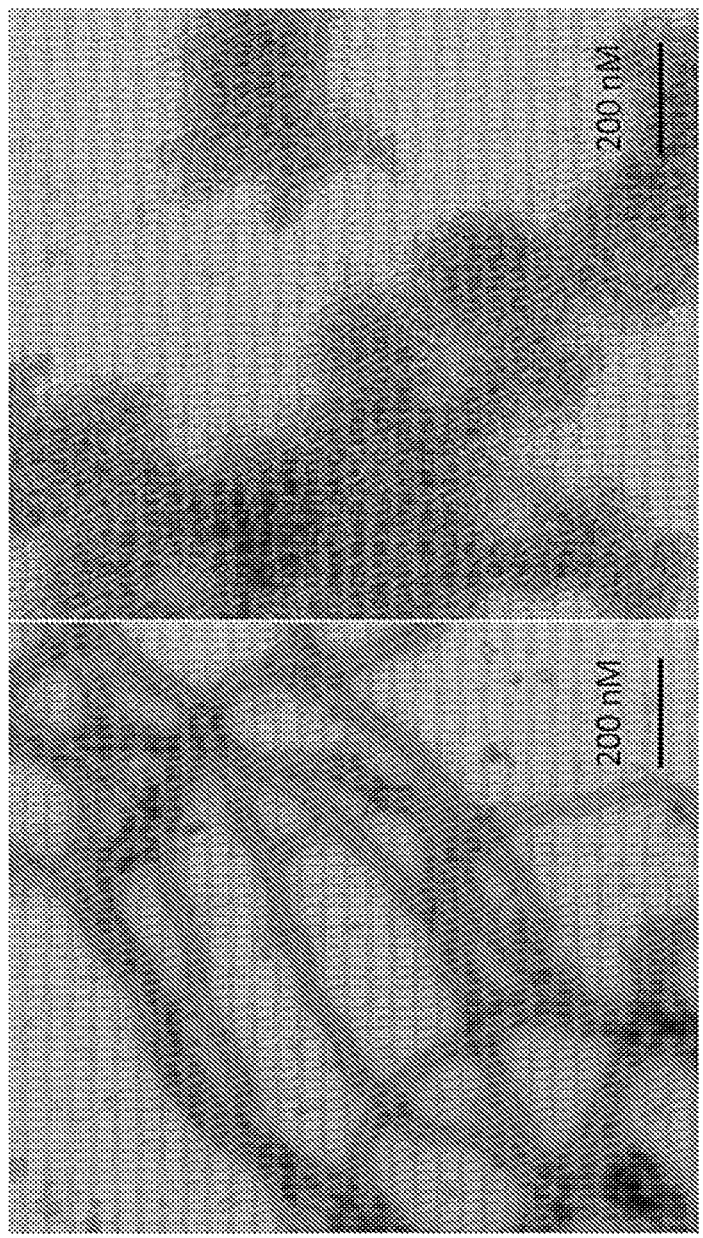

FIGS. 10A-10C, as well as transmission electron microscopy data (see Example 13; FIG. 10D), further demonstrate that open-stabilized GAIM-Ig fusions remodel amyloid fibers to cause a loss of fibrillar architecture, as opposed to merely sticking to and masking fibrillar structures. For example, when incubated in increasing concentrations of urea but without exposure to a GAIM-Ig fusion, Aβ42 fibers resisted denaturation and showed less than 10% structural change in 1 M urea as measured by ThT fluorescence (FIG. 10C). In higher urea concentrations, ThT fluorescence dropped dramatically, suggesting loss of fibrillar structure. In contrast, fibers treated with sub-stoichiometric amounts of GAIM-Ig fusion began to show 30-90% reduced ThT binding at 1 M urea. This finding suggests that the GAIM-Ig fusions bind and alter the fibrillar structures to a state that cannot bind ThT and that GAIM remodeling activity varies between different GAIM Ig-fusions, with open-stabilized GAIM-Ig fusions demonstrating high remodeling activity.

Example 12: Open-stabilized GAIM-Ig Fusions Exhibit Enhanced Remodeling of TauK18P301L Fibers Remodeling assays were also performed by co-incubating Tau-K18P301 L fibers with GAIM-Ig fusions to demonstrate that remodeling of aggregates is generic to amyloid protein.

Remodeling assays were carried out in low retention microfuge tubes (Fisher Scientific 02-681-320). Buffers used in these assays contain 0.05% sodium azide to prevent microbial growth. To make sure there was no protease contamination in any sample, all remodeled complexes were run on an SDS-PAGE gel and checked for any degradation. For assays using <1 µM fibers, protein quality was instead confirmed using western blot analysis.

Unlike fAβ42 fibers, Tau-k18P301 L fibers readily dissolve in low concentration urea solutions. Thus, the remodeling efficiencies of GAIM-Ig fusions against Tau-K18P301 L was investigated using sarkosyl solubility assays. TauK18P301L fibers (1 µM) were co-incubated with or without GAIM-Ig-fusion variants at 37° C. for 5 days. Fibers and the complexes were incubated with or without 1% sarkosyl for 15 minutes and spun down at 100,000 g for 30 minutes. The supernatant from each sample was carefully removed and loaded on a 4-12% NuPAGE® gels (Invitrogen). Proteins were transferred to a Nitrocellulose membrane and probed for TauK18P301L. The percent remodeling was calculated by quantifying the gel bands using a Biorad Chemidoc™ system.

Figure 11A:
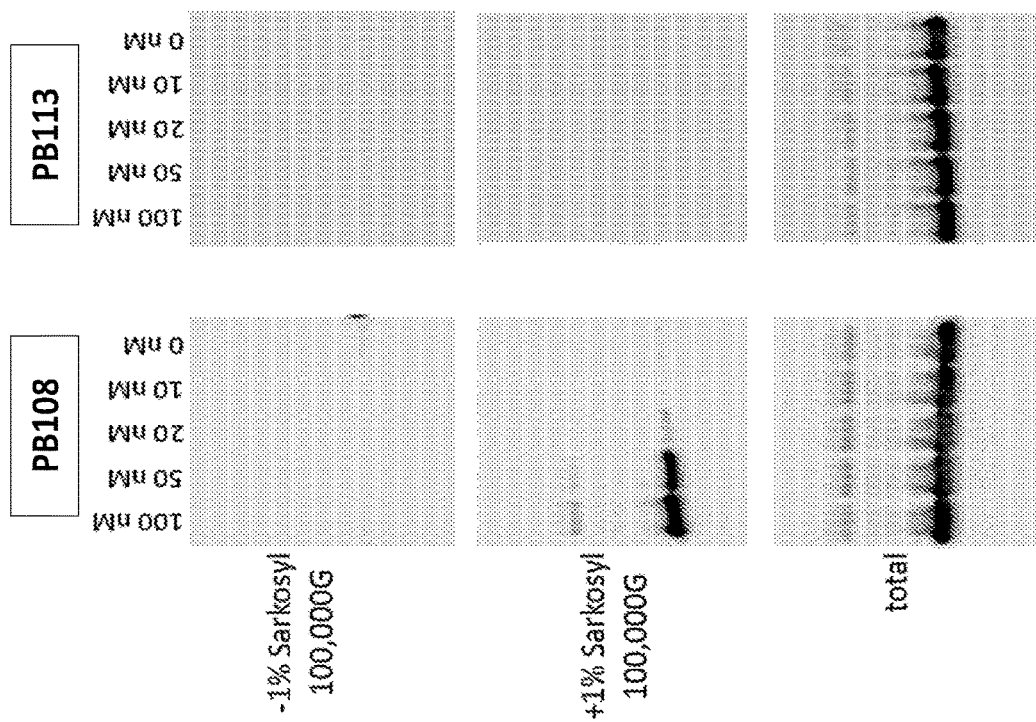
FIGS. 11A-11C address the remodeling efficiencies of different GAIM-Ig fusion proteins incubated with tau fibers.
Figure 11B:
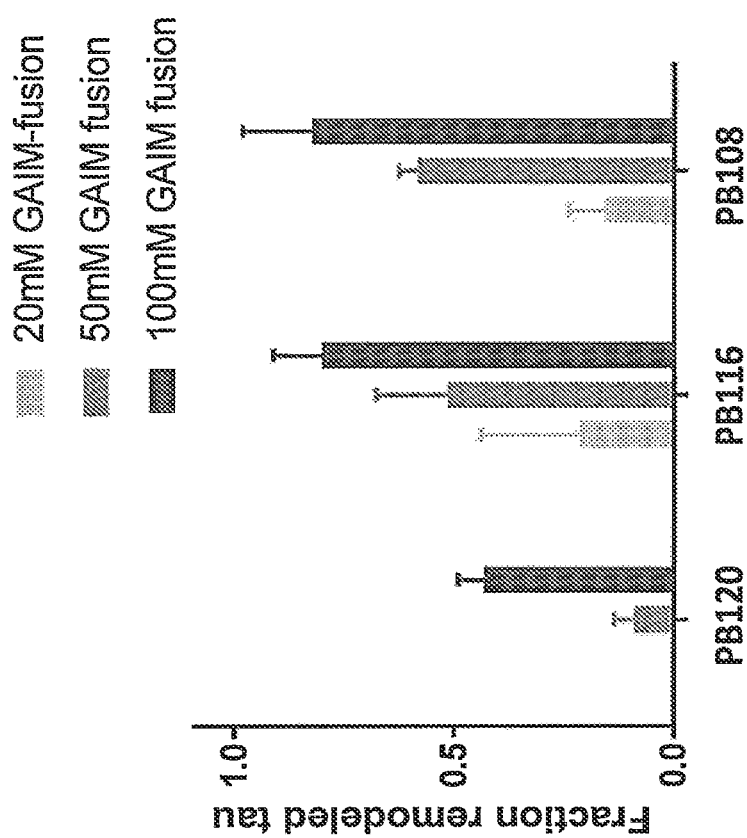

Fibers assembled in vitro using Tau-K18P310L (not exposed to a GAIM-Ig fusion) showed resistance to dissolution when incubated with 1% sarkosyl. GAIM-Ig fusion-treated Tau-K18P301 L fibers dissolved in 1% sarkosyl more readily than untreated fibers (FIG. 11A), indicating that these fibers can also be remodeled like fAβ42. When incubated with varying concentrations of GAIM-Ig fusions, these fibers dissolved in a concentration-dependent manner (FIG. 11B).

The remodeling efficiency of PB120 were compared with the remodeling efficiencies of open-stabilized GAIM IgG fusions. PB113, a super-stabilized, disulfide-free GAIM with reduced infectivity (Kather et al., 2005, J Mol Biol, 354:666-78) has no binding activity to Aβ1-42 or Tau-K18P301L fibers (data not shown) and was added as a negative control. The open-stabilized GAIM-Ig fusion proteins showed enhanced remodeling activities as compared to PB120 (FIG. 11B), whereas PB113 had no remodeling activity (FIG. 11A).

We investigated whether GAIM fusions remodel Tau-K18P301L fibers and release soluble TauK18P301L species when we co-incubate the samples. At GAIM fusion concentrations yielding potent remodeling (e.g., 10-250 nM), there were no soluble species seen in supernatant of complexes that have not been subjected to sarkosyl treatment (FIG. 11A), suggesting that the remodeled material does not liberate soluble TauK18P301L species or monomers upon binding GAIM fusions.

Figure 11C:
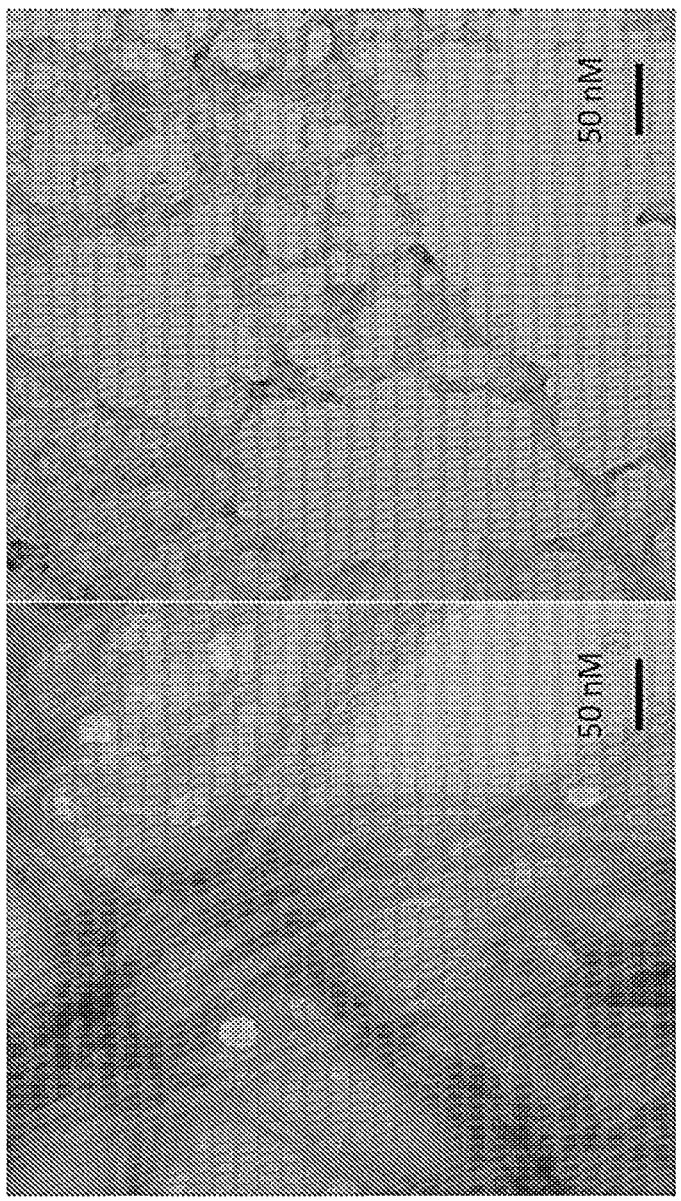

Example 13: Open-Stabilized GAIM-Ig Fusions Cause Amyloid Fibers to Lose Fibrillar Architecture Aβ1-42 fibers (15 µl of 20 µM sample) were applied on carbon coated copper grids (TedPella cat #01844-F). Samples were then washed gently with 0.5 ml water, inverted and floated over a drop of 2% uranyl acetate solution. After 30 seconds, the grids were removed and dried by wicking out the excess liquid from the edge of the grids using a filter paper. FEI Tecnai™ Spirit TEM was used to image the fibers. FIG. 10D shows a representative TEM images of Aβ42 fibers incubated with sub-stoichiometric open-stabilized GAIM-Ig fusion. When exposed to open-stabilize GAIM-Ig fusions, Aβ42 fibers lost their fibrillar architecture (FIG. 10D). Similarly, TEM analysis showed that Tau-K18P301L fibers lost their characteristic fibrillar conformation when co-incubated with an open-stabilized GAIM-Ig fusion (FIG. 11C).

Example 14: Open-Stabilized GAIM-Ig Fusions Exhibit Increased Inhibition of Amyloid Aggregation Open-stabilized GAIM-Ig fusion proteins were tested for assembly inhibition activity by co-incubation with Aβ42 monomers at 37° C. for 10 hours. Amyloid fiber formation was followed by ThT fluorescence and compared to fiber formation without GAIM as well as in the presence of the negative control PB113.

One hundred micrograms of HFIP-treated A31-42 (rPeptide) monomeric sample was dissolved in 80 µl DMSO, mixed thoroughly by pipetting, vortexed, and diluted in 5.4 mL D-PBS to a final Aβ1-42 concentration of 4.04 µM. GAIM-Ig fusion samples were diluted in PBS to intermediate stock solutions of 10, 2.5, 0.63, and 0.16 µM. Eighty microliters Aβ1-42 monomer solution was distributed in each well of a black, round bottom 96-well plate (LVL, cat. no. 225.LS.PP). Ten microliters of each GAIM-Ig fusion stock solution were added to wells containing Aβ1-42, followed by the addition of 10 µl ThT (33 µM in PBS), for a final concentration of 3.2 µM Aβ1-42 and 3.3 µM ThT per well. The plate was sealed with transparent film and ThT fluorescence at 430/485 nm (Ex/Em) was recorded every 20 minutes for 14 hours in a Tecan Infinite® M1000 PRO plate reader while incubated at 37° C. with 3-second vertical shaking every 20 minutes. The percentage of Aβ42 aggregation for each GAIM-Ig fusion concentration was calculated relative to non-treated Aβ42 wells (positive control wells).

Figure 12A:
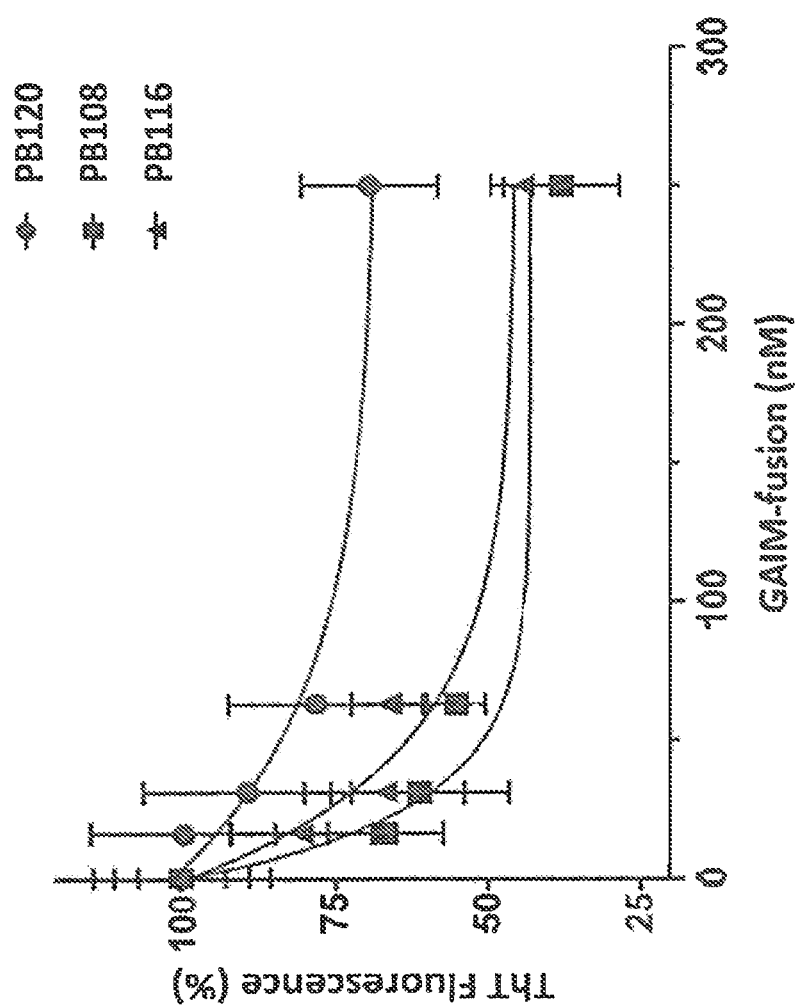
Figure 12B:
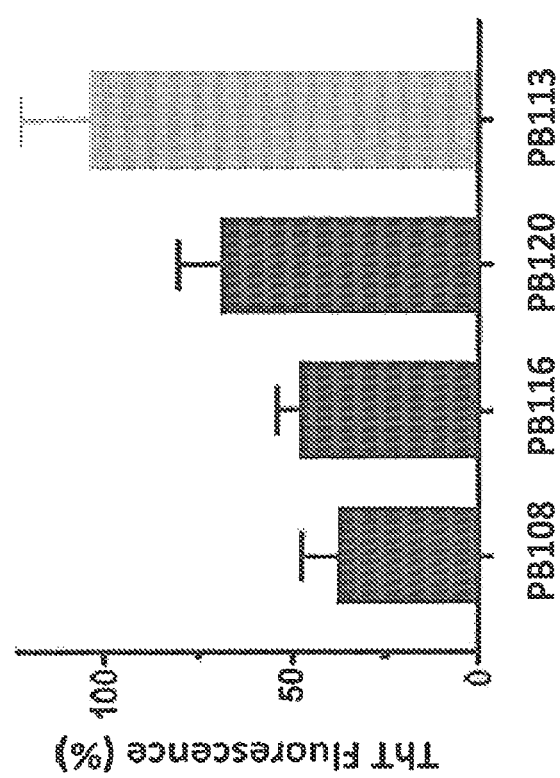

Open-stabilized GAIM-Ig fusions showed dose-dependent assembly inhibition when added for 10 hours at the indicated concentrations (FIG. 12A). The open-stabilized fusions further showed increased assembly inhibition activity compared to the control scaffold, PB120 (FIGS. 12A-12B). For example, at 250 nM, representative open-stabilized GAIM-Ig fusions PB108 and PB116 showed a 40-20% increase in blocking fiber formation compared to PB120 (FIG. 12B). The ability of sub-stoichiometric amounts of open-stabilized GAIM-Ig fusions to potently block amyloid fibril formation suggests that the fusions block amyloid fiber formation by binding to core R strands in the growing fiber or seeds involved in nucleation dependent fiber assembly (Krishnan et al. (2014) J Mol Biol, 426:2500-19).

Figure 12C:
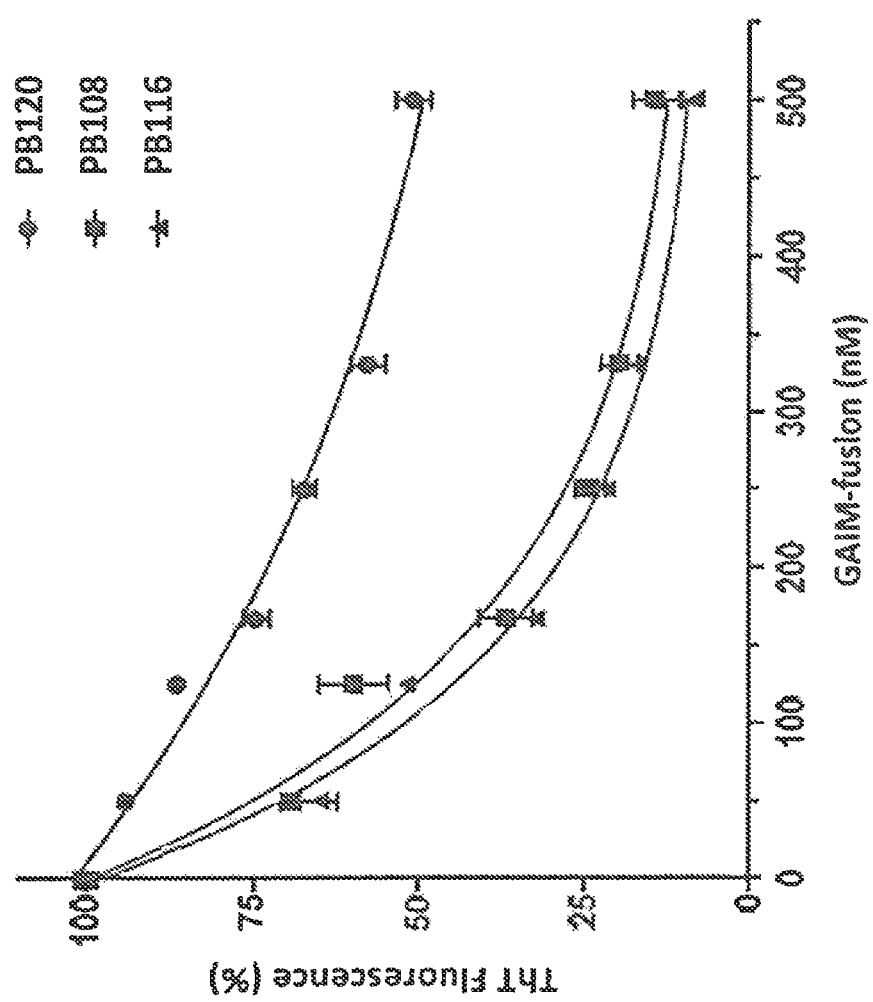

Similarly, open-stabilized GAIM-Ig fusions showed dose-dependent assembly inhibition against tau fibers (FIG. 12C). TauK18P301L assembly reactions were set by incubating 10 µM tau monomers in 0.1 M sodium acetate pH 7.0 buffer with 2 µM low-molecular weight heparin (Fisher Scientific) at 37° C. for 3 days in the presence of varying concentrations of GAIM fusions (0-500 nM). ThT fluorescence of the assembly reactions were recorded by diluting samples to 1 µM into a 5 µM ThT solution. Inhibitory effects of GAIM on TauK18P301L assembly were calculated by comparing the assembly of TauK18P301L without GAIM fusion.

In vitro fiber assembly of full-length tau or truncated sequences such as MTBR or K18 requires the presence of heparin to promote nucleation and subsequent assembly. The tested GAIM fusions inhibited ftauKL assembly in the presence of heparin. Moreover, the open-stablized GAIM fusions blocked nucleation three-fold to five-fold better as compared to PB120 (FIG. 12C-12D). Together, these results indicate that open-stabilized GAIM fusions bind both Aβ and tau on-pathway intermediates and inhibit assembly of amyloid aggregates.

```
                              SEQUENCE LISTING

Sequence total quantity: 54
SEQ ID NO: 1             moltype = AA  length = 32
FEATURE                  Location/Qualifiers
REGION                   1..32
                         note = source = /note="Description of Artificial Sequence:
                          Synthetic polypeptide"
source                   1..32
                         mol_type = protein
                         organism = synthetic construct
SEQUENCE: 1
AETVESCLAK PHTENSFTNV WKDDKTLDRY AN                                              32

SEQ ID NO: 2             moltype = AA  length = 30
FEATURE                  Location/Qualifiers
REGION                   1..30
                         note = source = /note="Description of Artificial Sequence:
                          Synthetic polypeptide"
source                   1..30
                         mol_type = protein
                         organism = synthetic construct
SEQUENCE: 2
ATTDAECLSK PAFDGTLSNV WKEGDSRYAN                                                 30

SEQ ID NO: 3             moltype = AA  length = 6
FEATURE                  Location/Qualifiers
REGION                   1..6
                         note = source = /note="Description of Artificial Sequence:
                          Synthetic peptide"
source                   1..6
                         mol_type = protein
                         organism = synthetic construct
SEQUENCE: 3
DDKTLD                                                                            6

SEQ ID NO: 4             moltype = AA  length = 4
FEATURE                  Location/Qualifiers
REGION                   1..4
                         note = source = /note="Description of Artificial Sequence:
                          Synthetic peptide"
source                   1..4
                         mol_type = protein
                         organism = synthetic construct
SEQUENCE: 4
EGDS                                                                              4

SEQ ID NO: 5             moltype = AA  length = 4
FEATURE                  Location/Qualifiers
REGION                   1..4
                         note = source = /note="Description of Artificial Sequence:
                          Synthetic peptide"
source                   1..4
                         mol_type = protein
                         organism = synthetic construct
SEQUENCE: 5
FQNN                                                                              4

SEQ ID NO: 6             moltype = AA  length = 4
FEATURE                  Location/Qualifiers
REGION                   1..4
                         note = source = /note="Description of Artificial Sequence:
                          Synthetic peptide"
source                   1..4
                         mol_type = protein
                         organism = synthetic construct
SEQUENCE: 6
RQGA                                                                              4

SEQ ID NO: 7             moltype = AA  length = 7
FEATURE                  Location/Qualifiers
REGION                   1..7
```

|  | note = source = /note="Description of Artificial Sequence: Synthetic peptide" |
|---|---|
| source | 1..7 |
|  | mol_type = protein |
|  | organism = synthetic construct |

SEQUENCE: 7
QGTDPVK                                                                          7

| SEQ ID NO: 8 | moltype = AA   length = 4 |
|---|---|
| FEATURE | Location/Qualifiers |
| REGION | 1..4 |
|  | note = source = /note="Description of Artificial Sequence: Synthetic peptide" |
| source | 1..4 |
|  | mol_type = protein |
|  | organism = synthetic construct |

SEQUENCE: 8
FQGN                                                                             4

| SEQ ID NO: 9 | moltype = AA   length = 4 |
|---|---|
| FEATURE | Location/Qualifiers |
| REGION | 1..4 |
|  | note = source = /note="Description of Artificial Sequence: Synthetic peptide" |
| source | 1..4 |
|  | mol_type = protein |
|  | organism = synthetic construct |

SEQUENCE: 9
VNGV                                                                             4

| SEQ ID NO: 10 | moltype = AA   length = 4 |
|---|---|
| FEATURE | Location/Qualifiers |
| REGION | 1..4 |
|  | note = source = /note="Description of Artificial Sequence: Synthetic peptide" |
| source | 1..4 |
|  | mol_type = protein |
|  | organism = synthetic construct |

SEQUENCE: 10
QGGK                                                                             4

| SEQ ID NO: 11 | moltype = AA   length = 487 |
|---|---|
| FEATURE | Location/Qualifiers |
| REGION | 1..487 |
|  | note = source = /note="Description of Artificial Sequence: Synthetic polypeptide" |
| source | 1..487 |
|  | mol_type = protein |
|  | organism = synthetic construct |

SEQUENCE: 11
MAETVESCLA KPHTENSFTN VWKDDKTLDR YANYEGCLWN AGGVVVCTGD ETQCYGTWVP   60
IGLAIPENEG GGSEGGGSEG GGSEGGGTKP PEYGDTPIPG YTYINPLDGT YPPGTEQNPA  120
NPNPSLEESQ PLNTFMFQNN RFRNRQGALT VYTGTFTQGT DPVKTYYQYT PVSSRAMYDA  180
YWNGKFRDCA FHSGFNEDPF VCEYQGQSSD LPQPPANAGG ESGGGSGGGS EGGSEGGGS   240
EGGGSEGGGS GGGSGSGARS DKTHTCPPCP APELLGGPSV FLFPPKPKDT LMISRTPEVT  300
CVVVDVSHED PEVKFNWYVD GVEVHNAKTK PREEQYNSTY RVVSVLTVLH QDWLNGKEYK  360
CKVSNKALPA PIEKTISKAK GQPREPQVYT LPPSREEMTK NQVSLTCLVK GFYPSDIAVE  420
WESNGQPENN YKTTPPVLDS DGSFFLYSKL TVDKSRWQQG NVFSCSVMHE ALHNHYTQKS  480
LSLSPGK                                                           487

| SEQ ID NO: 12 | moltype = AA   length = 257 |
|---|---|
| FEATURE | Location/Qualifiers |
| REGION | 1..257 |
|  | note = source = /note="Description of Artificial Sequence: Synthetic polypeptide" |
| source | 1..257 |
|  | mol_type = protein |
|  | organism = synthetic construct |

SEQUENCE: 12
MAETVESCLA KPHTENSFTN VWKDDKTLDR YANYEGCLWN AGGVVVCTGD ETQCYGTWVP   60
IGLAIPENEG GGSEGGGSEG GGSEGGGTKP PEYGDTPIPG YTYINPLDGT YPPGTEQNPA  120
NPNPSLEESQ PLNTFMFQNN RFRNRQGALT VYTGTFTQGT DPVKTYYQYT PVSSRAMYDA  180
YWNGKFRDCA FHSGFNEDPF VCEYQGQSSD LPQPPANAGG ESGGGSGGGS EGGSEGGGS   240
EGGGSEGGGS GGGSGSG                                                257

| SEQ ID NO: 13 | moltype = AA   length = 487 |
|---|---|
| FEATURE | Location/Qualifiers |
| REGION | 1..487 |
|  | note = source = /note="Description of Artificial Sequence: |

```
                            Synthetic polypeptide"
source                  1..487
                        mol_type = protein
                        organism = synthetic construct
SEQUENCE: 13
MAETVESCLA KPHTENSFTN VWKDDKTLDR YANYEGCLWN AGGVVVCTGD ETQCYGHWVP  60
IGLAIPENEG GGSEGGGSEG GGSEGGGTKP PEYGDTPIPG YTYINPLDGT YPPGTEQNPA  120
NPNPSLEESQ PLNTFMFQNN RFRNRQGALT VYTGTFTQGT DPVKTYYQYT PVSSRAMYDA  180
YWNGKFRDCA FHSGFNEDPF VCEYQGQSSD LPQPPANAGG ESGGGSGGGS EGGGSEGGGS  240
EGGGSEGGGS GGGSGSGARS DKTHTCPPCP APELLGGPSV FLFPPKPKDT LMISRTPEVT  300
CVVVDVSHED PEVKFNWYVD GVEVHNAKTK PREEQYNSTY RVVSVLTVLH QDWLNGKEYK  360
CKVSNKALPA PIEKTISKAK GQPREPQVYT LPPSREEMTK NQVSLTCLVK GFYPSDIAVE  420
WESNGQPENN YKTTPPVLDS DGSFFLYSKL TVDKSRWQQG NVFSCSVMHE ALHNHYTQKS  480
LSLSPGK                                                           487

SEQ ID NO: 14           moltype = AA  length = 257
FEATURE                 Location/Qualifiers
REGION                  1..257
                        note = source = /note="Description of Artificial Sequence:
                            Synthetic polypeptide"
source                  1..257
                        mol_type = protein
                        organism = synthetic construct
SEQUENCE: 14
MAETVESCLA KPHTENSFTN VWKDDKTLDR YANYEGCLWN AGGVVVCTGD ETQCYGHWVP  60
IGLAIPENEG GGSEGGGSEG GGSEGGGTKP PEYGDTPIPG YTYINPLDGT YPPGTEQNPA  120
NPNPSLEESQ PLNTFMFQNN RFRNRQGALT VYTGTFTQGT DPVKTYYQYT PVSSRAMYDA  180
YWNGKFRDCA FHSGFNEDPF VCEYQGQSSD LPQPPANAGG ESGGGSGGGS EGGGSEGGGS  240
EGGGSEGGGS GGGSGSG                                                257

SEQ ID NO: 15           moltype = AA  length = 485
FEATURE                 Location/Qualifiers
REGION                  1..485
                        note = source = /note="Description of Artificial Sequence:
                            Synthetic polypeptide"
source                  1..485
                        mol_type = protein
                        organism = synthetic construct
SEQUENCE: 15
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP  120
NPSLEESQPL NTFMFQNNRF RNRQGALTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSGARSDK THTCPPCPAP ELLGGPSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PSREEMTKNQ VSLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 16           moltype = AA  length = 255
FEATURE                 Location/Qualifiers
REGION                  1..255
                        note = source = /note="Description of Artificial Sequence:
                            Synthetic polypeptide"
source                  1..255
                        mol_type = protein
                        organism = synthetic construct
SEQUENCE: 16
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP  120
NPSLEESQPL NTFMFQNNRF RNRQGALTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSG                                                  255

SEQ ID NO: 17           moltype = AA  length = 487
FEATURE                 Location/Qualifiers
REGION                  1..487
                        note = source = /note="Description of Artificial Sequence:
                            Synthetic polypeptide"
source                  1..487
                        mol_type = protein
                        organism = synthetic construct
SEQUENCE: 17
MAETVESSLA KPHIEGSFTN VWKDDKTLDW YANYEGILWK ATGVVVITGD ETQVYAIWVP  60
VGLAIPENEG GGSEGGGSEG GGSEGGGTKP PEYGDTPIPG YIYINPLDGT YPPGTEQNPA  120
NPNPSLEESH PLNTFMFQGN RFRNRQGALT VYTGTFTQGT DPVKTYYQYT PVSSRAMYDA  180
YWNGKFRDVA FHSGFNEDPL VAEYQGQLSY LPQPPANAGG ESGGGSGGGS EGGGSEGGGS  240
EGGGSEGGGS GGGSGSGARS DKTHTCPPCP APELLGGPSV FLFPPKPKDT LMISRTPEVT  300
CVVVDVSHED PEVKFNWYVD GVEVHNAKTK PREEQYNSTY RVVSVLTVLH QDWLNGKEYK  360
```

```
CKVSNKALPA PIEKTISKAK GQPREPQVYT LPPSREEMTK NQVSLTCLVK GFYPSDIAVE    420
WESNGQPENN YKTTPPVLDS DGSFFLYSKL TVDKSRWQQG NVFSCSVMHE ALHNHYTQKS    480
LSLSPGK                                                             487

SEQ ID NO: 18           moltype = AA  length = 257
FEATURE                 Location/Qualifiers
REGION                  1..257
                        note = source = /note="Description of Artificial Sequence:
                         Synthetic polypeptide"
source                  1..257
                        mol_type = protein
                        organism = synthetic construct
SEQUENCE: 18
MAETVESSLA KPHIEGSFTN VWKDDKTLDW YANYEGILWK ATGVVVITGD ETQVYAIWVP    60
VGLAIPENEG GGSEGGGSEG GGSEGGGTKP PEYGDTPIPG YIYINPLDGT YPPGTEQNPA    120
NPNPSLEESH PLNTFMFQGN RFRNRQGALT VYTGTFTQGT DPVKTYYQYT PVSSRAMYDA    180
YWNGKFRDVA FHSGFNEDPL VAEYQGQLSY LPQPPANAGG ESGGGSGGGS EGGGSEGGGS    240
EGGGSEGGGS GGGSGSG                                                  257

SEQ ID NO: 19           moltype = AA  length = 255
FEATURE                 Location/Qualifiers
REGION                  1..255
                        note = source = /note="Description of Artificial Sequence:
                         Synthetic polypeptide"
source                  1..255
                        mol_type = protein
                        organism = synthetic construct
SEQUENCE: 19
MAETVESCLA KPHTENSFTN VWKEGDSRYA NYEGCLWNAG GVVVCTGDET QCYGHWVPIG    60
LAIPENEGGG SEGGGSEGGG SEGGGTKPPE YGDTPIPGYT YINPLDGTYP PGTEQNPANP    120
NPSLEESQPL NTFMFQGNRF RNRQGALTVY TGTFTQGTDP VKTYYQYTPV SSRAMYDAYW    180
NGKFRDCAFH SGFNEDPFVC EYQGQSSDLP QPPANAGGES GGGSGGGSEG GGSEGGGSEG    240
GGSEGGGSGG GSGSG                                                    255

SEQ ID NO: 20           moltype = AA  length = 255
FEATURE                 Location/Qualifiers
REGION                  1..255
                        note = source = /note="Description of Artificial Sequence:
                         Synthetic polypeptide"
source                  1..255
                        mol_type = protein
                        organism = synthetic construct
SEQUENCE: 20
MAETVESCLA KPHTENSFTN VWKEGDSRYA NYEGCLWNAG GVVVCTGDET QCYGHWVPIG    60
LAIPENEGGG SEGGGSEGGG SEGGGTKPPE YGDTPIPGYT YINPLDGTYP PGTEQNPANP    120
NPSLEESQPL NTFMFQNNRF RNVNGVLTVY TGTFTQGTDP VKTYYQYTPV SSRAMYDAYW    180
NGKFRDCAFH SGFNEDPFVC EYQGQSSDLP QPPANAGGES GGGSGGGSEG GGSEGGGSEG    240
GGSEGGGSGG GSGSG                                                    255

SEQ ID NO: 21           moltype = AA  length = 255
FEATURE                 Location/Qualifiers
REGION                  1..255
                        note = source = /note="Description of Artificial Sequence:
                         Synthetic polypeptide"
source                  1..255
                        mol_type = protein
                        organism = synthetic construct
SEQUENCE: 21
MAETVESCLA KPHTENSFTN VWKEGDSRYA NYEGCLWNAG GVVVCTGDET QCYGHWVPIG    60
LAIPENEGGG SEGGGSEGGG SEGGGTKPPE YGDTPIPGYT YINPLDGTYP PGTEQNPANP    120
NPSLEESQPL NTFMFQGNRF RARQGALTVY TGTFTQGTDP VKTYYQYTPV SSRAMYDAYW    180
NGKFRDCAFH SGFNEDPFVC EYQGQSSDLP QPPANAGGES GGGSGGGSEG GGSEGGGSEG    240
GGSEGGGSGG GSGSG                                                    255

SEQ ID NO: 22           moltype = AA  length = 255
FEATURE                 Location/Qualifiers
REGION                  1..255
                        note = source = /note="Description of Artificial Sequence:
                         Synthetic polypeptide"
source                  1..255
                        mol_type = protein
                        organism = synthetic construct
SEQUENCE: 22
MAETVESCLA KPHTENSFTN VWKEGDSRYA NYEGCLWNAG GVVVCTGDET QCYGHWVPIG    60
LAIPENEGGG SEGGGSEGGG SEGGGTKPPE YGDTPIPGYT YINPLDGTYP PGTEQNPANP    120
NPSLEESQPL NTFMFQNNRF RAVNGVLTVY TGTFTQGTDP VKTYYQYTPV SSRAMYDAYW    180
NGKFRDCAFH SGFNEDPFVC EYQGQSSDLP QPPANAGGES GGGSGGGSEG GGSEGGGSEG    240
GGSEGGGSGG GSGSG                                                    255
```

```
SEQ ID NO: 23            moltype = AA  length = 255
FEATURE                  Location/Qualifiers
REGION                   1..255
                         note = source = /note="Description of Artificial Sequence:
                         Synthetic polypeptide"
source                   1..255
                         mol_type = protein
                         organism = synthetic construct
SEQUENCE: 23
MAETVESCLA KPHTENSFTN VWKEGDSRYA NYEGCLWNAG GVVVCTGDEH QCYGTWVPIG   60
LAIPENEGGG SEGGGSEGGG SEGGGTKPPE YGDTPIPGYT YINPLDGTYP PGTEQNPANP  120
NPSLEESQPL NTFMFQGNRF RARQGALTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSG                                                  255

SEQ ID NO: 24            moltype = AA  length = 255
FEATURE                  Location/Qualifiers
REGION                   1..255
                         note = source = /note="Description of Artificial Sequence:
                         Synthetic polypeptide"
source                   1..255
                         mol_type = protein
                         organism = synthetic construct
SEQUENCE: 24
MAETVESCLA KPHTENSFTN VWKEGDSRYA NYEGCLWNAG GVVVCTGDEH QCYGTWVPIG   60
LAIPENEGGG SEGGGSEGGG SEGGGTKPPE YGDTPIPGYT YINPLDGTYP PGTEQNPANP  120
NPSLEESQPL NTFMFQNNRF RAVNGVLTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSG                                                  255

SEQ ID NO: 25            moltype = AA  length = 255
FEATURE                  Location/Qualifiers
REGION                   1..255
                         note = source = /note="Description of Artificial Sequence:
                         Synthetic polypeptide"
source                   1..255
                         mol_type = protein
                         organism = synthetic construct
SEQUENCE: 25
MAETVESCLA KPHTENSFTN VWKEGDSRYA NYEGCLWNAG GVVVCTGDEH QCYGTWVPIG   60
LAIPENEGGG SEGGGSEGGG SEGGGTKPPE YGDTPIPGYT YINPLDGTYP PGTEQNPANP  120
NPSLEESQPL NTFMFQGNRF RNRQGALTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSG                                                  255

SEQ ID NO: 26            moltype = AA  length = 255
FEATURE                  Location/Qualifiers
REGION                   1..255
                         note = source = /note="Description of Artificial Sequence:
                         Synthetic polypeptide"
source                   1..255
                         mol_type = protein
                         organism = synthetic construct
SEQUENCE: 26
MAETVESCLA KPHTENSFTN VWKEGDSRYA NYEGCLWAAG GVVVCTGDEH QCYGTWVPIG   60
LAIPENEGGG SEGGGSEGGG SEGGGTKPPE YGDTPIPGYT YINPLDGTYP PGTEQNPANP  120
NPSLEESQPL NTFMFQGNRF RNRQGALTVY TGTFTQGTDP VKTYYQYTPV SSRAMYDAYW  180
NGKFRDCAFH SGFNEDPFVC EYQGQSSDLP QPPANAGGES GGGSGGGSEG GGSEGGGSEG  240
GGSEGGGSGG GSGSG                                                  255

SEQ ID NO: 27            moltype = AA  length = 5
FEATURE                  Location/Qualifiers
REGION                   1..5
                         note = source = /note="Description of Artificial Sequence:
                         Synthetic peptide"
source                   1..5
                         mol_type = protein
                         organism = synthetic construct
SEQUENCE: 27
GGGGS                                                               5

SEQ ID NO: 28            moltype = AA  length = 4
FEATURE                  Location/Qualifiers
REGION                   1..4
                         note = source = /note="Description of Artificial Sequence:
                         Synthetic peptide"
source                   1..4
                         mol_type = protein
                         organism = synthetic construct
```

```
SEQUENCE: 28
GGGS                                                                        4

SEQ ID NO: 29           moltype = AA   length = 485
FEATURE                 Location/Qualifiers
REGION                  1..485
                        note = source = /note="Description of Artificial Sequence:
                        Synthetic polypeptide"
source                  1..485
                        mol_type = protein
                        organism = synthetic construct
SEQUENCE: 29
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP 120
NPSLEESQPL NTFMFQGNRF RNRQGALTVY TGTFTQGTDP VKTYYQYTPV SSRAMYDAYW 180
NGKFRDCAFH SGFNEDPFVC EYQGQSSDLP QPPANAGGES GGGSGGGSEG GGSEGGGSEG 240
GGSEGGGSGG GSGSGARSDK THTCPPCPAP ELLGGPSVFL FPPKPKDTLM ISRTPEVTCV 300
VVDVSHEDPE VKFNWYVDGV EVHNAKTKPR EEQYNSTYRV VSVLTVLHQD WLNGKEYKCK 360
VSNKALPAPI EKTISKAKGQ PREPQVYTLP PSREEMTKNQ VSLTCLVKGF YPSDIAVEWE 420
SNGQPENNYK TTPPVLDSDG SFFLYSKLTV DKSRWQQGNV FSCSVMHEAL HNHYTQKSLS 480
LSPGK                                                             485

SEQ ID NO: 30           moltype = AA   length = 485
FEATURE                 Location/Qualifiers
REGION                  1..485
                        note = source = /note="Description of Artificial Sequence:
                        Synthetic polypeptide"
source                  1..485
                        mol_type = protein
                        organism = synthetic construct
SEQUENCE: 30
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP 120
NPSLEESQPL NTFMFQNNRF RNVNGVLTVY TGTFTQGTDP VKTYYQYTPV SSRAMYDAYW 180
NGKFRDCAFH SGFNEDPFVC EYQGQSSDLP QPPANAGGES GGGSGGGSEG GGSEGGGSEG 240
GGSEGGGSGG GSGSGARSDK THTCPPCPAP ELLGGPSVFL FPPKPKDTLM ISRTPEVTCV 300
VVDVSHEDPE VKFNWYVDGV EVHNAKTKPR EEQYNSTYRV VSVLTVLHQD WLNGKEYKCK 360
VSNKALPAPI EKTISKAKGQ PREPQVYTLP PSREEMTKNQ VSLTCLVKGF YPSDIAVEWE 420
SNGQPENNYK TTPPVLDSDG SFFLYSKLTV DKSRWQQGNV FSCSVMHEAL HNHYTQKSLS 480
LSPGK                                                             485

SEQ ID NO: 31           moltype = AA   length = 485
FEATURE                 Location/Qualifiers
REGION                  1..485
                        note = source = /note="Description of Artificial Sequence:
                        Synthetic polypeptide"
source                  1..485
                        mol_type = protein
                        organism = synthetic construct
SEQUENCE: 31
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP 120
NPSLEESQPL NTFMFQGNRF RARQGALTVY TGTFTQGTDP VKTYYQYTPV SSRAMYDAYW 180
NGKFRDCAFH SGFNEDPFVC EYQGQSSDLP QPPANAGGES GGGSGGGSEG GGSEGGGSEG 240
GGSEGGGSGG GSGSGARSDK THTCPPCPAP ELLGGPSVFL FPPKPKDTLM ISRTPEVTCV 300
VVDVSHEDPE VKFNWYVDGV EVHNAKTKPR EEQYNSTYRV VSVLTVLHQD WLNGKEYKCK 360
VSNKALPAPI EKTISKAKGQ PREPQVYTLP PSREEMTKNQ VSLTCLVKGF YPSDIAVEWE 420
SNGQPENNYK TTPPVLDSDG SFFLYSKLTV DKSRWQQGNV FSCSVMHEAL HNHYTQKSLS 480
LSPGK                                                             485

SEQ ID NO: 32           moltype = AA   length = 485
FEATURE                 Location/Qualifiers
REGION                  1..485
                        note = source = /note="Description of Artificial Sequence:
                        Synthetic polypeptide"
source                  1..485
                        mol_type = protein
                        organism = synthetic construct
SEQUENCE: 32
MAETVESCLA KPHTENSFTN VWKEGDSRYA NYEGCLWNAG GVVVCTGDET QCYGHWVPIG  60
LAIPENEGGG SEGGGSEGGG SEGGGTKPPE YGDTPIPGYT YINPLDGTYP PGTEQNPANP 120
NPSLEESQPL NTFMFQNNRF RAVNGVLTVY TGTFTQGTDP VKTYYQYTPV SSRAMYDAYW 180
NGKFRDCAFH SGFNEDPFVC EYQGQSSDLP QPPANAGGES GGGSGGGSEG GGSEGGGSEG 240
GGSEGGGSGG GSGSGARSDK THTCPPCPAP ELLGGPSVFL FPPKPKDTLM ISRTPEVTCV 300
VVDVSHEDPE VKFNWYVDGV EVHNAKTKPR EEQYNSTYRV VSVLTVLHQD WLNGKEYKCK 360
VSNKALPAPI EKTISKAKGQ PREPQVYTLP PSREEMTKNQ VSLTCLVKGF YPSDIAVEWE 420
SNGQPENNYK TTPPVLDSDG SFFLYSKLTV DKSRWQQGNV FSCSVMHEAL HNHYTQKSLS 480
LSPGK                                                             485
```

```
SEQ ID NO: 33            moltype = AA  length = 485
FEATURE                  Location/Qualifiers
REGION                   1..485
                         note = source = /note="Description of Artificial Sequence:
                         Synthetic polypeptide"
source                   1..485
                         mol_type = protein
                         organism = synthetic construct
SEQUENCE: 33
MAETVESCLA KPHTENSFTN VWKEGDSRYA NYEGCLWNAG GVVVCTGDEH QCYGTWVPIG    60
LAIPENEGGG SEGGGSEGGG SEGGGTKPPE YGDTPIPGYT YINPLDGTYP PGTEQNPANP   120
NPSLEESQPL NTFMFQGNRF RARQGALTVY TGTFTQGTDP VKTYYQYTPV SSRAMYDAYW   180
NGKFRDCAFH SGFNEDPFVC EYQGQSSDLP QPPANAGGES GGGSGGGSEG GGSEGGGSEG   240
GGSEGGGSGG GSGSGARSDK THTCPPCPAP ELLGGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREEMTKNQ VSLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 34            moltype = AA  length = 485
FEATURE                  Location/Qualifiers
REGION                   1..485
                         note = source = /note="Description of Artificial Sequence:
                         Synthetic polypeptide"
source                   1..485
                         mol_type = protein
                         organism = synthetic construct
SEQUENCE: 34
MAETVESCLA KPHTENSFTN VWKEGDSRYA NYEGCLWNAG GVVVCTGDEH QCYGTWVPIG    60
LAIPENEGGG SEGGGSEGGG SEGGGTKPPE YGDTPIPGYT YINPLDGTYP PGTEQNPANP   120
NPSLEESQPL NTFMFQNNRF RAVNGVLTVY TGTFTQGTDP VKTYYQYTPV SSRAMYDAYW   180
NGKFRDCAFH SGFNEDPFVC EYQGQSSDLP QPPANAGGES GGGSGGGSEG GGSEGGGSEG   240
GGSEGGGSGG GSGSGARSDK THTCPPCPAP ELLGGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREEMTKNQ VSLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 35            moltype = AA  length = 485
FEATURE                  Location/Qualifiers
REGION                   1..485
                         note = source = /note="Description of Artificial Sequence:
                         Synthetic polypeptide"
source                   1..485
                         mol_type = protein
                         organism = synthetic construct
SEQUENCE: 35
MAETVESCLA KPHTENSFTN VWKEGDSRYA NYEGCLWNAG GVVVCTGDEH QCYGTWVPIG    60
LAIPENEGGG SEGGGSEGGG SEGGGTKPPE YGDTPIPGYT YINPLDGTYP PGTEQNPANP   120
NPSLEESQPL NTFMFQGNRF RNRQGALTVY TGTFTQGTDP VKTYYQYTPV SSRAMYDAYW   180
NGKFRDCAFH SGFNEDPFVC EYQGQSSDLP QPPANAGGES GGGSGGGSEG GGSEGGGSEG   240
GGSEGGGSGG GSGSGARSDK THTCPPCPAP ELLGGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREEMTKNQ VSLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 36            moltype = AA  length = 485
FEATURE                  Location/Qualifiers
REGION                   1..485
                         note = source = /note="Description of Artificial Sequence:
                         Synthetic polypeptide"
source                   1..485
                         mol_type = protein
                         organism = synthetic construct
SEQUENCE: 36
MAETVESCLA KPHTENSFTN VWKEGDSRYA NYEGCLWAAG GVVVCTGDEH QCYGTWVPIG    60
LAIPENEGGG SEGGGSEGGG SEGGGTKPPE YGDTPIPGYT YINPLDGTYP PGTEQNPANP   120
NPSLEESQPL NTFMFQGNRF RNRQGALTVY TGTFTQGTDP VKTYYQYTPV SSRAMYDAYW   180
NGKFRDCAFH SGFNEDPFVC EYQGQSSDLP QPPANAGGES GGGSGGGSEG GGSEGGGSEG   240
GGSEGGGSGG GSGSGARSDK THTCPPCPAP ELLGGPSVFL FPPKPKDTLM ISRTPEVTCV   300
VVDVSHEDPE VKFNWYVDGV EVHNAKTKPR EEQYNSTYRV VSVLTVLHQD WLNGKEYKCK   360
VSNKALPAPI EKTISKAKGQ PREPQVYTLP PSREEMTKNQ VSLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 37            moltype = DNA  length = 765
FEATURE                  Location/Qualifiers
misc_feature             1..765
```

```
                          note = source = /note="Description of Artificial Sequence:
                          Synthetic polynucleotide"
source                    1..765
                          mol_type = other DNA
                          organism = synthetic construct
SEQUENCE: 37
atggccgaaa ccgtggaatc atgtctggcg aagccccata ccgagaactc cttcaccaac   60
gtctggaaag agggcgacag ccgctacgcc aactacgagg gctgcctgtg gaacgccggt  120
ggagtggtcg tctgcaccgg ggatgagact cagtgctacg gacactgggt gcctatcgga  180
ctggccattc ccgagaacga gggggtggt agcgaaggcg gcggatcgga aggcggagga   240
tctgagggag ggggaaccaa gcctccgaa tacggcgaca ctccgatccc cgggtatacg    300
tacatcaatc cgctggacgg gacctacccg cctggaactg agcagaaccc ggccaaccca  360
aaccctagcc tcgaggaatc ccagccgttg aacaccttca tgttccaagg gaaccgcttc  420
aggaacagac agggagcgct gaccgtgtac actggcaccc tcacacaagg caccgacccc  480
gtcaagacct actaccagta cactcctgtg tcctcgcggg ctatgtacga tgcgtactgg  540
aatgggaagt ttcgggactg cgctttccac tccggcttca acgaggatcc attcgtgtgc  600
gaatatcagg gccagagctc cgacctcccc caacccctg caaacgccgg cggagaatcc    660
ggaggggat caggaggcgg aagcgaaggg ggtggatccg aaggaggcgg atccgagggt   720
ggaggctccg aaggggagg ctctggtggt ggctccggat cggga                   765

SEQ ID NO: 38            moltype = DNA length = 765
FEATURE                  Location/Qualifiers
misc_feature             1..765
                          note = source = /note="Description of Artificial Sequence:
                          Synthetic polynucleotide"
source                    1..765
                          mol_type = other DNA
                          organism = synthetic construct
SEQUENCE: 38
atggccgaaa ccgtggaatc atgtctggcg aagccccata ccgagaactc cttcaccaac   60
gtctggaaag agggcgacag ccgctacgcc aactacgagg gctgcctgtg gaacgccggt  120
ggagtggtcg tctgcaccgg ggatgagact cagtgctacg gacactgggt gcctatcgga  180
ctggccattc ccgagaacga gggggtggt agcgaaggcg gcggatcgga aggcggagga   240
tctgagggag ggggaaccaa gcctccgaa tacggcgaca ctccgatccc cgggtatacg    300
tacatcaatc cgctggacgg gacctacccg cctggaactg agcagaaccc ggccaaccca  360
aaccctagcc tcgaggaatc ccagccgttg aacaccttca tgttccaaaa caaccgcttc  420
aggaacgtga acggagtgct gaccgtgtac actggcaccc tcacacaagg caccgacccc  480
gtcaagacct actaccagta cactcctgtg tcctcgcggg ctatgtacga tgcgtactgg  540
aatgggaagt ttcgggactg cgctttccac tccggcttca acgaggatcc attcgtgtgc  600
gaatatcagg gccagagctc cgacctcccc caacccctg caaacgccgg cggagaatcc    660
ggaggggat caggaggcgg aagcgaaggg ggtggatccg aaggaggcgg atccgagggt   720
ggaggctccg aaggggagg ctctggtggt ggctccggat cggga                   765

SEQ ID NO: 39            moltype = DNA length = 765
FEATURE                  Location/Qualifiers
misc_feature             1..765
                          note = source = /note="Description of Artificial Sequence:
                          Synthetic polynucleotide"
source                    1..765
                          mol_type = other DNA
                          organism = synthetic construct
SEQUENCE: 39
atggccgaaa ccgtggaatc atgtctggcg aagccccata ccgagaactc cttcaccaac   60
gtctggaaag agggcgacag ccgctacgcc aactacgagg gctgcctgtg gaacgccggt  120
ggagtggtcg tctgcaccgg ggatgagact cagtgctacg gacactgggt gcctatcgga  180
ctggccattc ccgagaacga gggggtggt agcgaaggcg gcggatcgga aggcggagga   240
tctgagggag ggggaaccaa gcctccgaa tacggcgaca ctccgatccc cgggtatacg    300
tacatcaatc cgctggacgg gacctacccg cctggaactg agcagaaccc ggccaaccca  360
aaccctagcc tcgaggaatc ccagccgttg aacaccttca tgttccaagg gaaccgcttc  420
agggctagac agggagcgct gaccgtgtac actggcaccc tcacacaagg caccgacccc  480
gtcaagacct actaccagta cactcctgtg tcctcgcggg ctatgtacga tgcgtactgg  540
aatgggaagt ttcgggactg cgctttccac tccggcttca acgaggatcc attcgtgtgc  600
gaatatcagg gccagagctc cgacctcccc caacccctg caaacgccgg cggagaatcc    660
ggaggggat caggaggcgg aagcgaaggg ggtggatccg aaggaggcgg atccgagggt   720
ggaggctccg aaggggagg ctctggtggt ggctccggat cggga                   765

SEQ ID NO: 40            moltype = DNA length = 765
FEATURE                  Location/Qualifiers
misc_feature             1..765
                          note = source = /note="Description of Artificial Sequence:
                          Synthetic polynucleotide"
source                    1..765
                          mol_type = other DNA
                          organism = synthetic construct
SEQUENCE: 40
atggccgaaa ccgtggaatc atgtctggcg aagccccata ccgagaactc cttcaccaac   60
gtctggaaag agggcgacag ccgctacgcc aactacgagg gctgcctgtg gaacgccggt  120
ggagtggtcg tctgcaccgg ggatgagact cagtgctacg gacactgggt gcctatcgga  180
ctggccattc ccgagaacga gggggtggt agcgaaggcg gcggatcgga aggcggagga   240
```

```
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaaaa caaccgcttc   420
agggccgtga acgagtgct gaccgtgtac actggcacct tcacacaagg caccgacccc    480
gtcaagacct actaccagta cactcctgtg tcctcgcggg ctatgtacga tgcgtactgg   540
aatgggaagt ttcgggactg cgctttccac tccggcttca acgaggatcc attcgtgtgc   600
gaatatcagg gccagagctc cgacctcccc caacccctg caaacgccgg cggagaatcc    660
ggaggggat caggaggcgg aagcgaaggg ggtggatccg aaggaggcgg atccgagggt    720
ggaggctccg aaggggagg ctctggtggt ggctccggat cggga                   765
```

SEQ ID NO: 41          moltype = DNA   length = 765
FEATURE                Location/Qualifiers
misc_feature           1..765
                       note = source = /note="Description of Artificial Sequence:
                       Synthetic polynucleotide"
source                 1..765
                       mol_type = other DNA
                       organism = synthetic construct
SEQUENCE: 41

```
atggccgaaa ccgtggaatc atgtctggcg aagcccata ccgagaactc cttcaccaac    60
gtctggaaag agggcgacag ccgctacgcc aactacgagg gctgcctgtg gaacgccggt   120
ggagtggtcg tctgcaccgg ggatgagcac cagtgctacg gaacttgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
agggctagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgctttccac tccggcttca acgaggatcc attcgtgtgc   600
gaatatcagg gccagagctc cgacctcccc caacccctg caaacgccgg cggagaatcc    660
ggaggggat caggaggcgg aagcgaaggg ggtggatccg aaggaggcgg atccgagggt    720
ggaggctccg aaggggagg ctctggtggt ggctccggat cggga                   765
```

SEQ ID NO: 42          moltype = DNA   length = 765
FEATURE                Location/Qualifiers
misc_feature           1..765
                       note = source = /note="Description of Artificial Sequence:
                       Synthetic polynucleotide"
source                 1..765
                       mol_type = other DNA
                       organism = synthetic construct
SEQUENCE: 42

```
atggccgaaa ccgtggaatc atgtctggcg aagcccata ccgagaactc cttcaccaac    60
gtctggaaag agggcgacag ccgctacgcc aactacgagg gctgcctgtg gaacgccggt   120
ggagtggtcg tctgcaccgg ggatgagcac cagtgctacg gaacttgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaaaa caaccgcttc   420
agggccgtga acgagtgct gaccgtgtac actggcacct tcacacaagg caccgacccc    480
gtcaagacct actaccagta cactcctgtg tcctcgcggg ctatgtacga tgcgtactgg   540
aatgggaagt ttcgggactg cgctttccac tccggcttca acgaggatcc attcgtgtgc   600
gaatatcagg gccagagctc cgacctcccc caacccctg caaacgccgg cggagaatcc    660
ggaggggat caggaggcgg aagcgaaggg ggtggatccg aaggaggcgg atccgagggt    720
ggaggctccg aaggggagg ctctggtggt ggctccggat cggga                   765
```

SEQ ID NO: 43          moltype = DNA   length = 765
FEATURE                Location/Qualifiers
misc_feature           1..765
                       note = source = /note="Description of Artificial Sequence:
                       Synthetic polynucleotide"
source                 1..765
                       mol_type = other DNA
                       organism = synthetic construct
SEQUENCE: 43

```
atggccgaaa ccgtggaatc atgtctggcg aagcccata ccgagaactc cttcaccaac    60
gtctggaaag agggcgacag ccgctacgcc aactacgagg gctgcctgtg gaacgccggt   120
ggagtggtcg tctgcaccgg ggatgagcat cagtgctacg gaacctgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
aggaacagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgctttccac tccggcttca acgaggatcc attcgtgtgc   600
gaatatcagg gccagagctc cgacctcccc caacccctg caaacgccgg cggagaatcc    660
ggaggggat caggaggcgg aagcgaaggg ggtggatccg aaggaggcgg atccgagggt    720
ggaggctccg aaggggagg ctctggtggt ggctccggat cggga                   765
```

| SEQ ID NO: 44 | moltype = DNA   length = 765 |
| --- | --- |
| FEATURE | Location/Qualifiers |
| misc_feature | 1..765 |
| | note = source = /note="Description of Artificial Sequence: Synthetic polynucleotide" |
| source | 1..765 |
| | mol_type = other DNA |
| | organism = synthetic construct |

SEQUENCE: 44

```
atggccgaaa ccgtggaatc atgtctggcg aagccccata ccgagaactc cttcaccaac   60
gtctggaaag agggcgacag ccgctacgcc aactacgagg ctgcctgtg gccgccggt   120
ggagtggtcg tctgcaccgg ggatgagcat cagtgctacg aacctgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
aggaacagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgcttttccac tccggcttca acgaggatcc attcgtgtgc   600
gaatatcagg gccagagctc cgacctcccc caaccccctg caaacgccgg cggagaatcc   660
ggaggggat caggaggcgg aagcgaaggg ggtggatccg aaggaggcgg atccgagggt   720
ggaggctccg aaggggagg ctctggtggt ggctccggat cggga          765
```

| SEQ ID NO: 45 | moltype = DNA   length = 1458 |
| --- | --- |
| FEATURE | Location/Qualifiers |
| misc_feature | 1..1458 |
| | note = source = /note="Description of Artificial Sequence: Synthetic polynucleotide" |
| source | 1..1458 |
| | mol_type = other DNA |
| | organism = synthetic construct |

SEQUENCE: 45

```
atggccgaaa ccgtggaatc atgtctggcg aagccccata ccgagaactc cttcaccaac   60
gtctggaaag agggcgacag ccgctacgcc aactacgagg ctgcctgtg gaacgccggt   120
ggagtggtcg tctgcaccgg ggatgagact cagtgctacg acactgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
aggaacagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgcttttccac tccggcttca acgaggatcc attcgtgtgc   600
gaatatcagg gccagagctc cgacctcccc caaccccctg caaacgccgg cggagaatcc   660
ggaggggat caggaggcgg aagcgaaggg ggtggatccg aaggaggcgg atccgagggt   720
ggaggctccg aaggggagg ctctggtggt ggctccggat cgggagccag atctgacaaa   780
actcacacat gcccaccgtg cccagcacct gaactcctgg ggggaccgtc agtcttcctc   840
ttcccccaa aacccaagga caccctcatg atctcccgga cccctgaggt cacatgcgtg   900
gtggtggacg tgagccacga agaccctgag gtcaagttca actggtacgt ggacggcgtg   960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca agccctccc agcccccatc gagaaaacca tctccaaagc caaagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga          1458
```

| SEQ ID NO: 46 | moltype = DNA   length = 1458 |
| --- | --- |
| FEATURE | Location/Qualifiers |
| misc_feature | 1..1458 |
| | note = source = /note="Description of Artificial Sequence: Synthetic polynucleotide" |
| source | 1..1458 |
| | mol_type = other DNA |
| | organism = synthetic construct |

SEQUENCE: 46

```
atggccgaaa ccgtggaatc atgtctggcg aagccccata ccgagaactc cttcaccaac   60
gtctggaaag agggcgacag ccgctacgcc aactacgagg ctgcctgtg gaacgccggt   120
ggagtggtcg tctgcaccgg ggatgagact cagtgctacg acactgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaaaa caaccgcttc   420
aggaacgtga acggagtgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgcttttccac tccggcttca acgaggatcc attcgtgtgc   600
gaatatcagg gccagagctc cgacctcccc caaccccctg caaacgccgg cggagaatcc   660
ggaggggat caggaggcgg aagcgaaggg ggtggatccg aaggaggcgg atccgagggt   720
```

```
ggaggctccg aagggggagg ctctggtggt ggctccggat cgggagccag atctgacaaa    780
actcacacat gcccaccgtg cccagcacct gaactcctgg ggggaccgtc agtcttcctc    840
ttcccccaa  aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca agcccctccc agcccccatc gagaaaacca tctccaaagc caaagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga                                                  1458

SEQ ID NO: 47        moltype = DNA  length = 1458
FEATURE              Location/Qualifiers
misc_feature         1..1458
                     note = source = /note="Description of Artificial Sequence:
                     Synthetic polynucleotide"
source               1..1458
                     mol_type = other DNA
                     organism = synthetic construct
SEQUENCE: 47
atggccgaaa ccgtggaatc atgtctggcg aagcccccata ccgagaactc cttcaccaac    60
gtctggaaag agggcgacag ccgctacgcc aactacgagg gctgcctgtg aacgccggt    120
ggagtggtcg tctgcaccgg ggatgagact cagtgctacg acactgggt gcctatcgga    180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
agggctagac agggagcgct gaccgtgtac actggcacct tcacacaagg caccgacccc   480
gtcaagacct actaccagta cactcctgtg tcctcgcggg ctatgtacga tgcgtactgg   540
aatgggaagt tcgggactg cgcttttcca tccggcttca acgaggatcc attcgtgtgc   600
gaatatcagg gccagagctc cgacctcccc caaccccctg caaacgccgg cggagaatcc   660
ggagggggat caggaggcgg aagcgaaggg ggtggatccg aaggaggcgg atccgagggt   720
ggaggctccg aagggggagg ctctggtggt ggctccggat cgggagccag atctgacaaa    780
actcacacat gcccaccgtg cccagcacct gaactcctgg ggggaccgtc agtcttcctc    840
ttcccccaa  aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca agcccctccc agcccccatc gagaaaacca tctccaaagc caaagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga                                                  1458

SEQ ID NO: 48        moltype = DNA  length = 1458
FEATURE              Location/Qualifiers
misc_feature         1..1458
                     note = source = /note="Description of Artificial Sequence:
                     Synthetic polynucleotide"
source               1..1458
                     mol_type = other DNA
                     organism = synthetic construct
SEQUENCE: 48
atggccgaaa ccgtggaatc atgtctggcg aagcccccata ccgagaactc cttcaccaac    60
gtctggaaag agggcgacag ccgctacgcc aactacgagg gctgcctgtg aacgccggt    120
ggagtggtcg tctgcaccgg ggatgagact cagtgctacg acactgggt gcctatcgga    180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaaaa caaccgcttc   420
agggccgtga acgagtgct gaccgtgtac actggcacct tcacacaagg caccgacccc   480
gtcaagacct actaccagta cactcctgtg tcctcgcggg ctatgtacga tgcgtactgg   540
aatgggaagt tcgggactg cgcttttcca tccggcttca acgaggatcc attcgtgtgc   600
gaatatcagg gccagagctc cgacctcccc caaccccctg caaacgccgg cggagaatcc   660
ggagggggat caggaggcgg aagcgaaggg ggtggatccg aaggaggcgg atccgagggt   720
ggaggctccg aagggggagg ctctggtggt ggctccggat cgggagccag atctgacaaa    780
actcacacat gcccaccgtg cccagcacct gaactcctgg ggggaccgtc agtcttcctc    840
ttcccccaa  aacccaagga caccctcatg atctcccgga cccctgaggt cacatgcgtg    900
gtggtggacg tgagccacga agaccctgag gtcaagttca actggtacgt ggacggcgtg    960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca agcccctccc agcccccatc gagaaaacca tctccaaagc caaagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
```

```
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga                                                1458

SEQ ID NO: 49           moltype = DNA  length = 1458
FEATURE                 Location/Qualifiers
misc_feature            1..1458
                        note = source = /note="Description of Artificial Sequence:
                         Synthetic polynucleotide"
source                  1..1458
                        mol_type = other DNA
                        organism = synthetic construct
SEQUENCE: 49
atggccgaaa ccgtggaatc atgtctggcg aagccccata ccgagaactc cttcaccaac    60
gtctggaaag agggcgacag ccgctacgcc aactacgagg gctgcctgtg gaacgccggt   120
ggagtggtcg tctgcaccgg ggatgagcac cagtgctacg gaacttgggt gcctatcgga   180
ctggccattc ccgagaacga gggggtggt agcgaaggcg gcggatcgga aggcggagga   240
tctgagggag ggggaaccaa gcctccgaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
agggctagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcggggactg cgctttccac tccggcttca acgaggatcc attcgtgtgc   600
gaatatcagg gccagagctc cgacctcccc caaccccctg caaacgccgg cggagaatcc   660
ggaggggat caggaggcgg aagcgaaggg ggtggatccg aaggaggcgg atccgagggt   720
ggaggctccg aagggggagg ctctggtggt ggctccggat cgggagccag atctgacaaa   780
actcacacat gcccaccgtg cccagcacct gaactcctgg ggggaccgtc agtcttcctc   840
ttccccccaa aacccaagga caccctcatg atctcccgga cccctgaggt cacatgcgtg   900
gtggtggacg tgagccacga agaccctgag gtcaagttca actggtacgt ggacggcgtg   960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca aagccctccc agcccccatc gagaaaacca tctccaaagc caagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga                                                1458

SEQ ID NO: 50           moltype = DNA  length = 1458
FEATURE                 Location/Qualifiers
misc_feature            1..1458
                        note = source = /note="Description of Artificial Sequence:
                         Synthetic polynucleotide"
source                  1..1458
                        mol_type = other DNA
                        organism = synthetic construct
SEQUENCE: 50
atggccgaaa ccgtggaatc atgtctggcg aagccccata ccgagaactc cttcaccaac    60
gtctggaaag agggcgacag ccgctacgcc aactacgagg gctgcctgtg gaacgccggt   120
ggagtggtcg tctgcaccgg ggatgagcac cagtgctacg gaacttgggt gcctatcgga   180
ctggccattc ccgagaacga gggggtggt agcgaaggcg gcgatcgga aggcggagga   240
tctgagggag ggggaaccaa gcctccgaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaaaa caaccgcttc   420
agggccgtga acggagtgct gaccgtgtac actggcacct tcacacaagg caccgacccc   480
gtcaagacct actaccagta cactcctgtg tcctcgcggg ctatgtacga tgcgtactgg   540
aatgggaagt ttcggggactg cgctttccac tccggcttca acgaggatcc attcgtgtgc   600
gaatatcagg gccagagctc cgacctcccc caaccccctg caaacgccgg cggagaatcc   660
ggaggggat caggaggcgg aagcgaaggg ggtggatccg aaggaggcgg atccgagggt   720
ggaggctccg aagggggagg ctctggtggt ggctccggat cgggagccag atctgacaaa   780
actcacacat gcccaccgtg cccagcacct gaactcctgg ggggaccgtc agtcttcctc   840
ttccccccaa aacccaagga caccctcatg atctcccgga cccctgaggt cacatgcgtg   900
gtggtggacg tgagccacga agaccctgag gtcaagttca actggtacgt ggacggcgtg   960
gaggtgcata atgccaagac aaagccgcgg gaggagcagt acaacagcac gtaccgtgtg   1020
gtcagcgtcc tcaccgtcct gcaccaggac tggctgaatg gcaaggagta caagtgcaag   1080
gtctccaaca aagccctccc agcccccatc gagaaaacca tctccaaagc caagggcag   1140
ccccgagaac cacaggtgta caccctgccc ccatcccggg aggagatgac caagaaccag   1200
gtcagcctga cctgcctggt caaaggcttc tatcccagcg acatcgccgt ggagtgggag   1260
agcaatgggc agccggagaa caactacaag accacgcctc ccgtgctgga ctccgacggc   1320
tccttcttcc tctacagcaa gctcaccgtg gacaagagca ggtggcagca ggggaacgtc   1380
ttctcatgct ccgtgatgca cgaggctctg cacaaccact acacgcagaa gagcctctcc   1440
ctgtctccgg gtaaatga                                                1458

SEQ ID NO: 51           moltype = DNA  length = 1458
FEATURE                 Location/Qualifiers
misc_feature            1..1458
                        note = source = /note="Description of Artificial Sequence:
```

```
                        Synthetic polynucleotide"
source                  1..1458
                        mol_type = other DNA
                        organism = synthetic construct
SEQUENCE: 51
atggccgaaa ccgtggaatc atgtctggcg aagccccata ccgagaactc cttcaccaac    60
gtctggaaag agggcgacag ccgctacgcc aactacgagg gctgcctgtg gaacgccggt   120
ggagtggtcg tctgcactgg ggatgagcac cagtgctacg gaacctgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
aggaacagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgcttttcca tccggcttca acgaggatcc attcgtgtgc   600
gaatatcagg gccagagctc cgacctcccc caaccccctg caaacgccgg cggagaatcc   660
ggagggggat caggaggcgg aagcgaaggg ggtggatccg aaggaggcgg atccgagggt   720
ggaggctccg aaggggagg ctctggtggt ggctccggat cgggagccag atctgacaaa   780
actcacacat gcccaccgtg cccagcacct gaactcctgg ggggaccgtc agtcttcctc   840
ttccccccaa aacccaagga caccctcatg atctcccgga cccctgaggt cacatgcgtg   900
gtggtggacg tgagccacga agaccctgag gtcaagttca actggtacgt ggacggcgtg   960
gaggtgcata atgccaagac aaagccgcgg gaggagcagt acaacagcac gtaccgtgtg  1020
gtcagcgtcc tcaccgtcct gcaccaggac tggctgaatg gcaaggagta caagtgcaag  1080
gtctccaaca agccctccc agccccatc gagaaaacca tctccaaagc caaagggcag  1140
ccccgagaac acaggtgta caccctgccc ccatcccggg aggagatgac caagaaccag  1200
gtcagcctga cctgcctggt caaaggcttc tatcccagcg acatcgccgt ggagtgggag  1260
agcaatgggc agccggagaa caactacaag accacgcctc ccgtgctgga ctccgacggc  1320
tccttcttcc tctacagcaa gctcaccgtg gacaagagca ggtggcagca ggggaacgtc  1380
ttctcatgct ccgtgatgca cgaggctctg cacaaccact acacgcagaa gagcctctcc  1440
ctgtctccgg gtaaatga                                                1458

SEQ ID NO: 52           moltype = DNA  length = 1458
FEATURE                 Location/Qualifiers
misc_feature            1..1458
                        note = source = /note="Description of Artificial Sequence:
                        Synthetic polynucleotide"
source                  1..1458
                        mol_type = other DNA
                        organism = synthetic construct
SEQUENCE: 52
atggccgaaa ccgtggaatc atgtctggcg aagccccata ccgagaactc cttcaccaac    60
gtctggaaag agggcgacag ccgctacgcc aactacgagg gctgcctgtg ggccgccggt   120
ggagtggtcg tctgcactgg ggatgagcac cagtgctacg gaacctgggt gcctatcgga   180
ctggccattc ccgagaacga ggggggtggt agcgaaggcg gcggatcgga aggcggagga   240
tctgagggag ggggaaccaa gcctccggaa tacggcgaca ctccgatccc cgggtatacg   300
tacatcaatc cgctggacgg gacctacccg cctggaactg agcagaaccc ggccaaccca   360
aaccctagcc tcgaggaatc ccagccgttg aacaccttca tgttccaagg gaaccgcttc   420
aggaacagac agggagcgct gaccgtgtac actggcacct tcacacaagg caccgacccc   480
gtcaagacct actaccagta cactcctgtg tcctcgcggg ctatgtacga tgcgtactgg   540
aatgggaagt ttcgggactg cgcttttcca tccggcttca acgaggatcc attcgtgtgc   600
gaatatcagg gccagagctc cgacctcccc caaccccctg caaacgccgg cggagaatcc   660
ggagggggat caggaggcgg aagcgaaggg ggtggatccg aaggaggcgg atccgagggt   720
ggaggctccg aaggggagg ctctggtggt ggctccggat cgggagccag atctgacaaa   780
actcacacat gcccaccgtg cccagcacct gaactcctgg ggggaccgtc agtcttcctc   840
ttccccccaa aacccaagga caccctcatg atctcccgga cccctgaggt cacatgcgtg   900
gtggtggacg tgagccacga agaccctgag gtcaagttca actggtacgt ggacggcgtg   960
gaggtgcata atgccaagac aaagccgcgg gaggagcagt acaacagcac gtaccgtgtg  1020
gtcagcgtcc tcaccgtcct gcaccaggac tggctgaatg gcaaggagta caagtgcaag  1080
gtctccaaca agccctccc agccccatc gagaaaacca tctccaaagc caaagggcag  1140
ccccgagaac acaggtgta caccctgccc ccatcccggg aggagatgac caagaaccag  1200
gtcagcctga cctgcctggt caaaggcttc tatcccagcg acatcgccgt ggagtgggag  1260
agcaatgggc agccggagaa caactacaag accacgcctc ccgtgctgga ctccgacggc  1320
tccttcttcc tctacagcaa gctcaccgtg gacaagagca ggtggcagca ggggaacgtc  1380
ttctcatgct ccgtgatgca cgaggctctg cacaaccact acacgcagaa gagcctctcc  1440
ctgtctccgg gtaaatga                                                1458

SEQ ID NO: 53           moltype = AA  length = 6
FEATURE                 Location/Qualifiers
REGION                  1..6
                        note = source = /note="Description of Artificial Sequence:
                        Synthetic 6xHis tag"
source                  1..6
                        mol_type = protein
                        organism = synthetic construct
SEQUENCE: 53
HHHHHH                                                                  6

SEQ ID NO: 54           moltype = AA  length = 4
FEATURE                 Location/Qualifiers
```

```
REGION           1..4
                 note = source = /note="Description of Artificial Sequence:
                 Synthetic peptide"
source           1..4
                 mol_type = protein
                 organism = synthetic construct
SEQUENCE: 54
EDGS                                                                 4
```

We claim:

1. A method of treating a disease associated with misfolded and/or aggregated amyloid protein, comprising administering to a subject in need thereof a polypeptide comprising a variant of starting amino acid sequence SEQ ID NO: 16, wherein the variant differs from SEQ ID NO: 16 by one or more sets of amino acid changes selected from:
   a) substitution of T50 with any amino acid and H55T;
   b) N137G;
   c) N142A;
   d) R143V and Q144N; or
   R143V, Q144N, and A146V; or
   R143V, Q144N, and A146T; or
   R143V, Q144N, and A146K; and
   e) Q156V, G157N, ΔT158, ΔD159, ΔP160, and V161G; or
   Q156Y, G157N, ΔT158, ΔD159, ΔP160, and V161G; or
   G157N, ΔT158, ΔD159, ΔP160, and V161G; or
   ΔT158, ΔD159, ΔP160, and V161G;
wherein the variant optionally further differs from SEQ ID NO: 16 by one or more sets of amino acid changes selected from:
   f) ΔM1; or
   ΔM1 and ΔA2; and
   g) substitution of N38 with any amino acid other than cysteine; or
   substitution of N38 with any amino acid other than cysteine, and substitution of G40 with any amino acid other than cysteine; or
   substitution of G40 with any amino acid other than cysteine, threonine, or serine.

2. The method of claim 1, wherein the T50 substitution is selected from the group consisting of T50G, T50H, T50K, and T50R.

3. The method of claim 2, wherein the T50 substitution is T50H.

4. The method of claim 1, wherein the variant differs from SEQ ID NO: 16 at least by ΔM1 and ΔA2.

5. The method of claim 1, wherein the variant differs from SEQ ID NO: 16 at least by N137G and/or N142A.

6. The method of claim 4, wherein the variant further differs from SEQ ID NO: 16 by one or more sets of amino acid changes selected from:
   a) substitution of T50 with any amino acid and H55T; and
   b) R143V and Q144N; or
   R143V, Q144N, and A146V; or
   R143V, Q144N, and A146T; or
   R143V, Q144N, and A146K.

7. The method of claim 6, wherein the T50 substitution is selected from the group consisting of T50G, T50H, T50K, and T50R.

8. The method of claim 7, wherein the T50 substitution is T50H.

9. The method of claim 1, wherein the variant of SEQ ID NO: 16 is selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26.

10. The method of claim 1, wherein said polypeptide further comprises an immunoglobulin constant region.

11. The method of claim 10, wherein the immunoglobulin constant region sequence is the Fc portion of a human IgG.

12. The method of claim 11, wherein said polypeptide is fused at the C-terminal end to the Fc portion of a human IgG.

13. The method of claim 12, wherein the human IgG is human IgG1.

14. The method of claim 1, wherein said polypeptide consists essentially of an amino acid sequence selected from:
   a) SEQ ID NO: 29;
   b) SEQ ID NQ: 30;
   c) SEQ ID NO: 31;
   d) SEQ ID NO: 32;
   e) SEQ ID NO: 33;
   f) SEQ ID NO: 34;
   g) SEQ ID NO: 35; and
   h) SEQ ID NO: 36;
wherein the variant optionally has one or more sets of amino acid changes selected from:
   i) ΔM1; or
   ΔM1 and ΔA2; and
   j) ΔK485.

15. The method according to claim 1, wherein said polypeptide is administered as a pharmaceutical composition further comprising a pharmaceutically acceptable carrier.

16. The method according to claim 1, wherein said treatment results in reducing amyloid, inhibiting amyloid formation, inhibiting amyloid aggregation, or removing and/or preventing the formation of toxic oligomers in said subject in need thereof.

17. The method of claim 16, wherein the amyloid or oligomers comprise a protein selected from Androgen receptor; apolipoprotein AI; apolipoprotein AII; apolipoprotein AIV; aposerum amyloid A; Aβ; ABri; ADan; Atrophin-1; atrial natriuretic factor; ataxin; calcitonin; γ-crystallin; cystatin C; fibrinogen; gelsolin; huntingtin; insulin; islet amyloid polypeptide; immunoglobulin kappa light chain; immunoglobulin lambda light chain; kerato-epithelin; keratin; lactahedrin; lactoferrin; lysozyme; lung surfactant protein C; medin; odontogenic ameloblast-associated protein; prion protein; procalcitonin; prolactin; semenogelin I; serum amyloid A; superoxide dismutase I; β2-microglobulin; TATA box binding protein; tau; transthyretin; and α-synuclein.

18. The method according to claim 1, wherein the disease is selected from Alzheimer's disease; early onset Alzheimer's disease; late onset Alzheimer's disease; presymptomatic Alzheimer's disease; AL amyloidosis; amyotrophic lateral sclerosis (ALS); Amyotrophic lateral sclerosis/parkinsonism-dementia complex; Argyrophilic grain dementia; Aortic medial amyloidosis; ApoAI amyloidosis; ApoAII amyloidosis; ApoAIV amyloidosis; Atrial amyloidosis; British/Danish dementia; Cataract; Corticobasal degeneration; Corneal amyloidosis associated with trichiasis; cystatin C plaque-related disease; cystatin C plaque-related coronary disease; cystatin C plaque-related kidney disease; cutaneous lichen amyloidosis; Dementia pugilistica; dentatorubral-pallidoluysian atrophy; diffuse neurofibrillary tangles with calcification; dementia with Lewy bodies; Down's syndrome; Familial Amyloidotic Cardiomyopathy (FAC); Familial Amyloidotic Polyneuropathy (FAP); Familial British dementia; Familia Danish dementia; familial encephalopathy; Familial Mediterranean fever; Fibrinogen amyloidosis; Finnish hereditary amyloidosis; Frontotemporal dementia with Parkinsonism; frontotemporal lobar degeneration (FTLDs); frontotemporal lobe dementia; Hallervorden-Spatz disease; Hemodialysis-related amyloidosis; hereditary cerebral amyloid angiopathy; hereditary cerebral hemorrhage with amyloidosis; hereditary lattice corneal dystrophy; Huntington's disease; Icelandic hereditary cerebral amyloid angiopathy; Inclusion-body myositis; Injection-localized amyloidosis; islet amyloid polypeptide amyloidosis; Lysozyme amyloidosis; multiple myeloma; Myotonic dystrophy; Niemann-Pick disease type C; Non-Guamanian motor neuron disease with neurofibrillary tangles; Parkinson's disease; peripheral amyloidosis; Pick's disease; Pituitary prolactinoma; Postencephalitic parkinsonism; Prion protein cerebral amyloid angiopathy; prion-mediated disease; kuru; Creutzfeldt-Jakob disease (CJD); Gerstmann-Straussler-Scheinker disease (GSS); fatal familial insomnia (FFI); scrapie; spongiform encephalopathy; pulmonary alveolar proteinosis; Progressive subcortical gliosis; Progressive supranuclear palsy; Senile Systemic Amyloidosis; serum AA amyloidosis; spinal and bulbar muscular atrophy; spinocerebellar ataxia SCA1, SCA3, SCA6, or SCA7; Subacute sclerosing panencephalitis; systemic amyloidosis; familial amyloidosis; wild-type amyloidosis; Tangle only dementia; and Tauopathies, comprising administering to the subject a polypeptide of claim 1 or the pharmaceutical composition of claim 15.

19. The method of claim 18, wherein the disease is selected from Parkinson's disease, Alzheimer's disease, and Huntington's disease.

20. The method of claim 19, wherein the disease is Alzheimer's disease.

21. The method of claim 18, wherein the disease is a prion-mediated disease selected from Creutzfeldt-Jakob disease, kuru, fatal familial insomnia, and Gerstmann-Straussler-Scheinker disease.

22. The method of claim 1, wherein said polypeptide is administered through an oligonucleotide comprising a nucleic acid encoding said polypeptide.

23. The oligonucleotide of claim 22, wherein the nucleic acid encoding the polypeptide comprises a sequence selected from SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44, or wherein the nucleic acid encoding the polypeptide consists of a sequence selected from SEQ ID NO: 45, SEQ ID NO: 46, SEQ ID NO: 47, SEQ ID NO: 48, SEQ ID NO: 49, SEQ ID NQ: 50, SEQ ID NO: 51, and SEQ ID NO: 52.

24. A method for detecting amyloid aggregates in a subject comprising the step of contacting the subject with a polypeptide as defined in claim 1, linked to a detectable label and detecting the presence of said amyloid aggregates.

25. The method according to claim 24, wherein said label is a fluorescent label or a radiolabel.

26. The method according to claim 18, wherein the disease is spinocerebellar ataxia SCA1, SCA3, SCA6, or SCA7.

* * * * *

UNITED STATES PATENT AND TRADEMARK OFFICE
CERTIFICATE OF CORRECTION

PATENT NO. : 12,247,055 B2
APPLICATION NO. : 18/320697
DATED : March 11, 2025
INVENTOR(S) : Krishnan et al.

It is certified that error appears in the above-identified patent and that said Letters Patent is hereby corrected as shown below:

In the Claims

Claim 1, Column 83, Line 35, "f) AM1; or" should read --f) ΔM1; or--.

Claim 14, Column 84, Line 27, "b) SEQ ID NQ: 30;" should read --b) SEQ ID NO: 30;--.

Claim 18, Column 85, Line 34, "spinocerebellar ataxia SCA1, SCA3, SCA6, or SCA7;" should read --spinocerebellar ataxia;--.

Claim 23, Column 86, Line 24, "SEQ ID NQ: 50," should read --SEQ ID NO: 50,--.

Signed and Sealed this
Twenty-ninth Day of April, 2025

Coke Morgan Stewart
*Acting Director of the United States Patent and Trademark Office*